(12) United States Patent
Timmerman et al.

(10) Patent No.: US 7,863,239 B2
(45) Date of Patent: Jan. 4, 2011

(54) BINDING COMPOUNDS, IMMUNOGENIC COMPOUNDS AND PEPTIDOMIMETICS

(75) Inventors: Peter Timmerman, Lelystad (NL);
Wouter Cornelis Puijk, Lelystad (NL);
Jelle Wouter Slootstra, Lelystad (NL);
Evert van Dijk, Giethoorn (NL);
Robbert Hans Meloen, Lelystad (NL)

(73) Assignee: Pepscan Systems B.V., Lelystad (NL)

( * ) Notice: Subject to any disclaimer, the term of this patent is extended or adjusted under 35 U.S.C. 154(b) by 82 days.

(21) Appl. No.: 11/795,922

(22) PCT Filed: Jan. 24, 2006

(86) PCT No.: PCT/NL2006/000036

§ 371 (c)(1),
(2), (4) Date: Oct. 17, 2007

(87) PCT Pub. No.: WO2006/078161

PCT Pub. Date: Jul. 27, 2006

(65) Prior Publication Data

US 2008/0313749 A1 Dec. 18, 2008

(30) Foreign Application Priority Data

Jan. 24, 2005 (EP) .................................. 05075174
Dec. 16, 2005 (EP) .................................. 05077896

(51) Int. Cl.
*A61K 38/00* (2006.01)
(52) U.S. Cl. ........................................................ 514/2
(58) Field of Classification Search ................... None
See application file for complete search history.

(56) References Cited

FOREIGN PATENT DOCUMENTS

| EP | 0 467 699 A | 1/1992 |
|---|---|---|
| EP | 1 452 868 A | 9/2004 |
| EP | 1452868 A2 * | 9/2004 |
| WO | WO 03/095486 A | 11/2003 |
| WO | WO 03/106487 A | 12/2003 |

OTHER PUBLICATIONS

Timmerman et al., Rapid and quantitative cyclization of multiple peptide loops onto synthetic scaffolds for structural mimicry of prot6ein surfaces, Chembiochem: A European Journal of Chemical Biology, May 2005, pp. 821-824, vol. 6, No. 5.
Meloen et al., Design of synthetic peptides for diagnostics, Current Protein & Peptide Science, Aug. 2003, pp. 253-260, vol. 4. No. 4.
Murali et al., Structure-Based Design of Immunologically Active Therapeutic Peptides, Immunologic Research, Jan. 1998, pp. 163-169, vol. 17, No. 1/2.
Timmerman, Mapping of a discontinuous and highly conformational binding site on follicle stimulating hormone subunit-beta (FSH-beta) using domain Scan™ and Matris Scan™ technology, Molecular Diversity, 2004, pp. 61-77, vol. 8, No. 2.
Slootstra et al., Structural Aspects of Antibody-Antigen Interaction Revealed through Small Random Peptide Libraries, Molecular Diversity, Escom Science Publishers, Leiden, NL, 1996, pp. 87-96, vol. 1.
Sun et al., The Cysteine-knot Growth Factor Superfamily, Annual Review of Biophysics and Biomolecular Structure, Annual Reviews Inc., Palo Alto, CA, US, 1995, pp. 269-292, vol. 24.
Vitt et al., Evolution and classification of cystine knot-containing hormones and related extracellular signaling molecules, Molecular Endocrinology, Baltimore, MD, US, May 2001, pp. 681-694, vol. 15, No. 5.
Darling et al., Intracellular folding pathway of the cystine knot-containing glycoprotein hormone alpha-subunit, Biochemistry, American Chemical Society, Easton, PA, US, Jan. 16, 2001, pp. 577-585, vol. 40, No. 2.
PCT International Search Report, PCT/NL2006/000036, dated May 18, 2006.

* cited by examiner

*Primary Examiner*—Christina Bradley
(74) *Attorney, Agent, or Firm*—TraskBritt, P.C.

(57) ABSTRACT

The invention provides means and methods for producing compounds suitable for testing for the presence and/or identification of an immunogenic compound and/or a binding compound of interest. Immunogenic compounds and compositions are also herewith provided, as well as peptidomimetics of members of the cystine-knot family.

17 Claims, 8 Drawing Sheets

$X_{1,2,3}$ = N(H), O, S
*also all other ortho, meta, and para derivatives of the compounds depicted*

$X_{1,2,3}$ = N(H), O, S
*also all other ortho, meta, and para derivatives of the compounds depicted*

$X_{1,2}$ = N(H), O, S
*also all other possible ortho, meta, and para derivatives of the compounds depicted*

SEQUENCE LISTING

```
<160> NUMBER OF SEQ ID NOS: 162

<210> SEQ ID NO 1
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(6)
<223> OTHER INFORMATION: Xaa can be any naturally occurring amino acid

<400> SEQUENCE: 1

Cys Xaa Xaa Xaa Xaa Xaa Cys
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 2

Cys Xaa Xaa Cys
1

<210> SEQ ID NO 3
<211> LENGTH: 12
```

```
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(11)
<223> OTHER INFORMATION: Xaa can be any naturally occurring amino acid

<400> SEQUENCE: 3

Cys Xaa Xaa Xaa Xaa Xaa Xaa Xaa Xaa Xaa Xaa Cys
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(8)
<223> OTHER INFORMATION: Xaa can be any naturally occurring amino acid

<400> SEQUENCE: 4

Cys Xaa Xaa Xaa Xaa Xaa Xaa Xaa Cys
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(11)
<223> OTHER INFORMATION: Xaa can be any naturally occurring amino acid

<400> SEQUENCE: 5

Cys Xaa Xaa Xaa Xaa Xaa Xaa Xaa Xaa Xaa Xaa Cys
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(5)
<223> OTHER INFORMATION: Xaa can be any naturally occurring amino acid

<400> SEQUENCE: 6

Cys Xaa Xaa Xaa Xaa Cys
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(5)
<223> OTHER INFORMATION: Xaa can be any naturally occurring amino acid

<400> SEQUENCE: 7
```

Cys Xaa Xaa Xaa Xaa Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(8)
<223> OTHER INFORMATION: Xaa can be any naturally occurring amino acid

<400> SEQUENCE: 8

Cys Xaa Xaa Xaa Xaa Xaa Xaa Xaa Cys
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(11)
<223> OTHER INFORMATION: Xaa can be any naturally occurring amino acid

<400> SEQUENCE: 9

Cys Xaa Xaa Xaa Xaa Xaa Xaa Xaa Xaa Xaa Xaa Cys
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(16)
<223> OTHER INFORMATION: Xaa can be any naturally occurring amino acid

<400> SEQUENCE: 10

Cys Xaa Xaa Xaa Xaa Xaa Xaa Xaa Xaa Xaa Xaa Xaa Xaa Xaa Xaa Xaa Cys
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(13)
<223> OTHER INFORMATION: Xaa can be any naturally occurring amino acid

<400> SEQUENCE: 11

Cys Xaa Xaa Xaa Xaa Xaa Xaa Xaa Xaa Xaa Xaa Xaa Xaa Cys
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic construct
<220> FEATURE:

```
<221> NAME/KEY: misc_feature
<222> LOCATION: (2)..(16)
<223> OTHER INFORMATION: Xaa can be any naturally occurring amino acid

<400> SEQUENCE: 12

Cys Xaa Xaa Xaa Xaa Xaa Xaa Xaa Xaa Xaa Xaa Xaa Xaa Xaa Xaa Cys
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(13)
<223> OTHER INFORMATION: Xaa can be any naturally occurring amino acid

<400> SEQUENCE: 13

Cys Xaa Xaa Xaa Xaa Xaa Xaa Xaa Xaa Xaa Xaa Xaa Xaa Cys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(10)
<223> OTHER INFORMATION: Xaa can be any naturally occurring amino acid

<400> SEQUENCE: 14

Cys Xaa Xaa Xaa Xaa Xaa Xaa Xaa Xaa Xaa Cys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(13)
<223> OTHER INFORMATION: Xaa can be any naturally occurring amino acid

<400> SEQUENCE: 15

Cys Xaa Xaa Xaa Xaa Xaa Xaa Xaa Xaa Xaa Xaa Xaa Xaa Cys
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(16)
<223> OTHER INFORMATION: Xaa can be any naturally occurring amino acid

<400> SEQUENCE: 16

Cys Xaa Xaa Xaa Xaa Xaa Xaa Xaa Xaa Xaa Xaa Xaa Xaa Xaa Xaa Xaa
1               5                   10                  15

Cys
```

```
<210> SEQ ID NO 17
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(16)
<223> OTHER INFORMATION: Xaa can be any naturally occurring amino acid

<400> SEQUENCE: 17

Cys Xaa Xaa Xaa Xaa Xaa Xaa Xaa Xaa Xaa Xaa Xaa Xaa Xaa Xaa
1               5                   10                  15

Cys

<210> SEQ ID NO 18
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(13)
<223> OTHER INFORMATION: Xaa can be any naturally occurring amino acid

<400> SEQUENCE: 18

Cys Xaa Xaa Xaa Xaa Xaa Xaa Xaa Xaa Xaa Xaa Xaa Xaa Cys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(10)
<223> OTHER INFORMATION: Xaa can be any naturally occurring amino acid

<400> SEQUENCE: 19

Cys Xaa Xaa Xaa Xaa Xaa Xaa Xaa Xaa Xaa Cys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(10)
<223> OTHER INFORMATION: Xaa can be any naturally occurring amino acid

<400> SEQUENCE: 20

Cys Xaa Xaa Xaa Xaa Xaa Xaa Xaa Xaa Xaa Cys
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
```

```
<222> LOCATION: (2)..(7)
<223> OTHER INFORMATION: Xaa can be any naturally occurring amino acid

<400> SEQUENCE: 21

Cys Xaa Xaa Xaa Xaa Xaa Xaa Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(7)
<223> OTHER INFORMATION: Xaa can be any naturally occurring amino acid

<400> SEQUENCE: 22

Cys Xaa Xaa Xaa Xaa Xaa Xaa Cys
1               5

<210> SEQ ID NO 23
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be G, S or R
<220> FEATURE:
<221> NAME/KEY: misc_feature
<222> LOCATION: (3)..(3)
<223> OTHER INFORMATION: Xaa can be K, R or L
<220> FEATURE:
<221> NAME/KEY: misc_feature
<222> LOCATION: (5)..(5)
<223> OTHER INFORMATION: Xaa can be L, I or V
<220> FEATURE:
<221> NAME/KEY: misc_feature
<222> LOCATION: (6)..(6)
<223> OTHER INFORMATION: Xaa can be D or E
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can Y or W
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 23

Xaa Cys Xaa Gly Xaa Xaa Xaa Xaa Xaa Xaa Xaa Ser Xaa Cys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
```

```
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be F or W
<220> FEATURE:
<221> NAME/KEY: misc_feature
<222> LOCATION: (7)..(7)
<223> OTHER INFORMATION: Xaa can be R, Q or S
<220> FEATURE:
<221> NAME/KEY: misc_feature
<222> LOCATION: (9)..(9)
<223> OTHER INFORMATION: Xaa can be F or Y

<400> SEQUENCE: 24

Cys Xaa Gly Cys Xaa Ser Xaa Ala Xaa Pro Thr Pro
 1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 25

Xaa His Thr Xaa Cys Xaa Cys Xaa Thr Cys Xaa Xaa His Lys
 1               5                   10

<210> SEQ ID NO 26
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 26

Cys Xaa Gly Xaa Cys
 1               5

<210> SEQ ID NO 27
<211> LENGTH: 13
<212> TYPE: PRT
<213> ORGANISM: Artificial Sequence
```

```
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be P, S or R
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be G, S, T or A

<400> SEQUENCE: 27

Pro Xaa Cys Val Xaa Xaa Xaa Arg Cys Xaa Gly Cys Cys
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be L, I, V or M
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be F or Y
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 28

Xaa Xaa Xaa Pro Xaa Xaa Xaa Xaa Xaa Xaa Cys Xaa Gly Xaa Cys
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be S, T, A, G or M
<220> FEATURE:
<221> NAME/KEY: misc_feature
<222> LOCATION: (4)..(4)
<223> OTHER INFORMATION: Xaa can be H, F, Y or L
<220> FEATURE:
<221> NAME/KEY: misc_feature
<222> LOCATION: (6)..(6)
```

```
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be S or T

<400> SEQUENCE: 29

Cys Xaa Gly Xaa Cys Xaa Xaa
1               5

<210> SEQ ID NO 30
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be G, S or R
<220> FEATURE:
<221> NAME/KEY: misc_feature
<222> LOCATION: (3)..(3)
<223> OTHER INFORMATION: Xaa can be K, R or L
<220> FEATURE:
<221> NAME/KEY: misc_feature
<222> LOCATION: (5)..(5)
<223> OTHER INFORMATION: Xaa can be L, I or V
<220> FEATURE:
<221> NAME/KEY: misc_feature
<222> LOCATION: (6)..(6)
<223> OTHER INFORMATION: Xaa can be D or E
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be Y or W
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 30

Xaa Cys Xaa Gly Xaa Xaa Xaa Xaa Xaa Xaa Xaa Ser Xaa Cys
1               5                   10

<210> SEQ ID NO 31
<211> LENGTH: 32
<212> TYPE: PRT
<213> ORGANISM: Artificial Sequence
<220> FEATURE:
<223> OTHER INFORMATION: Peptidomimetic FSH

<400> SEQUENCE: 31

Thr Phe Lys Glu Leu Val Tyr Glu Thr Cys Arg Val Pro Gly Ala Ala
1               5                   10                  15

His His Ala Asp Ser Leu Cys Thr Tyr Pro Val Ala Thr Gln Ala His
            20                  25                  30

<210> SEQ ID NO 32
<211> LENGTH: 41
<212> TYPE: PRT
<213> ORGANISM: Artificial Sequence
<220> FEATURE:
<223> OTHER INFORMATION: Peptidomimetic FSH
```

```
<400> SEQUENCE: 32

Lys Ile Gln Lys Thr Ala Thr Phe Lys Glu Leu Val Tyr Glu Thr Cys
1               5                  10                  15

Arg Val Pro Gly Ala Ala His His Ala Asp Ser Leu Cys Thr Tyr Pro
            20                  25                  30

Val Ala Thr Gln Ala His Ala Gly Lys
        35                  40

<210> SEQ ID NO 33
<211> LENGTH: 5
<212> TYPE: PRT
<213> ORGANISM: Artificial Sequence
<220> FEATURE:
<223> OTHER INFORMATION: FSH fragment

<400> SEQUENCE: 33

Ala His Ala Gly Lys
1               5

<210> SEQ ID NO 34
<211> LENGTH: 5
<212> TYPE: PRT
<213> ORGANISM: Artificial Sequence
<220> FEATURE:
<223> OTHER INFORMATION: FSH fragment

<400> SEQUENCE: 34

Cys His Cys Gly Lys
1               5

<210> SEQ ID NO 35
<211> LENGTH: 38
<212> TYPE: PRT
<213> ORGANISM: Artificial Sequence
<220> FEATURE:
<223> OTHER INFORMATION: hCG peptidomimetic

<400> SEQUENCE: 35

Val Val Ala Asn Tyr Arg Asp Val Arg Phe Glu Ser Cys Arg Leu Pro
1               5                  10                  15

Gly Ala Pro Arg Gly Val Asn Pro Val Cys Ser Tyr Ala Val Ala Leu
            20                  25                  30

Ser Ala Gln Ala Ala Leu
        35

<210> SEQ ID NO 36
<211> LENGTH: 32
<212> TYPE: PRT
<213> ORGANISM: Artificial Sequence
<220> FEATURE:
<223> OTHER INFORMATION: hCG peptidomimetic

<400> SEQUENCE: 36

Asn Tyr Arg Asp Val Arg Phe Glu Ser Cys Arg Leu Pro Gly Ala Pro
1               5                  10                  15

Arg Gly Val Asn Pro Val Cys Ser Tyr Ala Val Ala Leu Ser Ala Gln
            20                  25                  30

<210> SEQ ID NO 37
<211> LENGTH: 32
<212> TYPE: PRT
<213> ORGANISM: Artificial Sequence
<220> FEATURE:
```

<223> OTHER INFORMATION: FSH peptidomimetic

<400> SEQUENCE: 37

Thr Phe Lys Cys Leu Val Tyr Glu Thr Val Arg Val Pro Gly Ala Ala
1               5                   10                  15

His His Ala Asp Ser Leu Tyr Thr Tyr Pro Val Ala Cys Gln Ala His
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: FSH peptidomimetic

<400> SEQUENCE: 38

Thr Phe Lys Glu Leu Val Tyr Glu Thr Cys Arg Val Pro Gly Asp Ala
1               5                   10                  15

His His Ala Asp Ser Leu Cys Thr Tyr Pro Val Ala Thr Gln Ala His
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: FSH peptidomimetic

<400> SEQUENCE: 39

Thr Phe Lys Glu Leu Val Tyr Glu Thr Cys Arg Val Pro Gly Ala Ala
1               5                   10                  15

His His Ala Asp Ser Leu Cys Thr Tyr Pro Val Ala Thr Gln Ala His
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: FSH peptidomimetic

<400> SEQUENCE: 40

Thr Phe Lys Glu Leu Val Tyr Glu Thr Cys Arg Val Pro Gly Asp Ala
1               5                   10                  15

His His Ala Asp Lys Leu Cys Thr Tyr Pro Val Ala Thr Gln Ala His
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: FSH peptidomimetic

<400> SEQUENCE: 41

Thr Phe Lys Glu Leu Val Tyr Glu Thr Cys Arg Val Pro Gly Asp Ala
1               5                   10                  15

His Lys Ala Asp Ser Leu Cys Thr Tyr Pro Val Ala Thr Gln Ala His
            20                  25                  30

<210> SEQ ID NO 42
<211> LENGTH: 27
<212> TYPE: PRT
<213> ORGANISM: Artificial Sequence

```
<220> FEATURE:
<223> OTHER INFORMATION: VEGF peptidomimetic

<400> SEQUENCE: 42

Glu Ser Asn Cys Thr Met Gln Ile Met Arg Ile Lys Pro His Gln Gly
1               5                   10                  15

Gln His Ile Gly Glu Met Ser Cys Leu Gln His
            20                  25

<210> SEQ ID NO 43
<211> LENGTH: 29
<212> TYPE: PRT
<213> ORGANISM: Artificial Sequence
<220> FEATURE:
<223> OTHER INFORMATION: VEGF peptidomimetic

<400> SEQUENCE: 43

Glu Glu Ser Asn Cys Thr Met Gln Ile Met Arg Ile Lys Pro His Gln
1               5                   10                  15

Gly Gln His Ile Gly Glu Met Ser Cys Leu Gln His Asn
            20                  25

<210> SEQ ID NO 44
<211> LENGTH: 32
<212> TYPE: PRT
<213> ORGANISM: Artificial Sequence
<220> FEATURE:
<223> OTHER INFORMATION: hCG peptidomimetic
<220> FEATURE:
<221> NAME/KEY: DISULFID
<222> LOCATION: (15)..(15)

<400> SEQUENCE: 44

Asn Tyr Arg Asp Val Arg Phe Glu Ser Cys Arg Leu Pro Gly Cys Pro
1               5                   10                  15

Arg Gly Val Asn Pro Val Cys Ser Tyr Ala Val Ala Leu Ser Ala Gln
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Synthetic construct

<400> SEQUENCE: 45

Thr Phe Lys Glu Leu Val Tyr Glu Thr Cys Arg Val Pro Gly Ala Ala
1               5                   10                  15

His His Ala Asp Ser Leu Cys Thr Tyr Pro Val Ala Thr Gln Ala His
            20                  25                  30

<210> SEQ ID NO 46
<211> LENGTH: 41
<212> TYPE: PRT
<213> ORGANISM: Artificial Sequence
<220> FEATURE:
<223> OTHER INFORMATION: Synthetic construct

<400> SEQUENCE: 46

Lys Ile Gln Lys Thr Ala Thr Phe Lys Glu Leu Val Tyr Glu Thr Cys
1               5                   10                  15

Arg Val Pro Gly Ala Ala His His Ala Asp Ser Leu Cys Thr Tyr Pro
            20                  25                  30

Val Ala Thr Gln Ala His Ala Gly Lys
```

```
                       35                  40

<210> SEQ ID NO 47
<211> LENGTH: 29
<212> TYPE: PRT
<213> ORGANISM: Artificial Sequence
<220> FEATURE:
<223> OTHER INFORMATION: Synthetic construct

<400> SEQUENCE: 47

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala
            20                  25

<210> SEQ ID NO 48
<211> LENGTH: 24
<212> TYPE: PRT
<213> ORGANISM: Artificial Sequence
<220> FEATURE:
<223> OTHER INFORMATION: Synthetic construct

<400> SEQUENCE: 48

Pro Phe Trp Ala His Tyr Ala Ala Ala Gln Trp Asp Phe Gly Asn Thr
1               5                   10                  15

Met Cys Gln Leu Leu Thr Gly Leu
            20

<210> SEQ ID NO 49
<211> LENGTH: 30
<212> TYPE: PRT
<213> ORGANISM: Artificial Sequence
<220> FEATURE:
<223> OTHER INFORMATION: Synthetic construct

<400> SEQUENCE: 49

Ile Phe Thr Arg Ser Gln Lys Glu Gly Leu His Tyr Thr Cys Ser Ser
1               5                   10                  15

His Phe Pro Tyr Ser Gln Tyr Gln Phe Trp Lys Asn Phe Gln
            20                  25                  30

<210> SEQ ID NO 50
<211> LENGTH: 22
<212> TYPE: PRT
<213> ORGANISM: Artificial Sequence
<220> FEATURE:
<223> OTHER INFORMATION: Synthetic construct

<400> SEQUENCE: 50

Asn Thr Phe Gln Glu Phe Phe Gly Leu Asn Asn Cys Ser Ser Ser Asn
1               5                   10                  15

Arg Leu Asp Gln Ala Met
            20

<210> SEQ ID NO 51
<211> LENGTH: 11
<212> TYPE: PRT
<213> ORGANISM: Artificial Sequence
<220> FEATURE:
<223> OTHER INFORMATION: Synthetic construct

<400> SEQUENCE: 51

Thr Arg Ser Gln Lys Glu Gly Leu His Tyr Thr
1               5                   10
```

```
<210> SEQ ID NO 52
<211> LENGTH: 13
<212> TYPE: PRT
<213> ORGANISM: Artificial Sequence
<220> FEATURE:
<223> OTHER INFORMATION: Synthetic construct

<400> SEQUENCE: 52

Ser Ser His Phe Pro Tyr Ser Gln Tyr Gln Phe Trp Lys
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Synthetic construct

<400> SEQUENCE: 53

Gln Glu Phe Phe Gly Leu Asn Asn
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic construct

<400> SEQUENCE: 54

Ser Ser Ser Asn Arg Leu Asp Gln
1               5

<210> SEQ ID NO 55
<211> LENGTH: 29
<212> TYPE: PRT
<213> ORGANISM: Artificial Sequence
<220> FEATURE:
<223> OTHER INFORMATION: Synthetic construct

<400> SEQUENCE: 55

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala
            20                  25

<210> SEQ ID NO 56
<211> LENGTH: 26
<212> TYPE: PRT
<213> ORGANISM: Artificial Sequence
<220> FEATURE:
<223> OTHER INFORMATION: Synthetic construct

<400> SEQUENCE: 56

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys
            20                  25

<210> SEQ ID NO 57
<211> LENGTH: 24
<212> TYPE: PRT
<213> ORGANISM: Artificial Sequence
<220> FEATURE:
<223> OTHER INFORMATION: Synthetic construct
```

```
<400> SEQUENCE: 57

Pro Phe Trp Ala His Tyr Ala Ala Ala Gln Trp Asp Phe Gly Asn Thr
1               5                   10                  15

Met Cys Gln Leu Leu Thr Gly Leu
            20

<210> SEQ ID NO 58
<211> LENGTH: 30
<212> TYPE: PRT
<213> ORGANISM: Artificial Sequence
<220> FEATURE:
<223> OTHER INFORMATION: Synthetic construct

<400> SEQUENCE: 58

Ile Phe Thr Arg Ser Gln Lys Glu Gly Leu His Tyr Thr Cys Ser Ser
1               5                   10                  15

His Phe Pro Tyr Ser Gln Tyr Gln Phe Trp Lys Asn Phe Gln
            20                  25                  30

<210> SEQ ID NO 59
<211> LENGTH: 22
<212> TYPE: PRT
<213> ORGANISM: Artificial Sequence
<220> FEATURE:
<223> OTHER INFORMATION: Synthetic construct

<400> SEQUENCE: 59

Asn Thr Phe Gln Glu Phe Phe Gly Leu Asn Asn Cys Ser Ser Ser Asn
1               5                   10                  15

Arg Leu Asp Gln Ala Met
            20

<210> SEQ ID NO 60
<211> LENGTH: 26
<212> TYPE: PRT
<213> ORGANISM: Artificial Sequence
<220> FEATURE:
<223> OTHER INFORMATION: Synthetic construct

<400> SEQUENCE: 60

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys
            20                  25

<210> SEQ ID NO 61
<211> LENGTH: 11
<212> TYPE: PRT
<213> ORGANISM: Artificial Sequence
<220> FEATURE:
<223> OTHER INFORMATION: Synthetic construct

<400> SEQUENCE: 61

Ala Ala Ala Gln Trp Asp Phe Gly Asn Thr Met
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic construct

<400> SEQUENCE: 62
```

```
Arg Ser Gln Lys Glu Gly Leu His Tyr Thr
1               5                   10
```

<210> SEQ ID NO 63
<211> LENGTH: 13
<212> TYPE: PRT
<213> ORGANISM: Artificial Sequence
<220> FEATURE:
<223> OTHER INFORMATION: Synthetic construct

<400> SEQUENCE: 63

```
Ser Ser His Phe Pro Tyr Ser Gln Tyr Gln Phe Trp Lys
1               5                   10
```

<210> SEQ ID NO 64
<211> LENGTH: 16
<212> TYPE: PRT
<213> ORGANISM: Artificial Sequence
<220> FEATURE:
<223> OTHER INFORMATION: Synthetic construct

<400> SEQUENCE: 64

```
Gln Glu Phe Phe Gly Leu Asn Asn Cys Ser Ser Ser Asn Arg Leu Asp
1               5                   10                  15
```

<210> SEQ ID NO 65
<211> LENGTH: 26
<212> TYPE: PRT
<213> ORGANISM: Artificial Sequence
<220> FEATURE:
<223> OTHER INFORMATION: Synthetic construct

<400> SEQUENCE: 65

```
Met Asp Tyr Gln Val Ser Ser Pro Ile Tyr Asp Ile Asn Tyr Tyr Thr
1               5                   10                  15

Ser Glu Pro Ala Gln Lys Ile Asn Val Lys
            20                  25
```

<210> SEQ ID NO 66
<211> LENGTH: 28
<212> TYPE: PRT
<213> ORGANISM: Artificial Sequence
<220> FEATURE:
<223> OTHER INFORMATION: Synthetic construct

<400> SEQUENCE: 66

```
Met Asp Tyr Gln Val Ser Ser Pro Ile Tyr Asp Ile Asn Tyr Tyr Thr
1               5                   10                  15

Ser Glu Pro Ala Gly Ser Ser Ser Asn Arg Leu Asp
            20                  25
```

<210> SEQ ID NO 67
<211> LENGTH: 19
<212> TYPE: PRT
<213> ORGANISM: Artificial Sequence
<220> FEATURE:
<223> OTHER INFORMATION: Synthetic construct

<400> SEQUENCE: 67

```
Gln Lys Ile Asn Val Lys Gly Gly Ala Ala Ala Gln Trp Asp Phe Gly
1               5                   10                  15

Asn Thr Met
```

<210> SEQ ID NO 68
<211> LENGTH: 17

```
<212> TYPE: PRT
<213> ORGANISM: Artificial Sequence
<220> FEATURE:
<223> OTHER INFORMATION: Synthetic construct

<400> SEQUENCE: 68

Gln Lys Ile Asn Val Lys Gly Gly Gln Glu Phe Phe Gly Leu Asn Asn
1               5                   10                  15

Cys

<210> SEQ ID NO 69
<211> LENGTH: 25
<212> TYPE: PRT
<213> ORGANISM: Artificial Sequence
<220> FEATURE:
<223> OTHER INFORMATION: Synthetic construct

<400> SEQUENCE: 69

Ala Ala Ala Gln Trp Asp Phe Gly Asn Thr Met Gly Gly Gly Arg Ser
1               5                   10                  15

Gln Lys Glu Gly Leu His Tyr Thr Cys
            20                  25

<210> SEQ ID NO 70
<211> LENGTH: 27
<212> TYPE: PRT
<213> ORGANISM: Artificial Sequence
<220> FEATURE:
<223> OTHER INFORMATION: Synthetic construct

<400> SEQUENCE: 70

Ala Ala Ala Gln Trp Asp Phe Gly Asn Thr Met Gly Gly Gly Ser Ser
1               5                   10                  15

His Phe Pro Tyr Ser Gln Tyr Gln Phe Trp Lys
            20                  25

<210> SEQ ID NO 71
<211> LENGTH: 24
<212> TYPE: PRT
<213> ORGANISM: Artificial Sequence
<220> FEATURE:
<223> OTHER INFORMATION: Synthetic construct

<400> SEQUENCE: 71

Ala Ala Ala Gln Trp Asp Phe Gly Asn Thr Met Gly Gly Gly Gly Gln
1               5                   10                  15

Glu Phe Phe Gly Leu Asn Asn Cys
            20

<210> SEQ ID NO 72
<211> LENGTH: 24
<212> TYPE: PRT
<213> ORGANISM: Artificial Sequence
<220> FEATURE:
<223> OTHER INFORMATION: Synthetic construct

<400> SEQUENCE: 72

Arg Ser Gln Lys Glu Gly Leu His Tyr Thr Ala Ser Ser His Phe Pro
1               5                   10                  15

Tyr Ser Gln Tyr Gln Phe Trp Lys
            20

<210> SEQ ID NO 73
<211> LENGTH: 29
```

```
<212> TYPE: PRT
<213> ORGANISM: Artificial Sequence
<220> FEATURE:
<223> OTHER INFORMATION: Synthetic construct

<400> SEQUENCE: 73

Cys Ser Ser His Phe Pro Tyr Ser Gln Tyr Gln Phe Trp Lys Gly Gly
1               5                   10                  15

Gly Ala Ala Ala Gln Trp Asp Phe Gly Asn Thr Met Cys
            20                  25

<210> SEQ ID NO 74
<211> LENGTH: 32
<212> TYPE: PRT
<213> ORGANISM: Artificial Sequence
<220> FEATURE:
<223> OTHER INFORMATION: Synthetic construct

<400> SEQUENCE: 74

Cys Ser Ser His Phe Pro Tyr Ser Gln Tyr Gln Phe Trp Lys Gly Gly
1               5                   10                  15

Gln Glu Phe Phe Gly Leu Asn Asn Ala Ser Ser Ser Asn Arg Leu Asp
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Synthetic construct

<400> SEQUENCE: 75

Gln Glu Phe Phe Gly Leu Asn Asn Ala Ser Ser Ser Asn Arg Leu Asp
1               5                   10                  15

Gly Gly Gly Ala Ala Ala Gln Trp Asp Phe Gly Asn Thr Met
            20                  25                  30

<210> SEQ ID NO 76
<211> LENGTH: 28
<212> TYPE: PRT
<213> ORGANISM: Artificial Sequence
<220> FEATURE:
<223> OTHER INFORMATION: Synthetic construct

<400> SEQUENCE: 76

Met Asp Tyr Gln Val Ser Ser Pro Ile Tyr Asp Ile Asn Tyr Tyr Thr
1               5                   10                  15

Ser Glu Cys Gly Cys Ser Ser Ser Asn Arg Leu Asp
            20                  25

<210> SEQ ID NO 77
<211> LENGTH: 32
<212> TYPE: PRT
<213> ORGANISM: Artificial Sequence
<220> FEATURE:
<223> OTHER INFORMATION: Synthetic construct

<400> SEQUENCE: 77

Asp Tyr Gln Val Ser Ser Pro Ile Tyr Asp Ile Asn Tyr Tyr Thr Ser
1               5                   10                  15

Glu Pro Cys Gly Cys Ser Ser Ser Asn Arg Leu Asp Gln Ala Met Gln
            20                  25                  30

<210> SEQ ID NO 78
```

-continued

```
<211> LENGTH: 21
<212> TYPE: PRT
<213> ORGANISM: Artificial Sequence
<220> FEATURE:
<223> OTHER INFORMATION: Synthetic construct

<400> SEQUENCE: 78

Gln Lys Ile Asn Val Lys Gly Gly Cys Ala Ala Ala Gln Trp Asp Phe
1               5                   10                  15

Gly Asn Thr Met Cys
            20

<210> SEQ ID NO 79
<211> LENGTH: 11
<212> TYPE: PRT
<213> ORGANISM: Artificial Sequence
<220> FEATURE:
<223> OTHER INFORMATION: Synthetic construct

<400> SEQUENCE: 79

Ala Ala Ala Gln Trp Asp Phe Gly Asn Thr Met
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Synthetic construct

<400> SEQUENCE: 80

Ser Gln Lys Glu Gly Leu His Tyr Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic construct

<400> SEQUENCE: 81

Ala Gln Trp Asp Phe Gly Asn
1               5

<210> SEQ ID NO 82
<211> LENGTH: 14
<212> TYPE: PRT
<213> ORGANISM: Artificial Sequence
<220> FEATURE:
<223> OTHER INFORMATION: Synthetic construct

<400> SEQUENCE: 82

Ser Ser His Phe Pro Tyr Ser Gln Tyr Gln Phe Trp Lys Asn
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic construct

<400> SEQUENCE: 83

His Tyr Ala Ala Ala Gln Trp Asp Phe Gly Asn Thr Met
1               5                   10
```

```
<210> SEQ ID NO 84
<211> LENGTH: 14
<212> TYPE: PRT
<213> ORGANISM: Artificial Sequence
<220> FEATURE:
<223> OTHER INFORMATION: Synthetic construct

<400> SEQUENCE: 84

Ser Ser His Phe Pro Tyr Ser Gln Tyr Gln Phe Trp Lys Asn
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic construct

<400> SEQUENCE: 85

Ser Glu Pro Cys Gln Lys Ile Asn Val Lys
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetic construct

<400> SEQUENCE: 86

Gln Glu Phe Phe Gly Leu Asn Asn Cys Ser Ser Ser Asn
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthetic construct

<400> SEQUENCE: 87

Ala Ala Ala Gln Trp Asp Phe Gly Asn Thr Met
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic construct

<400> SEQUENCE: 88

Arg Ser Gln Lys Glu Gly Leu His Tyr Thr
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Synthetic construct

<400> SEQUENCE: 89

Ala Gln Trp Asp Phe Gly Asn Thr Met
1               5
```

```
<210> SEQ ID NO 90
<211> LENGTH: 15
<212> TYPE: PRT
<213> ORGANISM: Artificial Sequence
<220> FEATURE:
<223> OTHER INFORMATION: Synthetic construct

<400> SEQUENCE: 90

Ser Ser His Phe Pro Tyr Ser Gln Tyr Gln Phe Trp Lys Asn Phe
1               5                   10                  15

<210> SEQ ID NO 91
<211> LENGTH: 17
<212> TYPE: PRT
<213> ORGANISM: Artificial Sequence
<220> FEATURE:
<223> OTHER INFORMATION: Synthetic construct

<400> SEQUENCE: 91

Gln Glu Phe Phe Gly Leu Asn Asn Ala Ser Ser Ser Asn Arg Leu Asp
1               5                   10                  15

Gln

<210> SEQ ID NO 92
<211> LENGTH: 12
<212> TYPE: PRT
<213> ORGANISM: Artificial Sequence
<220> FEATURE:
<223> OTHER INFORMATION: Synthetic construct

<400> SEQUENCE: 92

Tyr Ala Ala Ala Gln Trp Asp Phe Gly Asn Thr Met
1               5                   10

<210> SEQ ID NO 93
<211> LENGTH: 37
<212> TYPE: PRT
<213> ORGANISM: Artificial Sequence
<220> FEATURE:
<223> OTHER INFORMATION: Synthetic construct

<400> SEQUENCE: 93

Ser Leu Pro Gly Ile Ile Phe Thr Arg Ser Gln Lys Glu Gly Leu His
1               5                   10                  15

Tyr Thr Cys Ser Ser His Phe Pro Tyr Ser Gln Tyr Gln Phe Trp Lys
                20                  25                  30

Asn Phe Gln Thr Leu
                35

<210> SEQ ID NO 94
<211> LENGTH: 37
<212> TYPE: PRT
<213> ORGANISM: Artificial Sequence
<220> FEATURE:
<223> OTHER INFORMATION: Synthetic construct

<400> SEQUENCE: 94

Asp Tyr Gln Val Ser Ser Pro Ile Tyr Asp Ile Asn Tyr Tyr Thr Ser
1               5                   10                  15

Glu Pro Cys Gln Lys Ile Asn Val Lys Gln Ile Ala Ala Arg Leu Leu
                20                  25                  30

Pro Pro Leu Tyr Ser
                35
```

```
<210> SEQ ID NO 95
<211> LENGTH: 21
<212> TYPE: PRT
<213> ORGANISM: Artificial Sequence
<220> FEATURE:
<223> OTHER INFORMATION: Synthetic construct

<400> SEQUENCE: 95

Met Asp Tyr Gln Val Ser Ser Pro Ile Tyr Asp Ile Asn Tyr Tyr Thr
1               5                   10                  15

Ser Glu Pro Cys Gln
            20

<210> SEQ ID NO 96
<211> LENGTH: 21
<212> TYPE: PRT
<213> ORGANISM: Artificial Sequence
<220> FEATURE:
<223> OTHER INFORMATION: Synthetic construct

<400> SEQUENCE: 96

Asp Tyr Gln Val Ser Ser Pro Ile Tyr Asp Ile Asn Tyr Tyr Thr Ser
1               5                   10                  15

Glu Pro Cys Gln Lys
            20

<210> SEQ ID NO 97
<211> LENGTH: 21
<212> TYPE: PRT
<213> ORGANISM: Artificial Sequence
<220> FEATURE:
<223> OTHER INFORMATION: Synthetic construct

<400> SEQUENCE: 97

Tyr Gln Val Ser Ser Pro Ile Tyr Asp Ile Asn Tyr Tyr Thr Ser Glu
1               5                   10                  15

Pro Cys Gln Lys Ile
            20

<210> SEQ ID NO 98
<211> LENGTH: 18
<212> TYPE: PRT
<213> ORGANISM: Artificial Sequence
<220> FEATURE:
<223> OTHER INFORMATION: Synthetic construct

<400> SEQUENCE: 98

Met Asp Tyr Gln Val Ser Ser Pro Ile Tyr Asp Ile Asn Tyr Tyr Thr
1               5                   10                  15

Ser Glu

<210> SEQ ID NO 99
<211> LENGTH: 18
<212> TYPE: PRT
<213> ORGANISM: Artificial Sequence
<220> FEATURE:
<223> OTHER INFORMATION: Synthetic construct

<400> SEQUENCE: 99

Asp Tyr Gln Val Ser Ser Pro Ile Tyr Asp Ile Asn Tyr Tyr Thr Ser
1               5                   10                  15

Glu Pro

<210> SEQ ID NO 100
```

```
<211> LENGTH: 18
<212> TYPE: PRT
<213> ORGANISM: Artificial Sequence
<220> FEATURE:
<223> OTHER INFORMATION: Synthetic construct

<400> SEQUENCE: 100

Tyr Gln Val Ser Ser Pro Ile Tyr Asp Ile Asn Tyr Tyr Thr Ser Glu
1               5                   10                  15
Pro Cys

<210> SEQ ID NO 101
<211> LENGTH: 10
<212> TYPE: PRT
<213> ORGANISM: Artificial Sequence
<220> FEATURE:
<223> OTHER INFORMATION: Synthetic construct

<400> SEQUENCE: 101

Cys Gln Lys Glu Gly Leu His Tyr Thr Cys
1               5                   10

<210> SEQ ID NO 102
<211> LENGTH: 9
<212> TYPE: PRT
<213> ORGANISM: Artificial Sequence
<220> FEATURE:
<223> OTHER INFORMATION: Synthetic construct

<400> SEQUENCE: 102

Cys Gln Lys Glu Gly Leu His Tyr Cys
1               5

<210> SEQ ID NO 103
<211> LENGTH: 11
<212> TYPE: PRT
<213> ORGANISM: Artificial Sequence
<220> FEATURE:
<223> OTHER INFORMATION: Synthetic construct

<400> SEQUENCE: 103

Cys Ser Gln Lys Glu Gly Leu His Tyr Thr Cys
1               5                   10

<210> SEQ ID NO 104
<211> LENGTH: 18
<212> TYPE: PRT
<213> ORGANISM: Artificial Sequence
<220> FEATURE:
<223> OTHER INFORMATION: Synthetic construct

<400> SEQUENCE: 104

Cys Trp Asp Phe Gly Asn Thr Met Cys Gln Lys Glu Gly Leu His Tyr
1               5                   10                  15
Thr Cys

<210> SEQ ID NO 105
<211> LENGTH: 12
<212> TYPE: PRT
<213> ORGANISM: Artificial Sequence
<220> FEATURE:
<223> OTHER INFORMATION: Synthetic construct

<400> SEQUENCE: 105

Cys Arg Ser Gln Lys Glu Gly Leu His Tyr Thr Cys
1               5                   10
```

<210> SEQ ID NO 106
<211> LENGTH: 18
<212> TYPE: PRT
<213> ORGANISM: Artificial Sequence
<220> FEATURE:
<223> OTHER INFORMATION: Synthetic construct

<400> SEQUENCE: 106

Cys Asn Thr Met Gly Gly Gly Arg Ser Gln Lys Glu Gly Leu His Tyr
1               5                   10                  15
Thr Cys

<210> SEQ ID NO 107
<211> LENGTH: 18
<212> TYPE: PRT
<213> ORGANISM: Artificial Sequence
<220> FEATURE:
<223> OTHER INFORMATION: Synthetic construct

<400> SEQUENCE: 107

Cys Gln Trp Asp Phe Gly Asn Thr Cys Gln Lys Glu Gly Leu His Tyr
1               5                   10                  15
Thr Cys

<210> SEQ ID NO 108
<211> LENGTH: 20
<212> TYPE: PRT
<213> ORGANISM: Artificial Sequence
<220> FEATURE:
<223> OTHER INFORMATION: Synthetic construct

<400> SEQUENCE: 108

Cys Phe Gly Asn Thr Met Gly Gly Gly Arg Ser Gln Lys Glu Gly Leu
1               5                   10                  15
His Tyr Thr Cys
            20

<210> SEQ ID NO 109
<211> LENGTH: 18
<212> TYPE: PRT
<213> ORGANISM: Artificial Sequence
<220> FEATURE:
<223> OTHER INFORMATION: Synthetic construct

<400> SEQUENCE: 109

Cys Ala Gln Trp Asp Phe Gly Asn Cys Gln Lys Glu Gly Leu His Tyr
1               5                   10                  15
Thr Cys

<210> SEQ ID NO 110
<211> LENGTH: 17
<212> TYPE: PRT
<213> ORGANISM: Artificial Sequence
<220> FEATURE:
<223> OTHER INFORMATION: Synthetic construct

<400> SEQUENCE: 110

Lys Lys Lys Ser Gly Glu Glu Arg Arg Arg Val Asn Gln Phe Leu Asp
1               5                   10                  15
Tyr

<210> SEQ ID NO 111

```
<211> LENGTH: 17
<212> TYPE: PRT
<213> ORGANISM: Artificial Sequence
<220> FEATURE:
<223> OTHER INFORMATION: Synthetic construct

<400> SEQUENCE: 111

Leu Ile Ala Asn Glu Thr Leu Arg Ile Pro Val Pro Val His Lys Asn
1               5                   10                  15

His

<210> SEQ ID NO 112
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 112

Cys Glu Glu Arg Arg Arg Val Cys Ala Asn Glu Thr Leu Arg Ile Pro
1               5                   10                  15

Val Pro Cys Gly Ser Cys
            20

<210> SEQ ID NO 113
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 113

Cys Ser Gly Glu Glu Arg Arg Arg Val Cys Ala Asn Glu Thr Leu Arg
1               5                   10                  15

Ile Pro Cys Gly Ser Cys
            20

<210> SEQ ID NO 114
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 114

Cys Glu Glu Arg Arg Arg Val Asn Gln Cys Ala Asn Glu Thr Leu Arg
1               5                   10                  15

Ile Pro Cys Gly Ser Cys
            20

<210> SEQ ID NO 115
<211> LENGTH: 21
<212> TYPE: PRT
<213> ORGANISM: Artificial Sequence
<220> FEATURE:
```

```
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 115

Cys Gly Glu Glu Arg Arg Cys Ile Ala Asn Glu Thr Leu Arg Ile
1               5                   10                  15

Pro Cys Gly Ser Cys
            20

<210> SEQ ID NO 116
<211> LENGTH: 14
<212> TYPE: PRT
<213> ORGANISM: Artificial Sequence
<220> FEATURE:
<223> OTHER INFORMATION: Synthetic construct

<400> SEQUENCE: 116

Cys Arg Val Pro Gly Asp Ala His His Ala Asp Ser Leu Cys
1               5                   10

<210> SEQ ID NO 117
<211> LENGTH: 16
<212> TYPE: PRT
<213> ORGANISM: Artificial Sequence
<220> FEATURE:
<223> OTHER INFORMATION: Synthetic construct

<400> SEQUENCE: 117

Cys Val Arg Val Pro Gly Ala Ala His His Ala Asp Ser Leu Tyr Cys
1               5                   10                  15

<210> SEQ ID NO 118
<211> LENGTH: 20
<212> TYPE: PRT
<213> ORGANISM: Artificial Sequence
<220> FEATURE:
<223> OTHER INFORMATION: Synthetic construct

<400> SEQUENCE: 118

Tyr Glu Thr Cys Arg Val Pro Gly Asp Ala His His Ala Asp Ser Leu
1               5                   10                  15

Cys Thr Tyr Pro
            20

<210> SEQ ID NO 119
<211> LENGTH: 32
<212> TYPE: PRT
<213> ORGANISM: Artificial Sequence
<220> FEATURE:
<223> OTHER INFORMATION: Synthetic construct

<400> SEQUENCE: 119

Thr Phe Lys Glu Leu Val Tyr Glu Thr Cys Arg Val Pro Gly Ala Ala
1               5                   10                  15

His His Ala Asp Ser Leu Cys Thr Tyr Pro Val Ala Thr Gln Ala His
            20                  25                  30

<210> SEQ ID NO 120
<211> LENGTH: 41
<212> TYPE: PRT
<213> ORGANISM: Artificial Sequence
<220> FEATURE:
<223> OTHER INFORMATION: Synthetic construct
```

```
<400> SEQUENCE: 120

Lys Ile Gln Lys Thr Ala Thr Phe Lys Glu Leu Val Tyr Glu Thr Cys
1               5                  10                  15

Arg Val Pro Gly Ala Ala His His Ala Asp Ser Leu Cys Thr Tyr Pro
            20                  25                  30

Val Ala Thr Gln Ala His Ala Gly Lys
        35                  40

<210> SEQ ID NO 121
<211> LENGTH: 20
<212> TYPE: PRT
<213> ORGANISM: Artificial Sequence
<220> FEATURE:
<223> OTHER INFORMATION: Synthetic construct

<400> SEQUENCE: 121

Cys Tyr Thr Arg Asp Leu Val Tyr Lys Asp Pro Ala Arg Pro Lys Ile
1               5                  10                  15

Gln Lys Thr Cys
            20

<210> SEQ ID NO 122
<211> LENGTH: 15
<212> TYPE: PRT
<213> ORGANISM: Artificial Sequence
<220> FEATURE:
<223> OTHER INFORMATION: Synthetic construct

<400> SEQUENCE: 122

Thr Gln Ala His Cys Gly Lys Ala Asp Ser Asp Ser Thr Asp Cys
1               5                  10                  15

<210> SEQ ID NO 123
<211> LENGTH: 32
<212> TYPE: PRT
<213> ORGANISM: Artificial Sequence
<220> FEATURE:
<223> OTHER INFORMATION: Synthetic construct

<400> SEQUENCE: 123

Thr Phe Lys Glu Leu Val Tyr Glu Thr Val Arg Val Pro Gly Cys Ala
1               5                  10                  15

His His Ala Asp Ser Leu Tyr Thr Tyr Pro Val Ala Thr Gln Ala His
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Synthetic construct

<400> SEQUENCE: 124

Thr Phe Lys Glu Leu Val Tyr Glu Thr Cys Arg Val Pro Gly Asp Ala
1               5                  10                  15

His His Ala Asp Ser Leu Cys Thr Tyr Pro Val Ala Thr Gln Ala His
            20                  25                  30

<210> SEQ ID NO 125
<211> LENGTH: 32
<212> TYPE: PRT
<213> ORGANISM: Artificial Sequence
<220> FEATURE:
```

<223> OTHER INFORMATION: Synthetic construct

<400> SEQUENCE: 125

Thr Phe Lys Glu Leu Val Tyr Glu Thr Cys Arg Val Pro Gly Asp Ala
1               5                   10                  15

His His Ala Asp Lys Leu Cys Thr Tyr Pro Val Ala Thr Gln Ala His
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Synthetic construct

<400> SEQUENCE: 126

Asn Tyr Arg Asp Val Arg Phe Glu Ser Cys Arg Leu Pro Gly Ala Pro
1               5                   10                  15

Arg Gly Val Asn Pro Val Cys Ser Tyr Ala Val Ala Leu Ser Ala Gln
            20                  25                  30

<210> SEQ ID NO 127
<211> LENGTH: 32
<212> TYPE: PRT
<213> ORGANISM: Artificial Sequence
<220> FEATURE:
<223> OTHER INFORMATION: Synthetic construct

<400> SEQUENCE: 127

Asn Tyr Arg Asp Val Arg Phe Glu Ser Ile Arg Leu Pro Gly Ala Pro
1               5                   10                  15

Arg Gly Val Asn Pro Val Val Ser Tyr Ala Val Ala Leu Ser Ala Gln
            20                  25                  30

<210> SEQ ID NO 128
<211> LENGTH: 38
<212> TYPE: PRT
<213> ORGANISM: Artificial Sequence
<220> FEATURE:
<223> OTHER INFORMATION: Synthetic construct

<400> SEQUENCE: 128

Val Val Ala Asn Tyr Arg Asp Val Arg Phe Glu Ser Cys Arg Leu Pro
1               5                   10                  15

Gly Ala Pro Arg Gly Val Asn Pro Val Cys Ser Tyr Ala Val Ala Leu
            20                  25                  30

Ser Ala Gln Ala Ala Leu
        35

<210> SEQ ID NO 129
<211> LENGTH: 34
<212> TYPE: PRT
<213> ORGANISM: Artificial Sequence
<220> FEATURE:
<223> OTHER INFORMATION: hCG peptidomimetic

<400> SEQUENCE: 129

Ala Asn Tyr Arg Asp Val Arg Phe Glu Ser Cys Arg Leu Pro Gly Ala
1               5                   10                  15

Pro Arg Gly Val Asn Pro Val Cys Ser Tyr Ala Val Ala Leu Ser Ala
            20                  25                  30

Gln Ala

```
<210> SEQ ID NO 130
<211> LENGTH: 36
<212> TYPE: PRT
<213> ORGANISM: Artificial Sequence
<220> FEATURE:
<223> OTHER INFORMATION: hCG peptidomimetic

<400> SEQUENCE: 130

Val Ala Asn Tyr Arg Asp Val Arg Phe Glu Ser Cys Arg Leu Pro Gly
1               5                   10                  15

Ala Pro Arg Gly Val Asn Pro Val Cys Ser Tyr Ala Val Ala Leu Ser
            20                  25                  30

Ala Gln Ala Ala
        35

<210> SEQ ID NO 131
<211> LENGTH: 32
<212> TYPE: PRT
<213> ORGANISM: Artificial Sequence
<220> FEATURE:
<223> OTHER INFORMATION: hCG peptidomimetic

<400> SEQUENCE: 131

Asn Tyr Arg Asp Val Arg Phe Glu Ser Cys Arg Leu Pro Gly Asp Pro
1               5                   10                  15

Arg Gly Val Asn Pro Val Cys Ser Tyr Ala Val Ala Leu Ser Ala Gln
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: hCG peptidomimetic
<220> FEATURE:
<221> NAME/KEY: DISULFID
<222> LOCATION: (15)..(15)

<400> SEQUENCE: 132

Asn Tyr Arg Asp Val Arg Phe Glu Ser Cys Arg Leu Pro Gly Cys Pro
1               5                   10                  15

Arg Gly Val Asn Pro Val Cys Ser Tyr Ala Val Ala Leu Ser Ala Gln
            20                  25                  30

<210> SEQ ID NO 133
<211> LENGTH: 27
<212> TYPE: PRT
<213> ORGANISM: Artificial Sequence
<220> FEATURE:
<223> OTHER INFORMATION: VEGF peptidomimetic

<400> SEQUENCE: 133

Glu Ser Asn Ile Thr Met Gln Ile Met Arg Ile Lys Pro His Gln Gly
1               5                   10                  15

Gln His Ile Gly Glu Met Ser Phe Leu Gln His
            20                  25

<210> SEQ ID NO 134
<211> LENGTH: 27
<212> TYPE: PRT
<213> ORGANISM: Artificial Sequence
<220> FEATURE:
<223> OTHER INFORMATION: VEGF peptidomimetic

<400> SEQUENCE: 134
```

```
Glu Ser Asn Cys Thr Met Gln Ile Met Arg Ile Lys Pro His Gln Gly
1               5                   10                  15

Gln His Ile Gly Glu Met Ser Cys Leu Gln His
            20                  25

<210> SEQ ID NO 135
<211> LENGTH: 27
<212> TYPE: PRT
<213> ORGANISM: Artificial Sequence
<220> FEATURE:
<223> OTHER INFORMATION: VEGF peptidomimetic

<400> SEQUENCE: 135

Glu Ser Asn Ile Thr Cys Gln Ile Met Arg Ile Lys Pro His Gln Gly
1               5                   10                  15

Gln His Ile Gly Glu Cys Ser Phe Leu Gln His
            20                  25

<210> SEQ ID NO 136
<211> LENGTH: 27
<212> TYPE: PRT
<213> ORGANISM: Artificial Sequence
<220> FEATURE:
<223> OTHER INFORMATION: VEGF peptidomimetic

<400> SEQUENCE: 136

Glu Ser Asn Ile Thr Met Gln Cys Met Arg Ile Lys Pro His Gln Gly
1               5                   10                  15

Gln His Ile Cys Glu Met Ser Phe Leu Gln His
            20                  25

<210> SEQ ID NO 137
<211> LENGTH: 27
<212> TYPE: PRT
<213> ORGANISM: Artificial Sequence
<220> FEATURE:
<223> OTHER INFORMATION: VEGF peptidomimetic

<400> SEQUENCE: 137

Glu Ser Asn Ile Thr Met Gln Ile Cys Arg Ile Lys Pro His Gln Gly
1               5                   10                  15

Gln His Cys Gly Glu Met Ser Phe Leu Gln His
            20                  25

<210> SEQ ID NO 138
<211> LENGTH: 29
<212> TYPE: PRT
<213> ORGANISM: Artificial Sequence
<220> FEATURE:
<223> OTHER INFORMATION: VEGF peptidomimetic

<400> SEQUENCE: 138

Glu Glu Ser Asn Ile Thr Met Gln Ile Met Arg Ile Lys Pro His Gln
1               5                   10                  15

Gly Gln His Ile Gly Glu Met Ser Phe Leu Gln His Asn
            20                  25

<210> SEQ ID NO 139
<211> LENGTH: 29
<212> TYPE: PRT
<213> ORGANISM: Artificial Sequence
<220> FEATURE:
<223> OTHER INFORMATION: VEGF peptidomimetic
```

```
<400> SEQUENCE: 139

Glu Glu Ser Asn Cys Thr Met Gln Ile Met Arg Ile Lys Pro His Gln
1               5                   10                  15

Gly Gln His Ile Gly Glu Met Ser Cys Leu Gln His Asn
            20                  25

<210> SEQ ID NO 140
<211> LENGTH: 29
<212> TYPE: PRT
<213> ORGANISM: Artificial Sequence
<220> FEATURE:
<223> OTHER INFORMATION: VEGF peptidomimetic

<400> SEQUENCE: 140

Glu Glu Ser Asn Ile Thr Cys Gln Ile Met Arg Ile Lys Pro His Gln
1               5                   10                  15

Gly Gln His Ile Gly Glu Cys Ser Phe Leu Gln His Asn
            20                  25

<210> SEQ ID NO 141
<211> LENGTH: 29
<212> TYPE: PRT
<213> ORGANISM: Artificial Sequence
<220> FEATURE:
<223> OTHER INFORMATION: VEGF peptidomimetic

<400> SEQUENCE: 141

Glu Glu Ser Asn Ile Thr Met Gln Cys Met Arg Ile Lys Pro His Gln
1               5                   10                  15

Gly Gln His Ile Cys Glu Met Ser Phe Leu Gln His Asn
            20                  25

<210> SEQ ID NO 142
<211> LENGTH: 29
<212> TYPE: PRT
<213> ORGANISM: Artificial Sequence
<220> FEATURE:
<223> OTHER INFORMATION: VEGF peptidomimetic

<400> SEQUENCE: 142

Glu Glu Ser Asn Ile Thr Met Gln Ile Cys Arg Ile Lys Pro His Gln
1               5                   10                  15

Gly Gln His Cys Gly Glu Met Ser Phe Leu Gln His Asn
            20                  25

<210> SEQ ID NO 143
<211> LENGTH: 91
<212> TYPE: PRT
<213> ORGANISM: Homo Sapiens

<400> SEQUENCE: 143

Pro Asp Val Gln Asp Cys Pro Glu Cys Thr Leu Gln Glu Asn Pro Phe
1               5                   10                  15

Phe Ser Gln Pro Gly Ala Pro Ile Leu Gln Cys Met Gly Cys Cys Phe
            20                  25                  30

Ser Arg Ala Tyr Pro Thr Pro Leu Arg Ser Lys Lys Thr Met Leu Val
        35                  40                  45

Gln Lys Asn Val Thr Ser Glu Ser Thr Cys Cys Val Ala Lys Ser Tyr
    50                  55                  60

Asn Arg Val Thr Val Met Gly Gly Phe Lys Val Glu Asn His Thr Ala
65                  70                  75                  80
```

-continued

```
Cys His Cys Ser Thr Cys Tyr Tyr His Lys Ser
            85                  90

<210> SEQ ID NO 144
<211> LENGTH: 110
<212> TYPE: PRT
<213> ORGANISM: Homo Sapiens

<400> SEQUENCE: 144

Ser Cys Glu Leu Thr Asn Ile Thr Ile Ala Ile Glu Lys Glu Cys
1               5                   10                  15

Arg Phe Cys Ile Ser Ile Asn Thr Thr Trp Cys Ala Gly Tyr Cys Tyr
            20                  25                  30

Thr Arg Asp Leu Val Tyr Lys Asp Pro Ala Arg Pro Lys Ile Gln Lys
            35                  40                  45

Thr Cys Thr Phe Lys Glu Leu Val Tyr Glu Thr Val Arg Val Pro Gly
        50                  55                  60

Cys Ala His His Ala Asp Ser Leu Tyr Thr Tyr Pro Val Ala Thr Gln
65                  70                  75                  80

Cys His Cys Gly Lys Cys Asp Ser Asp Ser Thr Asp Cys Thr Val Arg
                85                  90                  95

Gly Leu Gly Pro Ser Tyr Cys Ser Phe Gly Glu Met Lys Glu
            100                 105                 110

<210> SEQ ID NO 145
<211> LENGTH: 145
<212> TYPE: PRT
<213> ORGANISM: Homo Sapiens

<400> SEQUENCE: 145

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
        50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Ser Lys Ala Pro Pro Pro Ser Leu
            115                 120                 125

Pro Ser Pro Ser Arg Leu Pro Gly Pro Ser Asp Thr Pro Ile Leu Pro
        130                 135                 140

Gln
145

<210> SEQ ID NO 146
<211> LENGTH: 118
<212> TYPE: PRT
<213> ORGANISM: Homo Sapiens

<400> SEQUENCE: 146

Phe Cys Ile Pro Thr Glu Tyr Thr Met His Ile Glu Arg Arg Glu Cys
```

-continued

```
              1               5                  10                 15
Ala Tyr Cys Leu Thr Ile Asn Thr Thr Ile Cys Ala Gly Tyr Cys Met
                20                  25                 30

Thr Arg Asp Ile Asn Gly Lys Leu Phe Leu Pro Lys Tyr Ala Leu Ser
                35                  40                 45

Gln Asp Val Cys Thr Tyr Arg Asp Phe Ile Tyr Arg Thr Val Glu Ile
 50                  55                     60

Pro Gly Cys Pro Leu His Val His Pro Tyr Phe Ser Tyr Pro Val Ala
 65                  70                     75                 80

Leu Ser Cys Lys Cys Gly Lys Cys Asn Thr Asp Tyr Ser Asp Cys Ile
                85                  90                 95

His Glu Ala Ile Lys Thr Asn Tyr Cys Thr Lys Pro Gln Lys Ser Tyr
               100                 105                110

Leu Val Gly Phe Ser Val
               115
```

<210> SEQ ID NO 147
<211> LENGTH: 121
<212> TYPE: PRT
<213> ORGANISM: Homo Sapiens

<400> SEQUENCE: 147

```
Ser Arg Glu Pro Leu Arg Pro Trp Cys His Pro Ile Asn Ala Ile Leu
 1               5                  10                 15

Ala Val Glu Lys Glu Gly Cys Pro Val Cys Ile Thr Val Asn Thr Thr
                20                  25                 30

Ile Cys Ala Gly Tyr Cys Pro Thr Met Met Arg Val Leu Gln Ala Val
                35                  40                 45

Leu Pro Pro Leu Pro Gln Val Val Cys Thr Tyr Arg Asp Val Arg Phe
 50                  55                     60

Glu Ser Ile Arg Leu Pro Gly Cys Pro Arg Gly Val Asp Pro Val Val
 65                  70                     75                 80

Ser Phe Pro Val Ala Leu Ser Cys Arg Cys Gly Pro Cys Arg Arg Ser
                85                  90                 95

Thr Ser Asp Cys Gly Gly Pro Lys Asp His Pro Leu Thr Cys Asp His
               100                 105                110

Pro Gln Leu Ser Gly Leu Leu Phe Leu
               115                 120
```

<210> SEQ ID NO 148
<211> LENGTH: 120
<212> TYPE: PRT
<213> ORGANISM: Homo Sapiens

<400> SEQUENCE: 148

```
Ser Ser Ser His Pro Ile Phe His Arg Gly Glu Phe Ser Val Cys Asp
 1               5                  10                 15

Ser Val Ser Val Trp Val Gly Asp Lys Thr Thr Ala Thr Asp Ile Lys
                20                  25                 30

Gly Lys Glu Val Met Val Leu Gly Glu Val Asn Ile Asn Asn Ser Val
                35                  40                 45

Phe Lys Gln Tyr Phe Phe Glu Thr Lys Cys Arg Asp Pro Asn Pro Val
 50                  55                     60

Asp Ser Gly Cys Arg Gly Ile Asp Ser Lys His Trp Asn Ser Tyr Cys
 65                  70                     75                 80

Thr Thr Thr His Thr Phe Val Lys Ala Leu Thr Met Asp Gly Lys Gln
```

-continued

```
                    85                  90                  95

Ala Ala Trp Arg Phe Ile Arg Ile Asp Thr Ala Cys Val Cys Val Leu
            100                 105                 110

Ser Arg Lys Ala Val Arg Ala
        115                 120

<210> SEQ ID NO 149
<211> LENGTH: 119
<212> TYPE: PRT
<213> ORGANISM: Homo Sapiens

<400> SEQUENCE: 149

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 150
<211> LENGTH: 110
<212> TYPE: PRT
<213> ORGANISM: Homo Sapiens

<400> SEQUENCE: 150

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg
        100                 105                 110

<210> SEQ ID NO 151
<211> LENGTH: 101
<212> TYPE: PRT
<213> ORGANISM: Homo Sapiens

<400> SEQUENCE: 151

Ser Glu Val Glu Val Val Pro Phe Gln Glu Val Trp Gly Arg Ser Tyr
1               5                   10                  15
```

```
Cys Arg Ala Leu Glu Arg Leu Val Asp Val Ser Glu Tyr Pro Ser
            20                  25                  30

Glu Val Glu His Met Phe Ser Pro Ser Cys Val Ser Leu Leu Arg Cys
            35                  40                  45

Thr Gly Cys Cys Gly Asp Glu Asn Leu His Cys Val Pro Val Glu Thr
    50                  55                  60

Ala Asn Val Thr Met Gln Leu Leu Lys Ile Arg Ser Gly Asp Arg Pro
65                  70                  75                  80

Ser Tyr Val Glu Leu Thr Phe Ser Gln His Val Arg Cys Glu Cys Arg
                85                  90                  95

Pro Leu Arg Glu Lys
                100

<210> SEQ ID NO 152
<211> LENGTH: 99
<212> TYPE: PRT
<213> ORGANISM: Homo Sapiens

<400> SEQUENCE: 152

Ser Ile Glu Glu Ala Val Pro Ala Val Cys Lys Thr Arg Thr Val Ile
1               5                   10                  15

Tyr Glu Ile Pro Arg Ser Gln Val Asp Pro Thr Ser Ala Asn Phe Leu
                20                  25                  30

Ile Trp Pro Pro Cys Val Glu Val Lys Arg Cys Thr Gly Cys Cys Asn
            35                  40                  45

Thr Ser Ser Val Lys Cys Gln Pro Ser Arg Val His His Arg Ser Val
    50                  55                  60

Lys Val Ala Lys Val Glu Tyr Val Arg Lys Lys Pro Lys Leu Lys Glu
65                  70                  75                  80

Val Gln Val Arg Leu Glu Glu His Leu Glu Cys Ala Cys Ala Thr Thr
                85                  90                  95

Ser Leu Asn

<210> SEQ ID NO 153
<211> LENGTH: 105
<212> TYPE: PRT
<213> ORGANISM: Homo Sapiens

<400> SEQUENCE: 153

Ser Leu Gly Ser Leu Thr Ile Ala Glu Pro Ala Met Ile Ala Glu Cys
1               5                   10                  15

Lys Thr Arg Thr Glu Val Phe Glu Ile Ser Arg Arg Leu Ile Asp Arg
                20                  25                  30

Thr Asn Ala Asn Phe Leu Val Trp Pro Pro Cys Val Glu Val Gln Arg
            35                  40                  45

Cys Ser Gly Cys Cys Asn Asn Arg Asn Val Gln Cys Arg Pro Thr Gln
    50                  55                  60

Val Gln Leu Arg Pro Val Gln Val Arg Lys Ile Glu Ile Val Arg Lys
65                  70                  75                  80

Lys Pro Ile Phe Lys Lys Ala Thr Val Thr Leu Glu Asp His Leu Ala
                85                  90                  95

Cys Lys Cys Glu Thr Val Ala Ala Ala
                100                 105

<210> SEQ ID NO 154
<211> LENGTH: 112
```

```
<212> TYPE: PRT
<213> ORGANISM: Homo Sapiens

<400> SEQUENCE: 154

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 155
<211> LENGTH: 114
<212> TYPE: PRT
<213> ORGANISM: Homo Sapiens

<400> SEQUENCE: 155

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 156
<211> LENGTH: 139
<212> TYPE: PRT
<213> ORGANISM: Homo Sapiens

<400> SEQUENCE: 156

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
50                  55                  60

Tyr Tyr Cys Glu Gly Glu Cys Ala Phe Pro Leu Asn Ser Tyr Met Asn
65                  70                  75                  80
```

```
Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
        115                 120                 125

Arg Asn Met Val Val Arg Ala Cys Gly Cys His
    130                 135

<210> SEQ ID NO 157
<211> LENGTH: 108
<212> TYPE: PRT
<213> ORGANISM: Homo Sapiens

<400> SEQUENCE: 157

Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
            20                  25                  30

Ala Tyr Glu Cys Arg Gly Val Cys Asn Tyr Pro Leu Ala Glu His Leu
        35                  40                  45

Thr Pro Thr Lys His Ala Ile Ile Gln Ala Leu Val His Leu Lys Asn
    50                  55                  60

Ser Gln Lys Ala Ser Lys Ala Cys Cys Val Pro Thr Lys Leu Glu Pro
65                  70                  75                  80

Ile Ser Ile Leu Tyr Leu Asp Lys Gly Val Val Thr Tyr Lys Phe Lys
                85                  90                  95

Tyr Glu Gly Met Ala Val Ser Glu Cys Gly Cys Arg
            100                 105

<210> SEQ ID NO 158
<211> LENGTH: 134
<212> TYPE: PRT
<213> ORGANISM: Homo Sapiens

<400> SEQUENCE: 158

Ser Pro Asp Lys Gln Met Ala Val Leu Pro Arg Arg Glu Arg Asn Arg
1               5                   10                  15

Gln Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Ser Asp Lys
                85                  90                  95

Val Gly Gln Ala Cys Cys Arg Pro Ile Ala Phe Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
    130

<210> SEQ ID NO 159
```

```
<211> LENGTH: 120
<212> TYPE: PRT
<213> ORGANISM: Homo Sapiens

<400> SEQUENCE: 159

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
50                  55                  60

His Ala Val Ile Gln Thr Leu Met Asn Ser Met Asp Pro Glu Ser Thr
65                  70                  75                  80

Pro Pro Thr Cys Cys Val Pro Thr Arg Leu Ser Pro Ile Ser Ile Leu
                85                  90                  95

Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 160
<211> LENGTH: 114
<212> TYPE: PRT
<213> ORGANISM: Homo Sapiens

<400> SEQUENCE: 160

Ala Arg Ala Arg Asn Gly Asp His Cys Pro Leu Gly Pro Gly Arg Cys
1               5                   10                  15

Cys Arg Leu His Thr Val Arg Ala Ser Leu Glu Asp Leu Gly Trp Ala
            20                  25                  30

Asp Trp Val Leu Ser Pro Arg Glu Val Gln Val Thr Met Cys Ile Gly
        35                  40                  45

Ala Cys Pro Ser Gln Phe Arg Ala Ala Asn Met His Ala Gln Ile Lys
    50                  55                  60

Thr Ser Leu His Arg Leu Lys Pro Asp Thr Val Pro Ala Pro Cys Cys
65                  70                  75                  80

Val Pro Ala Ser Tyr Asn Pro Met Val Leu Ile Gln Lys Thr Asp Thr
                85                  90                  95

Gly Val Ser Leu Gln Thr Tyr Asp Asp Leu Leu Ala Lys Asp Cys His
            100                 105                 110

Cys Ile

<210> SEQ ID NO 161
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(10)
<223> OTHER INFORMATION: Xaa can be any naturally occurring amino acid

<400> SEQUENCE: 161

Cys Xaa Xaa Xaa Xaa Xaa Xaa Xaa Xaa Xaa Cys
1               5                   10
```

-continued

```
<210> SEQ ID NO 162
<211> LENGTH: 32
<212> TYPE: PRT
<213> ORGANISM: Artificial Sequence
<220> FEATURE:
<223> OTHER INFORMATION: Synthetic construct

<400> SEQUENCE: 162

Thr Phe Lys Glu Leu Val Tyr Glu Thr Tyr Arg Val Pro Gly Cys Ala
1               5                   10                  15

His His Ala Asp Ser Leu Tyr Thr Tyr Pro Val Ala Thr Gln Ala His
                20                  25                  30
```

BINDING COMPOUNDS, IMMUNOGENIC COMPOUNDS AND PEPTIDOMIMETICS

STATEMENT ACCORDING TO 37 C.F.R. §1.52(e)(5)-SEQUENCE LISTING SUBMITTED ON COMPACT DISC

Pursuant to 37 C.F.R. §1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "P71391US00.txt" which is 69 KB and created on May 6, 2008.

The invention relates to the field of biology. More specifically, the invention relates to detection, identification and/or generation of binding molecules.

Interactions between binding molecules, which in general are biomolecules, and their corresponding ligands are central to life. Cells often bear or contain receptor molecules that are capable of specifically interacting or binding with another molecule such as for instance a hormone, a peptide, a drug, an antigen, an effector molecule or with another receptor molecule; enzymes bind with their substrate; antibody molecules and/or T cells bind with an antigen, nucleic acid with protein, and so on. By "interacting or binding" it is meant that the binding molecule and ligand approach each other within the range of molecular forces, and may influence each others properties. This approach takes the binding molecule and its ligand through various stages of molecular recognition comprising increasing degrees of intimacy and mutual effect: they bind, albeit not always irreversibly.

Binding molecules have binding ability because they comprise distinct binding sites allowing for the recognition of the ligand in question. The ligand, in turn, has a corresponding binding site, and only when the two binding sites can interact by—essentially spatial—complementarity, the two molecules can bind. Needless to say that, molecules having three dimensions, binding sites are of a three dimensional nature, often one or more surface projections or protuberances of one binding site correspond to one or more pockets or depressions in the other, forming a three-dimensional lock-and-key arrangement, sometimes in an induced-fit variety. Sometimes, such a protuberance comprises a single loop of the molecule in question, and it is only this protuberance that essentially forms the binding site. In that case one often terms these binding sites as comprising a linear or continuous binding site, wherein a mere linear part of the molecule in question is in essence responsible for the binding interaction. This terminology is widely used to describe for example antibody-antigen reactions wherein the antigen comprises part of a protein sequence; a linear peptide. One then often speaks about a linear or continuous epitope, whereby the binding site (epitope) of the antigenic molecule is formed by a loop of consecutively bound amino acids. However, similar continuous binding sites (herein epitope and binding site are use interchangeably) can be found with receptor-antigen interactions (such as with a T-cell receptor), with receptor-ligand interactions such as with hormone receptors and agonists or antagonists thereof, with receptor-cytokine interactions or with for example enzyme-substrate or receptor-drug interactions, whereby a linear part of a molecule is recognised as the binding site.

More often, however, such a protuberance or protuberances and depressions comprise various, distinct parts of the molecule in question, and it are the combined parts that essentially form the binding site. Commonly, one names such a binding site comprising distinct parts of the molecule in question a discontinuous or conformational binding site or epitope. For example, binding sites laying on proteins having not only a primary structure (the amino acid sequence of the protein molecule), but also secondary and tertiary structure (the folding of the molecule into alpha-helices or beta-sheets and its overall shape), and sometimes even quaternary structure (the interaction with other protein molecules) may comprise in their essential protuberances or depressions amino acids or short peptide sequences that lay far apart in the primary structure but are folded closely together in the binding site. In linear (continuous) binding sites the key amino acids mediating the contacts with the antibody are typically located within one part of the primary structure usually not greater than 15 amino acids in length. Peptides covering these sequences have affinities to the target proteins that are roughly within the range shown by the intact protein ligand. In conformational (discontinuous) binding sites however the key residues are in general distributed over two or more binding regions, which are often separated in the primary structure. Upon folding, these binding regions can be brought together on the protein surface to form a composite binding site. Even if the complete binding site mediates a high affinity interaction, peptides covering only one binding region, as synthesized in a linear scan of overlapping peptides, generally have very low affinities that often cannot be measured e.g. in normal ELISA or Biacore experiments.

Due to the central role binding molecules and their ligands play in life, there is an ever expanding interest in detection, identification and/or generation of binding molecules. Insight into the nature of binding sites for instance provides the possibility to design compounds capable of interfering with the binding between a binding molecule and its ligand. Moreover, the generation of binding molecules mimicking binding sites of (complex) molecules is desired for a wide variety of applications. For instance, peptides mimicking a binding site of a proteinaceous molecule are suitable for diagnostic, therapeutic and/or prophylactic uses. Such peptides are for instance suitable for use as an agonist or antagonist for a ligand-receptor pair.

Moreover, there is an ever expanding interest in detection, identification and/or generation of immunogenic compounds. Immunogenic compounds are particularly suitable for obtaining antibodies and/or T cells of interest. Moreover, such immunogenic compounds are suitable for evoking an immune response in a host, which immune response preferably provides partial or full protection against subsequent challenge with said immunogenic compound and/or with an immunogen from which said immunogenic compound is derived. Preferably immunogenic compounds are generated that are capable of providing a partially or fully protective immune response in a host against subsequent challenge with a proteinaceous molecule of interest. Such immunogenic compounds typically comprise a peptide sequence that is wholly or in part derived from said proteinaceous molecule of interest.

Methods for screening for a binding compound and/or immunogenic compound of interest generally involve the production of a plurality of putative binding sites and/or immunogenic compounds and subsequent incubation with a molecule of interest (such as for instance a ligand, an antibody and/or a T cell) in order to find a compound capable of specifically binding said molecule of interest. An early work in the peptide field is WO 84/03564, related to a method of detecting or determining antigenically active amino acid sequences or peptides in a protein. This work, providing the so-called Pepscan technology, involves the production of a plurality of different peptides after which the synthesised peptides are each tested with the binding molecule in question. This method allows detection of a continuous binding site and/or continuous epitope in a protein or peptide sequence. Pepscan technology taken in a broad sense provides for the testing for or identification of (albeit linear) peptides essentially identical with, analogous to or mimicking binding sites, immunogenic sites or ligands of a various nature (mimotopes, Geyssen at al, Mol. Immunol. 23:709-715, 1986). Pepscan technology allows identification of linear peptide sequences interacting with receptor molecules, enzymes, antibodies, and so on, in a rapid and straightforward fashion, allowing testing of a great many peptides for their reactivity with the binding molecule in question with relatively little effort.

However, the Pepscan technology is not suitable for testing of discontinuous or conformational binding sites. Moreover, the Pepscan technology is not suitable for obtaining peptides with a desired characteristic which peptides have an amino acid sequence that is not directly derived from the primary amino acid sequence of a given proteinaceous molecule.

In WO 02/31510 a method for screening for discontinuous binding sites is disclosed. A molecular library is generated wherein a first segment is spotted in close proximity to a second segment in order to form a test entity. Various test entities comprising different segments are subsequently screened for the presence of a desired binding site. This method is suitable for screening for the presence of a variety of binding sites present within a compound of interest. The segments that are spotted in close proximity to each other are either randomly synthesized or derived from a known amino acid sequence of a proteinaceous molecule. However, if the segments are randomly synthesized, a huge amount of test entities needs to be synthesized which is laborious and time consuming. On the other hand, if the segments are directly derived from the primary sequence of a proteinaceous molecule of interest, a rather limited collection is obtained since peptides having an amino acid sequence that is not directly derived from said primary amino acid sequence of said proteinaceous molecule are not produced.

The present invention provides a method for producing compounds that are suitable for screening for the presence of a binding site and/or immunogenic site of interest. A method of the invention provides compounds that on the one hand are at least in part based on a given proteinaceous molecule, but on the other hand do not necessarily contain sequences that are exactly similar to (a part of) the primary sequence of said proteinaceous molecule. The invention provides a method wherein at least one sequence derived from the primary sequence of a proteinaceous molecule of interest is used in order to systematically generate and screen for binding compounds and/or immunogenic compounds. The invention provides an efficient method for generating, selecting and/or identifying immunogenic compounds and/or binding compounds whose properties are comparable to, or even better than, a binding site and/or immunogenic site of an original proteinaceous molecule of interest. A preferred embodiment of a method of the invention is particularly suitable for screening for desired binding characteristics and/or immunogenic characteristics because this embodiment provides peptides bound to a scaffold. The use of a scaffold more often results in peptides having a biologically relevant secondary structure, as compared to free, linear peptides. Moreover, if a preferred scaffold of the invention is used, produced peptides need not be protected before they are attached to the scaffold, due to the fact that the formation of a first linkage between a peptide and a scaffold accelerates the formation of a second linkage between said peptide and said scaffold. Such preferred scaffold needs not be selectively functionalized. Hence, in a preferred embodiment an efficient method is provided wherein selected amino acid sequences are incorporated into peptides, which peptides are coupled to a scaffold without the need of cumbersome protection and deprotection procedures. Said peptides are preferably coupled to said scaffold in solution, more preferably in an aqueous solution. The use of an aqueous solution provides various advantages. For instance, water is cheap, non-toxic and easy to remove by freeze drying (in comparison to for instance DMF and DMSO). Moreover, (buffer) salts dissolve very well in water and water also has good solubility properties for most peptides (except for very hydrophobic ones).

Once a compound with a desired binding property and/or immunogenic property is selected with a method according to the invention, it is for instance suitable for use as a peptidomimetic, an agonist, an antagonist, for preparing an immunogenic composition and/or for gaining more insight into the properties of a proteinaceous molecule of interest (such as for instance the secondary, tertiary and/or quaternary structure). While it is possible to identify a (discontinuous) binding site and/or epitope within a proteinaceous molecule of interest, it is preferred to provide a compound with at least one improved characteristic, preferably at least one improved immunogenic and/or binding characteristic, as compared to a given proteinaceous molecule.

The invention in one aspect provides a method for producing a compound which is suitable for testing for the presence and/or identification of an immunogenic compound and/or a binding compound, the method comprising:

selecting at least one amino acid residue within the primary sequence of at least one proteinaceous molecule, whereby said selected amino acid residue is preferably at least two amino acid residues located from other selected amino acid residues, if any;

selecting at least one flanking sequence of at least one selected amino acid residue, which flanking sequence is located in the direction of the N-terminus and/or C-terminus of said at least one proteinaceous molecule, said flanking sequence having a length of between 2 and 48 amino acid residues; and producing a peptide comprising at least one of said flanking sequences, said peptide having a length of at least 4 and at most 50 amino acid residues.

In one embodiment said flanking sequence includes said selected amino acid residue. This is however not necessary.

A method according to the invention involves the production of at least one peptide—preferably a plurality of peptides—comprising sequences that are at least in part derived from a proteinaceous molecule of interest. A preferred embodiment involves systematic "shuffling" of flanking sequences (which flanking sequences are derived from a proteinaceous molecule of interest), resulting in a plurality of peptides which are preferably screened for the presence of a binding compound and/or immunogenic compound of interest. By varying the length, kind and/or amount of flanking sequences, a plurality of peptides is produced. The amount of peptides and the extent of differences between said peptides is chosen at will, depending on a particular application.

A method according to the present invention is particularly suitable for producing a plurality of compounds and screening said plurality of compounds for the presence of a compound with at least one desired characteristic. Said plurality of compounds preferably comprises at least 10, more preferably at least 100, most preferably at least 1000 compounds in order to enhance the chance that a compound with a desired characteristic is generated and selected. In a preferred embodiment said plurality of compounds is screened for the presence of a compound with a desired immunogenic characteristic. This is for instance done by incubating a plurality of compounds of the invention with a binding molecule such as an antibody and/or T cell and determining whether at least one compound is capable of specifically binding said binding molecule.

In a preferred embodiment a compound is selected which is capable of eliciting an immune response in a host. In this embodiment at least one compound of the invention is administered to a non-human animal and it is determined whether an immune response is elicited. Most preferably, a compound is selected which is capable of eliciting an immune response in a host, which immune response is directed against a proteinaceous molecule of interest. Hence, a compound is preferably selected which is capable of eliciting an immune response in a host, such as a humoral and/or cellular response during which antibodies and/or T cells are produced, which antibodies and/or T cells are not only capable of specifically binding said compound, but which are also capable of specifically binding a proteinaceous molecule of interest. It was found that a method of the present invention is particularly effective in generating and detecting such binding compounds and/or immunogenic compounds. In a preferred embodiment a compound is firstly selected during a first screening procedure using a binding molecule such as an antibody and/or T cell before it is administered to a non-human animal. Hence, according to this embodiment a two-step procedure is preferred wherein peptides according to the invention are firstly screened in vitro, after which the immunogenic properties of promising candidate peptides are subsequently investigated in vivo.

A method of the invention is applicable to any given proteinaceous molecule of interest whose primary sequence is at least partly known. If a method of the invention is performed in order to produce an immunogenic compound and/or binding compound, it is preferred to select at least one amino acid residue from a surface-exposed region of said proteinaceous molecule. This is of course only possible if the (secondary, tertiary and/or quaternary) structure of said proteinaceous molecule is at least in part known. A method of the invention is however not restricted to proteinaceous molecules with an at least partially known structure. It is also possible to perform a method of the invention with a proteinaceous molecule with unknown (secondary, tertiary and/or quaternary) structure. In that case, of course, amino acid residues of said proteinaceous molecule are selected at random. By selecting an amino acid residue is meant herein that an amino acid residue is taken into consideration. It need not be physically isolated or synthesized.

Once an amino acid residue is selected, at least one flanking sequence of said amino acid residue is subsequently selected. A flanking sequence is defined as a number of consecutive amino acid residues which are located within five, preferably within three, amino acid residues from said selected amino acid residue in the primary sequence of said proteinaceous molecule of interest. Preferably, said flanking sequence is located directly adjacent to said selected amino acid residue. Hence, if an amino acid residue at position n is selected, a flanking sequence located in the direction of the N-terminus preferably ends at amino acid position n−1, while a flanking sequence located in the direction of the C-terminus preferably starts at amino acid position n+1. In one embodiment a flanking sequence includes said selected amino acid residue. According to this embodiment, a flanking sequence located in the direction of the N-terminus ends at amino acid position n, and/or a flanking sequence located in the direction of the C-terminus starts at amino acid position n. As used herein, a flanking sequence is called to "start" at its most N-terminal amino acid residue and a flanking sequence is called to "end" at its most C-terminal amino acid residue. The length of said flanking sequences is preferably between 2 and 48 amino acid residues. Preferably, said length is between 4 and 30 amino acid residues, more preferably between 4 and 21 amino acid residues. The length of a flanking sequence of a selected amino acid residue that is located in the direction of the N-terminus need not necessarily to be the same as the length of a flanking sequence of the same selected amino acid residue that is located in the direction of the C-terminus, although this is of course possible. Moreover, different flanking sequences of the same selected amino acid residue can be chosen, said flanking sequences being in the direction of the N-terminus and/or C-terminus, which flanking sequences are of different length. Hence, a method of the invention also comprises the selection of at least two flanking sequences of the same selected amino acid residue, said at least two flanking sequences being in the same direction (of the N-terminus or C-terminus).

Once at least one flanking sequence is selected, a peptide is produced comprising at least one of said flanking sequences. A peptide is defined herein as a compound comprising at least two consecutive amino acid residues that are linked to each other via a peptide bond. Besides natural amino acid residues, a peptide of the invention may comprise non-natural amino acid residues such as for instance D-amino acid residues. A peptide of the invention comprising at least one of said flanking sequences is produced using any method known in the art, such as for instance solid-phase synthesis. The length of said peptide is between 4 and 50 amino acid residues. Preferably however, said peptide has a length of between 6 and 25 amino acid residues, since peptides with this length have been shown to provide optimal test results. Also provided is therefore a method according to the invention wherein said peptide has a length of at most 25 amino acid residues. Preferably a plurality of peptides with different flanking sequences is synthesized, in order to efficiently screen for a desired binding compound and/or immunogenic compound.

A peptide of the invention is preferably coupled to a scaffold in order to obtain a compound having a biologically relevant secondary structure. Moreover, scaffold-bound peptides are generally more stable as compared to peptides which are free in solution. One embodiment therefore provides a method according to the invention comprising contacting a produced peptide with a scaffold in order to form at least one linkage between said peptide and said scaffold. Preferably, at least two linkages between said peptide and a scaffold are formed in order to obtain a constrained, biologically relevant structure. In a particularly preferred embodiment a peptide according to the invention is coupled to a scaffold, whereby the formation of a first linkage between said peptide and said scaffold accelerates the formation of a consecutive linkage. This provides the advantage that reactive side chains of said peptide need not be protected by a protecting group during the coupling reaction between said peptide and said scaffold. Once a first linkage is formed, the second linkage is formed quickly enough in order to avoid the formation of too many unfavourable byproducts.

Therefore, the invention in one aspect provides a method for producing a compound which is suitable for testing for the presence and/or identification of an immunogenic compound and/or a binding compound, the method comprising:

selecting at least one amino acid residue within the primary sequence of at least one proteinaceous molecule, whereby said selected amino acid residue is preferably at least two amino acid residues located from other selected amino acid residues, if any;

selecting at least one flanking sequence of at least one selected amino acid residue, which flanking sequence is located in the direction of the N-terminus and/or C-terminus of said at least one proteinaceous molecule, said flanking sequence having a length of between 2 and 48 amino acid residues;

producing a peptide comprising at least one of said flanking sequences and at least two groups capable of reacting with a scaffold, said peptide having a length of at least 4 and at most 50 amino acid residues; and contacting said peptide with said scaffold in order to form at least two linkages between said peptide and said scaffold, whereby the formation of a linkage accelerates the formation of a consecutive linkage.

Produced peptides are preferably contacted with a scaffold in order to form at least two linkages between said peptide and said scaffold, whereby the formation of a linkage between said peptide and said scaffold accelerates the formation of a consecutive linkage between said peptide and said scaffold. A scaffold is defined herein as any solid support capable of binding a peptide of the invention. Once a peptide is bound to a scaffold, its structure is preferably at least in part different from the structure of said peptide when free in solution. The use of a scaffold results in a peptide of the invention with a biologically relevant secondary structure. Moreover, the resulting peptide-scaffold compound is generally more stable as compared to free peptides. It has been demonstrated that the fixed structure of a peptide bound to a scaffold is particularly suitable when said scaffold-bound peptide is to be used as an immunogenic compound and/or a binding compound such as a ligand, agonist or antagonist. Preferably each peptide of a given plurality of peptides of the invention is coupled to essentially the same kind of scaffold, allowing for direct comparison between the individual peptides of said plurality of peptides. If the same kind of scaffold is used, differences between various compounds comprising said scaffold and peptide are more likely to be attributable to the differences between the peptides. In a preferred embodiment an array is produced comprising a plurality of peptides of the invention, each peptide bound to a scaffold, allowing rapid selection of promising compounds from among many test compounds.

In one embodiment a method of the invention is provided wherein said at least two groups capable of reacting with a scaffold are identical. This provides the advantage that at least two linkages between the peptide and a scaffold are formed under the same reaction conditions. For ease of linkage, it is preferred that a peptide of the invention comprises at least one SH-functionality. In a more preferred embodiment said at least two groups capable of reacting with a scaffold are two SH-functionalities. An SH-functionality is defined herein as a part of a peptide (preferably an amino acid residue) comprising a sulfhydryl or thiol group (an SH group). However, other groups are possible. In a further preferred embodiment said at least one SH-functionality is a cysteine residue. In a most preferred embodiment a method of the invention is provided wherein said at least two groups capable of reacting with a scaffold are cysteine residues. In one embodiment, said groups capable of reacting with a scaffold are located at the first amino acid position of said peptide and at the last amino acid position of said peptide. In a further embodiment said groups capable of reacting with a scaffold which groups are located at the first amino acid position and at the last amino acid position of said peptide are cysteine residues. One embodiment therefore provides a method according to the invention comprising producing a peptide wherein the first and the last amino acid residues of said peptide are cysteines. In other embodiments at least one of said groups capable of reacting with a scaffold are located within the peptide sequence, as will be described in more detail throughout this application.

A peptide of the invention comprising at least one flanking sequence is coupled to a scaffold in order to obtain stable compounds with desired biological activities. In principle, any scaffold is suitable. Preferably however scaffold is used whereby the formation of a first linkage between a peptide of the invention and a scaffold accelerates the formation of a second linkage. In one preferred embodiment at least one linkage between a peptide of the invention and a scaffold comprises a thioether linkage. In a further preferred embodiment a peptide of the invention is coupled to a (hetero)aromatic compound, which (hetero)aromatic compound preferably comprises at least two benzylic halogen substituents, preferably a halomethylarene. In a preferred embodiment a peptide of the invention is coupled to a bis(bromomethyl)benzene, a tris(bromomethyl)benzene, a tetra(bromomethyl)benzene or a derivative thereof. Most preferably a peptide according to the invention is coupled to meta-1,3-bis(bromomethyl)benzene (m-T2), ortho-1,2-bis(bromomethyl)benzene (o-T2), para-1,4-bis(bromomethyl)benzene (p-T2), meta-1,3-bis(bromomethyl)pyridine (m-P2), 2,4,6-tris(bromomethyl)mesitylene (T3) or meta-1,3-bis(bromomethyl)-5-azidobenzene (m-T3-N3).

In a particularly preferred embodiment, a nucleophilic substitution reaction according to WO 2004/077062 is performed in order to couple a peptide according to the invention to a scaffold. Such coupling reaction involves a nucleophilic substitution reaction wherein a molecule with a free nucleophilic functionality reacts with a scaffold. In a preferred embodiment said nucleophilic functionality comprises a thiol or sulfhydryl group. Thiols are effective nucleophiles for substitution at saturated carbon atoms. It is in general not difficult to provide a molecule with a nucleophilic functionality. For example, a peptide or peptidomimetic is easily functionalised with a thiol moiety by incorporating a cysteine residue in the peptide amino acid sequence.

Of course, various other nucleophilic functionalities, like amino acids with an alcohol (—OH) or an amine (—NH) moiety, can be similarly incorporated into a peptide of the invention. However, it should be emphasized that the chemistry required for the coupling reaction of an alcohol or amine in general does not allow to use unprotected peptides, in contrast to a method provided using SH-functionalized peptides. Therefore, a peptide of the invention preferably comprises at least two SH-functionalities, preferably at least two free cysteine sulfhydryl groups. A method according to the invention allows the use of an unprotected peptide wherein none of the amino acid side chains are protected or treated otherwise to prevent unwanted participation in the coupling reaction. Thus, a method according to the invention preferably comprises contacting an essentially unprotected peptide of the invention with a scaffold. Importantly, a method provided herein using an unprotected peptide saves costly time, effort and money because it does not require multistep protection/deprotection steps.

In a preferred embodiment, a peptide according to the invention is coupled to a scaffold by at least two nucleophilic substitution reactions wherein said peptide has at least two free nucleophilic functionalities that form two bonds or linkages with a scaffold molecule. For instance, said peptide reacts with two, or more, saturated carbon atoms of a scaffold, said carbon atom being part of a reactive group. A nucleophilic substitution can also be an intermolecular process when the nucleophile and leaving group are part of a single molecule or molecular entity. In a preferred embodiment of the invention, a scaffold is provided with at least one molecule via at least one intramolecular nucleophilic substitution reaction. Intramolecular processes have a far more favourable entropy than the analogous intermolecular reactions because it is not necessary for two separate molecules to come together.

A common characteristic of a nucleophilic reaction that takes place on saturated carbon, is that the carbon atom is almost always bonded to a heteroatom, which is an atom other than carbon or hydrogen. Furthermore, the heteroatom is usually more electronegative than carbon and is also the so-called leaving group (L) in the substitution reaction. The leaving group departs with the electron pair by which it was originally bonded to the carbon atom. In a preferred embodiment, a scaffold is used which contains at least two leaving groups in order to facilitate the formation of at least two bonds with at least one peptide. The ease with which a leaving group departs can be related to the basicity of that group; weak bases are in general good leaving groups because they are able to accommodate the electron pair effectively. The reactivity of a reactive group is largely determined by the tendency of a leaving group to depart. Another factor which has some bearing on reactivity of a reactive group is the strength of the bond between the leaving group and the carbon atom, since this bond must break if substitution is to occur.

Thus, in a preferred embodiment, a scaffold comprising at least two good leaving groups is used in a method according to the present invention. Good leaving groups are in general the conjugate bases of strong acids. The most important leaving groups are conjugate bases of acids with pKa values below 5. Particularly interesting leaving groups include halide ions such as I—, Br—, and Cl—. A carbon-halogen (C—X) bond in an alkyl halide is polarised, with a partial positive charge on the carbon and a partial negative charge on the halogen. Thus, the carbon atom is susceptible to attack by a nucleophile (a reagent that brings a pair of electrons) and the halogen leaves as the halide ion (X—), taking on the two electrons from the C—X bond. In one embodiment, a reactive group comprises a carbon atom susceptible to attack by a nucleophile wherein said reactive group comprises a carbon-halogen bond. In a preferred embodiment, a scaffold comprising at least two of such reactive groups is used to react with a di-SH functionalised peptide as nucleophile. Provided is a method according to the invention wherein a peptide of the invention is coupled to a scaffold comprising a halogenoalkane. Halogenoalkanes (also known as haloalkanes or alkyl halides) are compounds containing a halogen atom (fluorine, chlorine, bromine or iodine) joined to one or more carbon atoms in a chain. Provided herein are dihaloscaffolds, comprising two halogen atoms, and tri- and tetrahaloscaffolds for the synthesis of conformationally constraint peptide constructs consisting of one or more looped peptide segments. In general, a good leaving group is electronegative to polarize the carbon atom, it is stable with an extra pair of electrons once it has left, and is polarizable, to stabilize the transition state. With the exception of iodine, all of the halogens are more electronegative than carbon. Chlorine and bromine have fairly similar electronegativities and polarize the bond with the carbon fairly equally. When ionized, both are very weak bases with Br— being the weaker one of the two. Bromide ion is also more polarizable due to its larger size.

Therefore, a method provided is advantageously practiced using a scaffold comprising at least two Cl atoms, more preferred using a scaffold comprising at least one Cl atom and at least one Br atom and even more preferred using a scaffold comprising at least two Br atoms.

In a preferred embodiment, a scaffold comprises an allylic system. In an allylic system, there are three carbon atoms, two of which are connected through a carbon-carbon double bond. In a preferred embodiment, the formation of a bond or linkage between a scaffold and a peptide according to the invention occurs via an allylic substitution reaction. An allylic substitution reaction refers to a substitution reaction occurring at position 1 of an allylic system, the double bond being between positions 2 and 3. The incoming group is attached to the same atom 1 as the leaving group, or the incoming group becomes attached at the relative position 3, with movement of the double bond from ⅔ to ½. The reaction rate of allylic substitutions is very high, because the allyl cation reaction intermediate, a carbon atom bearing a positive charge attached to a doubly-bonded carbon, is unusually stable. This is because an allylic cation is a resonance hybrid of two exactly equivalent structures. In either of the contributing structures, there is an empty p orbital with the pi cloud of the electron-deficient carbon. Overlap of this empty p orbital with the pi cloud of the double bond results in delocalisation of the pi electrons, hereby providing electrons to the electron-deficient carbon and stabilizing the cation. Even more preferred is a scaffold comprising at least two allylic halogen atoms. Due to electron delocalisation, allyl halides tend to undergo ionization very readily to produce a carbocation and a halide ion, such that breaking the carbon halide bond is rapid.

In a further embodiment of the invention, a carbon-oxygen double bond (i.e. a carbonyl group) is present in a scaffold. Similarly to the allylic system, resonance structures can be formed which contribute to stabilization of a carbocation. For example, a scaffold comprises two or more reactive groups comprising the structure —C(O)—CH$_2$-halogen.

Furthermore, in a nucleophilic substitution reaction, the structure of the substrate plays just as important role as the nature of the leaving group. For example, if a nucleophile attacks the backside of the carbon, the reaction proceeds unhindered if the leaving group is bonded to a methyl, where the hydrogens leave enough surface to attack the carbon. As that carbon becomes more substituted, larger groups hinder the path the nucleophile must take to displace the leaving group. For these reasons, it is also advantageous that a scaffold comprise at least two halomethyl groups.

In one embodiment, a scaffold comprises a conjugated polyene, also known as aromatic compound, or arene, which is provided with at least two reactive groups. An aromatic compound is flat, with cyclic clouds of delocalised pi electrons above and below the plane of the molecule. Preferably, a molecular scaffold according to the invention comprises at least two benzylic halogen substituents, like for instance halomethyl groups. Suitable examples include, but are not limited, to di(halomethyl)benzene, tri(halomethyl)benzene or tetra(halomethyl)benzene and derivatives thereof. The advantage of a benzylic halogen substituent is mainly to be sought in the special stability associated with the resonance of conjugated polyenes known as aromatic compounds; a benzylic halogen atom has an even stronger tendency to leave a carbon on which a nucleophilic substitution reaction takes place.

The embodiment involving reaction of a suitable peptide, such as SH-SH peptides, with halomethylbenzene derivatives is of very wide scope. The reaction runs successfully with a variety of aromatic compounds carrying at least two halomethyl groups. These groups can be positioned in either ortho, meta, or para position. The intramolecular catalytic effect as described above is different for each mode of coupling because para and meta-cyclophanes are generally more strained than ortho-cyclophanes. Also provided are all other (hetero)aromatic compounds with at least two halomethyl groups in ortho-, meta-, or para-position for the synthesis of a scaffold with at least one looped peptide structure.

Suitable molecular scaffolds for use in a method according to the invention also include polycyclic aromatic compounds with smaller or larger ring structures. However, a scaffold for use in a method according to the invention is not limited to hydrocarbons. In contrast, a method provided is also suitably practiced using a heterocyclic aromatic scaffold—a cyclic molecule with at least one atom other than carbon in the ring structure, most commonly nitrogen, oxygen or sulfur. Examples include pyrrole, furan, thiophene, imidazole, oxazole, thiazole, pyrazole, -3-pyrroline, pyridine, pyrimidine and derivatives thereof. Preferred heterocyclic aromatic scaffold include but are not limited to those comprising at least two halomethyl groups. A preferred scaffold is meta-dibromo-pyridine.

In another embodiment, a method provided comprises the use of a scaffold that is based on or which consists of multiple ring aromatic structures, such as fused-ring aromatic compounds. Two aromatic rings that share a carbon-carbon bond are said to be fused. Suitable fused-ring aromatic scaffolds include for example naphthalene, anthracene or phenanthrene and derivatives thereof, provided that they contain at least two reactive groups. In a preferred embodiment, a fused-ring aromatic scaffold comprises at least two reactive groups wherein each group contains a highly reactive benzylic halogen atom, for example a halomethyl group.

Molecules comprising multiple aromatic or conjugated systems wherein the systems do not share a pair of carbon atoms are also useful as scaffold molecule. For example, a scaffold comprises a multi-ring or fused ring structure, for instance a scaffold wherein aromatic, e.g. benzene, rings are connected directly via a carbon-carbon bond can be tested. Alternatively, said rings are connected via a linker comprising at least one atom. Examples of suitable scaffolds in a method of the invention are given in FIGS. 4, 5 and 6. A person skilled in the art will be able to select which versions of these molecules to use. From a commercial point of view, a scaffold according to the invention is preferably commercially available at a relatively low cost and can be obtained in large quantities. For example, the dibromoscaffold 1,3-bis(bromomethyl)benzene is currently being sold for only around 5 euro per gram.

A method according to WO 2004/077062 thus allows for simple and straightforward coupling of a peptide according to the invention to a scaffold wherein a first and second reactive group are used. The formation of a first linkage accelerates the formation of a consecutive linkage. Hence, the formation of a first linkage results in a cascade of reactions wherein the formation of a first linkage, also referred to as a (chemical) bond or connection, via a first reactive group increases the reactivity of a second reactive group, and so on. Said chemical reactions involve changes at functional groups while the molecular skeleton of the scaffold remains essentially unchanged. An advantage of a method according to WO 2004/077062 is that essentially unprotected peptides can be coupled to a scaffold and the scaffold need not be selectively functionalized. Moreover, a method according to WO 2004/077062 allows coupling of a peptide according to the present invention in an aqueous solution, whereas other known coupling procedures are often performed in organic solvents via multiple protection-deprotection cycles. A preferred embodiment therefore provides a method according to the present invention wherein a peptide is coupled to a scaffold wherein the formation of a first linkage between said peptide and said scaffold accelerates the formation of a second linkage between said peptide and said scaffold. A further preferred embodiment provides a method according to the invention wherein said peptide is coupled to a scaffold in solution. Most preferably, an aqueous solution is used.

Outlined below is a non-limiting schematic example of one embodiment according to the present invention. In this example two amino acid residues of a proteinaceous molecule of interest are selected. Said amino acid residues are preferably both selected from a surface-exposed region of said proteinaceous molecule. Said selected amino acid residues are preferably at least two amino acid residues located from each other so that a flanking sequence of a first selected amino acid residue can be selected that does not comprise a second selected amino acid residue. In this schematic example, the primary sequence of (part of) a proteinaceous molecule is represented by the sequence $X_1$-$X_{24}$ (X stands for any amino acid residue):

Primary Sequence $X_1X_2X_3X_4X_5X_6X_7X_8X_9X_{10}X_{11}X_{12}X_{13}X_{14}X_{15}X_{16}X_{17}X_{18}X_{19}X_{20}X_{21}X_{22}X_{23}X_{24}$ Subsequently, amino acid residues $X_{10}$ and $X_{15}$ are for instance selected.

Then, the following flanking sequences are for instance chosen:

Flanking sequences of $X_{10}$: $X_5X_6X_7X_8X_9$ and $X_{11}X_{12}$

Flanking sequences of $X_{15}$: $X_{13}X_{14}$ and $X_{16}X_{17}X_{18}X_{19}X_{20}$ Subsequently, peptides are produced comprising at least one of said flanking sequences and at least two groups capable of reacting with a scaffold. In this example, said two groups capable of reacting with a scaffold are two cysteine residues, which are the first and last amino acid residues of said peptide. Of course, many alternative groups can be used and the positions of said groups within said peptide can be varied.

In this example the following peptides are for instance generated:

Peptides Comprising 1 Flanking Sequence:
 $CX_5X_6X_7X_8X_9C$ (SEQ ID NO:1)
 $CX_{11}X_{12}C$ (SEQ ID NO:2)
 $CX_{13}X_{14}C$ (SEQ ID NO:2)
 $CX_{16}X_{17}X_{18}X_{19}X_{20}C$ (SEQ ID NO:1)

Peptides Comprising 2 Flanking Sequences:
 $CX_5X_6X_7X_8X_9X_5X_6X_7X_8X_9C$ (SEQ ID NO:3)
 $CX_5X_6X_7X_8X_9X_{11}X_{12}C$ (SEQ ID NO:4)
 $CX_5X_6X_7X_8X_9X_{13}X_{14}C$ (SEQ ID NO:4)
 $CX_5X_6X_7X_8X_9X_{16}X_{17}X_{18}X_{11}X_{20}C$ (SEQ ID NO:5)
 $CX_{11}X_{12}X_5X_6X_7X_8X_9C$ (SEQ ID NO:4)
 $CX_{11}X_{12}X_{11}X_{12}C$ (SEQ ID NO:6)
 $CX_{11}X_{12}X_{13}X_{14}C$ (SEQ ID NO:7)
 $CX_{11}X_{12}X_{16}X_{17}X_{18}X_{19}X_{20}C$ (SEQ ID NO:4)
 $CX_{13}X_{14}X_5X_6X_7X_8X_9C$ (SEQ ID NO:4)
 $CX_{13}X_{14}X_{11}X_{12}C$ (SEQ ID NO:7)
 $CX_{13}X_{14}X_{13}X_{14}C$ (SEQ ID NO:6)
 $CX_{13}X_{14}X_{16}X_{17}X_{18}X_{19}X_{20}C$ (SEQ ID NO:4)
 $CX_{16}X_{17}X_{18}X_{19}X_{20}X_5X_6X_7X_8X_9C$ (SEQ ID NO:5)
 $CX_{16}X_{17}X_{18}X_{19}X_{20}X_{11}X_{12}C$ (SEQ ID NO:4)

$CX_{16}X_{17}X_{18}X_{19}X_{20}X_{13}X_{14}C$ (SEQ ID NO:4)
$CX_{16}X_{17}X_{18}X_{19}X_{20}X_{16}X_{17}X_{18}X_{19}X_{20}C$ (SEQ ID NO:3)

Some Possible Peptides Comprising 3 Flanking Sequences:

$CX_5X_6X_7X_8X_9X_5X_6X_7X_8X_9X_5X_7X_8X_9C$ (SEQ ID NO:10)
$CX_5X_6X_7X_8X_9X_5X_6X_7X_8X_9X_{11}X_{12}C$ (SEQ ID NO:11)
$CX_5X_6X_7X_8X_9X_5X_6X_7X_8X_9X_{13}X_{14}C$ (SEQ ID NO:11)
$CX_5X_6X_7X_8X_9X_5X_6X_7X_8X_9X_{16}X_{17}X_{18}X_{19}X_2C$ (SEQ ID NO: 12)
$CX_5X_6X_7X_8X_9X_{11}X_{12}X_5X_6X_7X_8X_9C$ (SEQ ID NO:13)
$CX_5X_6X_7X_8X_9X_{11}X_{12}X_{11}X_{12}C$ (SEQ ID NO:14)
$CX_5X_6X_7X_8X_9X_{11}X_{12}X_{13}X_{14}C$ (SEQ ID NO:161)
$CX_5X_6X_7X_8X_9X_{11}X_{12}X_{16}X_{17}X_{18}X_{19}X_{20}C$ (SEQ ID NO:15)
$CX_5X_6X_7X_8X_9X_{13}X_{14}X_5X_6X_7X_8X_9C$ (SEQ ID NO:13)
$CX_5X_6X_7X_8X_9X_{13}X_{14}X_{11}X_{12}C$ (SEQ ID NO:161)
$CX_5X_6X_7X_8X_9X_{13}X_{14}X_{13}X_{14}C$ (SEQ ID NO:14)
$CX_5X_6X_7X_8X_9X_{13}X_{14}X_{16}X_{17}X_{18}X_{19}X_{20}C$ (SEQ ID NO:15)
$CX_5X_6X_7X_8X_9X_{16}X_{17}X_{18}X_{19}X_{20}X_5X_6X_7X_8X_9C$ (SEQ ID NO:16)
$CX_5X_6X_7X_8X_9X_{16}X_{17}X_{18}X_{19}X_{20}X_{11}X_{12}C$ (SEQ ID NO:15)
$CX_5X_6X_7X_8X_9X_{16}X_{17}X_{18}X_{19}X_{20}X_{13}X_{14}C$ (SEQ ID NO:15)
$CX_5X_6X_7X_8X_9X_{16}X_{17}X_{18}X_{19}X_{20}X_{16}X_{17}X_{18}X_{19}X_{20}$ (SEQ ID NO:17)
$CX_{11}X_{12}X_5X_6X_7X_8X_9X_5X_6X_7X_8X_9C$ (SEQ ID NO:18)
$CX_{11}X_{12}X_5X_6X_7X_8X_9X_{11}X_{12}C$ (SEQ ID NO:19)
$CX_{11}X_{12}X_5X_6X_7X_8X_9X_{13}X_{14}C$ (SEQ ID NO:161)
$CX_{11}X_{12}X_5X_6X_7X_8X_9X_{16}X_{17}X_{18}X_{19}X_{20}C$ (SEQ ID NO:15)
$CX_{11}X_{12}X_{11}X_{12}X_5X_6X_7X_8X_9C$ (SEQ ID NO:20)
$CX_{11}X_{12}X_{11}X_{12}X_{11}X_{12}C$ (SEQ ID NO:21)
$CX_{11}X_{12}X_{11}X_{12}X_{13}X_{14}C$ (SEQ ID NO:22)
$CX_{11}X_{12}X_{11}X_{12}X_{16}X_{17}X_{18}X_{19}X_{20}C$ (SEQ ID NO:20)
et cetera Produced peptides are subsequently preferably coupled to a scaffold in order to generate a (test) compound according to the present invention. Preferably, a plurality of different peptides are coupled to scaffolds in order to produce a plurality of test compounds.

It will be evident that further combinations of three flanking sequences are possible in the above mentioned schematic example. Moreover, other peptides comprising more than three flanking sequences can be designed. However, the total length of the peptides does preferably not exceed 50 amino acid residues.

Furthermore, various embodiments of the invention involve the selection of flanking sequences of various different lengths. For instance in the above mentioned schematic example the following flanking sequences of $X_{10}$ are for instance selected:

$X_1X_2X_3X_4X_5X_6X_7X_8X_9$ and/or
$X_2X_3X_4X_5X_6X_7X_8X_9$ and/or
$X_3X_4X_5X_6X_7X_8X_9$ and/or
$X_4X_5X_6X_7X_8X_9$ and/or
$X_5X_6X_7X_8X_9$ and/or
$X_6X_7X_8X_9$ and/or
$X_7X_8X_9$ and/or
$X_8X_9$ and/or
$X_9$ and/or
$X_{11}X_{12}X_{13}$ and/or
$X_{11}X_{12}$ and/or
$X_{11}$ By varying the kind, length and amount of flanking sequences, peptides of different kinds and/or lengths are produced. Preferably, peptides between 4-25 amino acid residues are generated.

The number of selected amino acid residues of a given proteinaceous molecule is variable and depends on a particular application. In one preferred embodiment at least two amino acid residues are selected. A method according to the invention is thus provided wherein at least two amino acid residues within the primary sequence of said at least one proteinaceous molecule are selected. In view of efficacy, at most five amino acid residues are preferably selected. Preferably, three or four amino acid residues are selected. In a particularly preferred embodiment two amino acid residues are selected.

It is of course also possible to perform a method of the invention with one selected amino acid residue of a proteinaceous molecule. In that case a peptide of the invention comprises at least one flanking sequence of said one selected amino acid residue that is located in the direction of the N-terminus of said proteinaceous molecule and/or at least one flanking sequence of said one selected amino acid residue that is located in the direction of the C-terminus of said proteinaceous molecule. Of course, as outlined above, various flanking sequences of different length can be used.

The number and length of selected flanking sequences depends on a particular application. In one preferred embodiment a peptide is produced which comprises at least two flanking sequences. Said flanking sequences may be different from each other, or they may be the same. In one embodiment at least two flanking sequences of the same selected amino acid residue are incorporated into a peptide. In another embodiment however a peptide is produced which comprises a flanking sequence of a first selected amino acid residue and a flanking sequence of a second selected amino acid residue.

In a method according to the invention a peptide is produced which peptide comprises at least two groups capable of reacting with a scaffold. In a preferred embodiment said groups comprise at least one SH-group, preferably at least one cysteine residue, because a SH-group is particularly suitable for coupling a peptide to a scaffold comprising a (hetero)aromatic molecule. The use of a scaffold comprising a (hetero)aromatic molecule (preferably comprising at least one benzylic halogen substituent) is preferred, as already outlined above. If a group comprising at least one SH-group (for instance a cysteine residue) is used in a coupling reaction of a peptide with a scaffold, it is preferred that said peptide is at least in part devoid of other available cysteine residues. An available cysteine (residue) is defined as a cysteine whose SH-group is capable of reacting with another group. Hence, cysteine residues whose SH-group is not capable of reacting with another group, for instance because they are provided with a protecting group, are not covered by the term "available cysteine". If a peptide of the invention comprises other available cysteines, such other available cysteines could react with the scaffold instead of said at least one group that was intended to react with said scaffold. This way, unintended bonds between said peptide and said scaffold could be formed. Furthermore, said other available cysteines could form a disulfide bond with said group comprising an SH-group that was intended to react with said scaffold. In that case a coupling reaction between said peptide and said scaffold could also be distorted. These problems are at least in part avoided when at least one cysteine residue present in a flanking region is replaced by a group that is incapable of forming a bond with other sulfhydryl group-containing moieties. In one embodiment this is performed with protecting groups or mimetics. For instance, a cysteine that is protected with a removable protecting group, such as for instance a Cys(StBu) or, most preferably, a cysteine-(acetamidomethyl) group (Cys (Acm)), is used. Following attachment of a peptide of the invention to a scaffold to yield a compound of the invention, the protecting group is easily removed, for instance by reductive treatment. For instance, 1,4-DDT or ethane dithiol is used. It is also possible to replace a cysteine residue of a flanking sequence by a bioisosteric unit. A bioisosteric unit is defined as a functionality having similar size and physicochemical properties.

Most preferably at least one cysteine in at least one of said flanking sequences is replaced by another amino acid residue that is unreactive with the scaffold, for example an alanine residue. Provided is thus a method according to the invention wherein at least one cysteine in at least one of said flanking sequences is replaced by another amino acid residue. Most preferably all cysteines in all flanking sequences that are incorporated into a peptide are replaced by other amino acid residues that are unreactive with the scaffold that is used, in order to prevent attachment of said peptide to the scaffold via a group other than the two groups having a SH group that are intended to bind to the scaffold.

In one preferred embodiment peptides of various different length are synthesised in order to provide a more diverse collection of potential binding compounds and/or immunogenic compounds. Interactions between binding molecules and immunogenic interactions are often very specific. Hence, not only the sequence of a peptide of the invention but also its length is often relevant if a screen for a specific interaction is performed. Provided is therefore a method according to the invention comprising producing at least two peptides of different length. Most preferably, a plurality of peptides with a length of between 6 and 25 amino acid residues is generated. If the secondary, tertiary and/or quaternary structure of a proteinaceous molecule of interest is known, it is furthermore preferred to select at least one amino acid residue from a surface-exposed region of said proteinaceous molecule.

If however the secondary, tertiary and/or quaternary structure of a proteinaceous molecule of interest is not, or only partly, known it is preferred to perform a preliminary screening. In that case a plurality of overlapping peptides is preferably synthesised which peptides have essentially the same length. Preferably 2, 3 or 4 sets of peptides are synthesised, wherein one set of peptides comprises peptides of about the same length. For instance, two sets of peptides are produced wherein one set comprises peptides with a length of about 8 amino acid residues and wherein the other set comprises peptides with a length of about 15 amino acid residues. According to this embodiment, said plurality of overlapping peptides (which is preferably coupled to a scaffold) is tested for a desired functionality (for instance their capability of binding to a binding compound of interest such as for example an antibody, T cell, ligand or receptor). If one or more peptides are found to be promising candidates, it is preferably determined from which region(s) of said proteinaceous molecule said promising candidates appear to be derived. Once said region(s) of said proteinaceous molecule is/are identified, a second procedure is preferably followed. In this second procedure a method of the invention is performed again. This time at least one amino acid residue is selected which is present in at least one of the above-mentioned region(s) identified in the first procedure.

In one embodiment a peptide which appears to be a promising candidate is combined with a second peptide (with formula $(X)_y$). Said second peptide is preferably at least in part derived from the same proteinaceous molecule. For instance, if two cysteine residues are used as groups that are capable of reacting with a scaffold, and if a promising peptide found during a screening is depicted as $(X)_x$, peptides with the formula $C(X)_xC(X)_y$ and/or $(X)_xC(X)_yC$ are preferably synthesised. In this formula C is a cysteine residue, $(X)_x$ represents at least one flanking sequence and $(X)_y$ represents any sequence derived from said at least one proteinaceous molecule. Preferably, $(X)_x$ and $(X)_y$ each represent at least one flanking sequence.

The resulting peptides are once again preferably coupled to a scaffold in order to produce stable test compounds according to the present invention. Said test compounds are preferably screened again for a desired functionality (for instance their capability of binding to a binding compound of interest such as for example an antibody, T cell, ligand or receptor). Preferably, said test compounds are tested for the same functionality as compared to a first screening during which the promising peptide $(X)_x$ was selected. This embodiment of the invention is particularly suitable for producing and/or identifying an immunogenic compound and/or a binding compound that is at least in part derived from a proteinaceous molecule whose secondary, tertiary and/or quaternary structure is not, or only partly, known. According to one embodiment, 2, 3 or 4 sets of peptides are synthesised, wherein one set of peptides comprises peptides of about the same length, and the resulting peptides are subjected to a first screening assay using a binding molecule of interest. Peptides which appear to be promising candidates are subsequently coupled to a second peptide which is also derived from said proteinaceous molecule whose secondary, tertiary and/or quaternary structure is not, or only partly, known in order to generate compounds with the formula $C(X)_xC(X)_y$ and/or $(X)_xC(X)_yC$. The resulting peptides are subsequently screened again with a second screening assay using a binding molecule of interest.

One embodiment thus provides a method according to the invention wherein a peptide is produced that comprises the format $C(X)_xC(X)_y$ or $C(X)_yC(X)_x$ and wherein C is a cysteine residue, $(X)_x$ represents at least one of said flanking sequences and $(X)_y$ represents any sequence derived from said at least one proteinaceous molecule. Preferably, $(X)_x$ and $(X)_y$ each represent at least one of said flanking sequences.

Overlapping peptides are defined herein as peptides derived from a primary sequence of a proteinaceous molecule, wherein each peptide has at least one amino acid residue of said primary sequence in common with another peptide. For instance, a plurality of peptides of length n are produced, wherein the first peptide starts at position 1 and ends at position n of the primary sequence of said proteinaceous molecule. The second peptide starts at position 2 and ends at position n+1 of the primary sequence of said proteinaceous molecule. The third peptide starts at position 3 and ends at position n+2 of the primary sequence of said proteinaceous molecule, et cetera. Peptides which have essentially the same length are defined herein as peptides whose amounts of amino acid residues differ at most 5 amino acid residues from each other. Preferably, said peptides have exactly the same amount of amino acid residues.

A peptide according to the invention preferably comprises at least two groups capable of reacting with a scaffold. If a peptide of the invention has two groups capable of reacting with a scaffold, a scaffold is preferably used which has two sites suitable for binding. The phrases "sites suitable for binding" and "binding sites" are used herein interchangeably and are defined as sites that are capable of binding a group capable of reacting with a scaffold, which group is present on a peptide according to the invention. Said group is preferably a SH functionality, which is preferably used for a nucleophilic substitution reaction. An example of a suitable binding site of a scaffold is therefore a saturated carbon which is bonded to a heteroatom which heteroatom is more electronegative than carbon.

An example of a scaffold comprising two binding sites is an aromatic molecule comprising two halogen substituents. Preferably a bis(bromomethyl)benzene, a (bromomethyl)(chloromethyl)benzene or a bis(chloromethyl)benzene is used. Most preferably, meta-dibromoxyleen (m-T2) is used.

In one embodiment a peptide according to the invention is produced which comprises at least three groups capable of reacting with a scaffold. This embodiment provides the advantage that at least two loops are formed by a peptide of the invention which is bound to a scaffold at three sites. Each of said at least two loops is suitable for testing for the presence of a continuous binding site and/or immunogenic site. Preferably however at least two loops are tested together in order to search for the presence of a discontinuous binding site and/or immunogenic site. In a preferred embodiment each loop comprises at least part of a flanking sequence, so that the characteristics of various (parts of) flanking sequences are tested simultaneously. Hence, a peptide of the invention preferably comprises at least two flanking sequences and at least three groups capable of reacting with a scaffold. Preferably said at least three groups capable of reacting with a scaffold are cysteine residues. A method according to the invention is therefore provided wherein said peptide comprises at least three cysteine residues and at least two flanking sequences.

Of course, if a peptide of the invention contains three groups capable of reacting with a scaffold, a scaffold is preferably used which has (at least) three sites suitable for binding. For instance an aromatic molecule comprising three halogen substituents is used. Said aromatic molecule preferably comprises a tris(bromomethyl)benzene, a bis(bromomethyl)(chloromethyl)benzene, a (bromomethyl)bis(chloromethyl)benzene or a tris(chloromethyl)benzene. Most preferably, 2,4,6-tris(bromomethyl)mesitylene (T3) is used.

Likewise, if a peptide of the invention contains four groups capable of reacting with a scaffold, a scaffold is preferably used which has four sites suitable for binding. An aromatic molecule comprising four halogen substituents is preferably used. Said aromatic molecule preferably comprises a tetra (bromomethyl)benzene, a tris(bromomethyl)(chloromethyl) benzene, a bis(bromomethyl)bis(chloromethyl)benzene, a (bromomethyl)tris(chloromethyl)benzene or a tetra (chloromethyl) benzene. Most preferably, 1,2,4,5 tetrabromodurene (T4) is used.

In one preferred embodiment a peptide with the formula $C(X)_xC(X)_yC$ or $C(X)_yC(X)_xC$ is produced. In this formula, C is a group capable of reacting with a scaffold, preferably a cysteine residue, $(X)_x$ represents at least one flanking sequence and $(X)_y$ represents any sequence derived from a proteinaceous molecule of interest. $(X)_y$ is preferably derived from the same proteinaceous molecule as $(X)_x$. Preferably, $(X)_x$ and $(X)_y$ each represent at least one flanking sequence. In one embodiment the length of $(X)_x$ and $(X)_y$ is about the same, meaning that the difference between the amount of amino acid residues of $(X)_x$ and the amount of amino acid residues of $(X)_y$ is five or less. If such peptides are bound to a scaffold, two loops of essentially the same length are produced. This is however not necessary: in another embodiment the length of $(X)_x$ and $(X)_y$ are significantly different from each other, meaning that the amount of amino acid residues of $(X)_x$ and the amount of amino acid residues of $(X)_y$ differ from each other by more than five amino acid residues. If such peptide is coupled to a scaffold, two loops of significantly different length is obtained.

A peptide with the above-mentioned formula, containing three groups capable of reacting with a scaffold, is preferably coupled to a scaffold with three binding sites. Said peptide is preferably coupled to an aromatic molecule comprising three halogen substituents, more preferably to a tris(bromomethyl) benzene, most preferably to 2,4,6-tris(bromomethyl)mesitylene (T3). This for instance results in a structure as depicted in FIG. 7, which is particularly suitable for testing two peptide loops on one scaffold.

A peptide with the formula $C(X)_xC(X)_yC$ or $C(X)_yC(X)_xC$ is produced in a variety of embodiments. In one embodiment various flanking sequences of a proteinaceous molecule of interest are selected, and said flanking sequences are randomly combined in order to yield peptides with the formula $C(X)_xC(X)_yC$ or $C(X)_yC(X)_xC$ wherein $(X)_x$ and $(X)_y$ both comprise at least one flanking sequence. Said flanking sequences are preferably selected from at least one surface-exposed region of a proteinaceous molecule of interest. In another embodiment, a method of the invention is firstly performed in order to produce a plurality of peptides. Said plurality of peptides is screened with a binding molecule of interest, such as for instance an antibody and/or T cell, in order to identify, at least one promising candidate peptide of the formula $(X)_x$ with a desired immunogenic and/or binding property. Said promising candidate peptide is subsequently combined with another peptide with the formula $(X)_y$ in order to obtain a peptide with the formula $C(X)_xC(X)_yC$ or $C(X)_yC(X)_xC$. Said peptide with the formula $(X)_y$ is preferably derived from the same proteinaceous molecule as said promising candidate peptide of the formula $(X)_x$. In one preferred embodiment a plurality of peptides with the formula $(X)_y$ is produced comprising overlapping peptides which are at least in part derived from the same proteinaceous molecule as said promising candidate peptide of the formula $(X)_x$. Each peptide $(X)_y$ comprising an overlapping peptide is subsequently coupled to a promising candidate peptide of the formula $(X)_x$. The resulting peptides $C(X)_xC(X)_yC$ or $C(X)_yC(X)_xC$ are subsequently screened again, preferably in the same kind of screening assay during which promising candidate peptide of the formula $(X)_x$ was selected. If at least one peptide $C(X)_xC(X)_yC$ or $C(X)_yC(X)_xC$ appears to have a desired immunogenic property and/or binding property, said peptide is selected.

If a peptide with the formula $C(X)_xC(X)_yC$ or $C(X)_yC(X)_xC$ is at least in part derived from a transmembrane protein, peptides $(X)_x$ and $(X)_y$ are preferably both derived from an extracellular loop domain of said transmembrane protein and/or from the free N-terminus. The free N-terminus of a transmembrane protein is defined herein as the linear N-terminal part of said protein, starting at amino acid 1 and ending at the first amino acid residue of the first transmembrane domain (mostly a transmembrane helix). In one embodiment, a method of the invention is firstly performed wherein at least one amino acid residue present in an extracellular loop domain and/or the free N-terminus of a transmembrane protein is selected. According to this embodiment, produced peptides comprising at least one flanking sequence present in said extracellular loop domain and/or in said free N-terminus are screened with a binding molecule of interest, such as for instance an antibody and/or T cell, in order to identify at least one promising candidate peptide of the formula $(X)_x$ with a desired immunogenic and/or binding property. Said promising candidate peptide is subsequently combined with another peptide with the formula $(X)_y$ comprising at least one flanking sequence from an extracellular loop domain and/or the free N-terminus of said transmembrane protein in order to obtain a peptide with the formula $C(X)_xC(X)_yC$ or $C(X)_yC(X)_xC$. In one embodiment $(X)_x$ and $(X)_y$ comprise at least one flanking sequence derived from the same extracellular loop domain and/or free N-terminus. Alternatively, or additionally, $(X)_x$ and $(X)_y$ comprise at least one flanking sequence derived from different domains of said transmembrane protein.

If a peptide with the formula $C(X)_xC(X)_yC$ or $C(X)_yC(X)_xC$ is at least in part derived from a proteinaceous molecule comprising at least two internal cystine bonds between cysteine residues, such as a member of the cys-knot superfamily, peptides $(X)_x$ and $(X)_y$ preferably both comprise at least one flanking sequence of one or more cysteine residues of said proteinaceous molecule. Preferably, a method of the invention is performed wherein only cysteine residues of said proteinaceous molecule are selected. As a result, peptides are produced that comprise only (combinations of) flanking sequences of at least one cysteine residue.

If the (secondary, tertiary and/or quaternary) structure of a proteinaceous molecule of interest is not known, a set of overlapping peptides is preferably generated. In one embodiment, three groups capable of reacting with a scaffold are placed at three sites within each overlapping peptide. The resulting peptide is subsequently preferably coupled to a scaffold comprising (at least) three binding sites in order to provide a test compound according to the invention. In a preferred embodiment one group capable of reacting with a scaffold is placed at the first amino acid residue of an overlapping peptide, one group capable of reacting with a scaffold is placed at the last amino acid residue of said overlapping peptide and one group capable of reacting with a scaffold is placed between said first and said last group capable of reacting with a scaffold. Since said groups capable of reacting with a scaffold are preferably cysteine residues, a peptide is preferably produced with the formula $C(X)_xC(X)_yC$ wherein $(X)_x$ and $(X)_y$ are preferably part of the same overlapping peptide. This peptide $C(X)_xC(X)_yC$ is preferably produced by replacing the first amino acid residue of the sequence of an overlapping peptide, the last amino acid residue of the sequence of said overlapping peptide and one amino acid residue located in between said first and last amino acid residues by a cysteine. Alternatively, $(X)_x$ and $(X)_y$ each comprise an overlapping peptide. In one embodiment $(X)_x$ and $(X)_y$ contain about the same amount of amino acid residues. In that case, a set of overlapping peptides consisting of n amino acid residues is preferably produced, wherein n is an odd number. Subsequently, amino acid residues 1, (n+1)/2 and n are replaced by cysteine. Other available cysteine residues are preferably either replaced by another amino acid residue or rendered inactive (for instance by a protective group) so that said other available cysteine residues do not interfere with the coupling reaction between said peptide and a scaffold. The resulting peptides, $C(X)_xC(X)_yC$, are subsequently preferably coupled to a scaffold comprising (at least) three binding sites and subsequently tested for a desired characteristic.

In a further embodiment, a peptide with the formula $C(X)_xC(G)_nC(X)_yC$ or $C(X)_yC(G)_nC(X)_xC$ is produced. In this formula, C represents a group capable of reacting with a scaffold, preferably a cysteine residue, $(G)_n$ represents a spacer, $(X)_x$ represents at least one flanking sequence and $(X)_y$ represents any sequence derived from at least one proteinaceous molecule. Preferably, $(X)_x$ and $(X)_y$ each represent at least one flanking sequence of the same proteinaceous molecule of interest.

Of course, it is also possible to replace the spacer by another flanking sequence $(X)_z$. In that case a peptide with formula $C(X)_xC(X)_zC(X)_yC$, $C(X)_xC(X)_yC(X)_zC$, $C(X)_yC(X)_zC(X)_xC$, $C(X)_yC(X)_xC(X)_zC$, $C(X)_zC(X)_xC(X)_yC$ and/or $C(X)_zC(X)_yC(X)_xC$ is produced.

Peptides with the above mentioned formulae are particularly suitable for coupling to a scaffold comprising (at least) four binding sites, or to two scaffolds wherein each scaffold comprises (at least) two binding sites. Non-limiting schematic examples of resulting compounds are depicted in FIGS. 7 and 8.

If two scaffolds with at least two binding sites are used, such as for instance two separate m-P2 molecules, it is sometimes desired to regulate which cysteine residues are coupled to the first scaffold and which cysteine residues are coupled to the second scaffold. For instance, if a peptide with the formula $C_1(X)_xC_2(G)_nC_3(X)_yC_4$ is used, $C_1$ and $C_2$ are often intended to bind a first scaffold, whereas $C_3$ and $C_4$ are intended to bind a second scaffold. This is for instance performed by providing two cysteine residues that are intended to bind to a second scaffold (for instance $C_3$ and $C_4$) with a protecting group such as for instance methoxytrityl (Mmt) or trityl (Trt). In a first coupling reaction, a peptide comprising protected $C_3$ and $C_4$ is incubated with a first scaffold. Only $C_1$ and $C_2$ are now capable of binding the scaffold. Subsequently, $C_3$ and $C_4$ are deprotected. The resulting complex is now incubated with a second scaffold, which may be the same kind of scaffold as said first scaffold (although this is not necessary; said second scaffold and said first scaffold may as well be different from each other). This time, $C_3$ and $C_4$ are capable of binding with said second scaffold. This way, $C_1$ and $C_2$ are bound to the first scaffold, and $C_3$ and $C_4$ are bound to the second scaffold. Of course, other combinations are possible.

If a peptide with the formula $C(X)_xC(G)_nC(X)_yC$, $C(X)_yC(G)_nC(X)_xC$, $C(X)_xC(X)_zC(X)_yC$, $C(X)_xC(X)_yC(X)_zC$, $C(X)_yC(X)_zC(X)_xC$, $C(X)_yC(X)_xC(X)_zC$, $C(X)_zC(X)_xC(X)_yC$ or $C(X)_zC(X)_yC(X)_xC$ is at least in part derived from a transmembrane protein, peptides $(X)_x$ and $(X)_y$ and optionally $(X)_z$ are preferably derived from an extracellular loop domain of said transmembrane protein and/or from the free N-terminus. In one embodiment, a method of the invention is performed wherein at least one promising peptide with the formula $(X)_x$ is selected during a first screening method as described above, which peptide with the formula $(X)_x$ comprises at least one flanking sequence derived from an extracellular loop domain and/or the free N-terminus of a transmembrane protein. Said promising peptide of the formula $(X)_x$ is subsequently combined with another peptide with the formula $(X)_y$ and/or with another peptide with the formula $(X)_z$ in order to obtain a peptide with a formula selected from the group consisting of $C(X)_xC(G)_nC(X)_yC$, $C(X)_yC(G)_nC(X)_xC$, $C(X)_xC(X)_zC(X)_yC$, $C(X)_xC(X)_yC(X)_zC$, $C(X)_yC(X)_zC(X)_xC$, $C(X)_yC(X)_xC(X)_zC$, $C(X)_zC(X)_xC(X)_yC$ and $C(X)_zC(X)_yC(X)_xC$. In one embodiment $(X)_x$ and $(X)_y$ and, optionally, $(X)_z$ comprise at least one flanking sequence derived from the same extracellular loop domain and/or from the free N-terminus. Alternatively, or additionally, $(X)_x$ and $(X)_y$ and, optionally, $(X)_z$ comprise at least one flanking sequence derived from a different domain of said transmembrane protein.

If a peptide with a formula selected from the group consisting of $C(X)_xC(G)_nC(X)_yC$, $C(X)_yC(G)_nC(X)_xC$, $C(X)_xC(X)_zC(X)_yC$, $C(X)_xC(X)_yC(X)_zC$, $C(X)_yC(X)_zC(X)_xC$, $C(X)_yC(X)_xC(X)_zC$, $C(X)_zC(X)_xC(X)_yC$ and $C(X)_zC(X)_yC(X)_xC$ is at least in part derived from a proteinaceous molecule comprising at least two internal cystine bonds between cysteine residues, such as for instance a member of the cys-knot superfamily, peptides $(X)_x$ and $(X)_y$ and, optionally, $(X)_z$ preferably comprise at least one flanking sequence of one or more cysteine residues of said proteinaceous molecule. Preferably, a method of the invention is performed wherein only cysteine residues of said proteinaceous molecule are selected. As a result, peptides are produced that comprise only (combinations of) flanking sequences of at least one cysteine residue. In one preferred embodiment peptides are generated which comprise at least one flanking sequence of at least two cysteine residues of said proteinaceous molecule. Most preferably peptides are generated which comprise at least two flanking sequences of at least two cysteine residues of said proteinaceous molecule.

In one preferred embodiment a method according to the invention is performed as follows. A plurality of peptides is produced comprising a first cysteine Cys-1 of a SS-bridge of a proteinaceous molecule, a flanking sequence $(X)_x$ of said Cys-1 which flanking sequence is located in the direction of the C-terminus and has a length of x amino acid residues, followed by a second cysteine C, followed by n glycine residues $(G)_n$, followed by a third cysteine C, followed by a flanking sequence $(X)_y$ of the second cysteine residue Cys-2 of said SS-bridge which flanking sequence is located in the direction of the N-terminus and has a length of y amino acid residues, followed by the second cysteine Cys-2 of said SS-bridge. The resulting peptide contains the formula Cys-1$(X)_x$C$(G)_n$C$(X)_y$Cys-2. A plurality of different peptides is preferably synthesized wherein 0 is smaller than or equal to x, n, and y and wherein x, n, and y are smaller than or equal to 6. Additionally, x+n+y is preferably smaller than or equal to 21, so that the resulting peptide is smaller than or equal to 25 amino acid residues. Produced peptides are subsequently preferably screened for a desired immunogenic characteristic and/or binding property. This is preferably performed after coupling of said peptide to a scaffold comprising (at least) four binding sites or to two scaffolds, each comprising (at least) two binding sites. Most preferably, said peptide is coupled to a T4 scaffold or to two T2 scaffolds. If two scaffolds are used, each scaffold comprising (at least) two binding sites, the two cysteine residues Cys-1 and Cys-2 are preferably coupled to the same scaffold in order to form a loop. The other two cysteine residues are preferably coupled to another scaffold in order to form a loop. As already explained hereinbefore, this is for instance accomplished by providing Cys-1 and Cys-2 with a protecting group while leaving the other two cysteine residues unprotected. In that case, the unprotected cysteine are coupled to a scaffold in order to form a loop. Subsequently, Cys-1 and Cys-2 are deprotected and coupled to another scaffold.

It is also possible to provide Cys-1 and Cys-2 with a first kind of protecting group, such as for instance Trt, and to provide the other two cysteine residues with a second kind of protecting group, such as for instance Mmt. Both kind of protecting groups are removed using different reagentia. This way, it is possible to determine what cysteine residues are capable of binding to a scaffold.

In a further embodiment a peptide with the formula C$(X)_x$C$(X)_m$(G)$_n$$(X)_p$C$(X)_y$C is produced. In this formula, C represents a group capable of reacting with a scaffold, preferably a cysteine residue, $(G)_n$ represents a spacer, and $(X)_x$, $(X)_m$, $(X)_p$ and $(X)_y$ each represent at least one flanking sequence of a proteinaceous molecule of interest. This peptide is particularly suitable for coupling to two scaffolds, wherein each scaffold comprises (at least) two binding sites.

In a preferred embodiment, a peptide of this formula is synthesized using flanking sequences of a proteinaceous molecule of interest that comprises (at least) two SS-bridges, wherein in the primary sequence of said proteinaceous molecule the first cysteine of the second SS-bridge is located N-terminally from the second cysteine of the first SS-bridge, wherein said first cysteine of the second SS-bridge and said second cysteine from the first SS-bridge are preferably located within 6 amino acid residues from each other, and wherein the position of each cysteine of said SS-bridges within the primary sequence of said proteinaceous molecule is known. Hence, if the first cysteine of the second SS-bridge is located at position n, the second cysteine from the first SS-bridge is preferably located at position n+1, n+2, n+3, n+4, n+5 or n+6. According to this embodiment, a plurality of peptides is produced comprising the first cysteine Cys-1.1 of the first SS-bridge, a flanking sequence $(X)_x$ of said Cys-1.1 which flanking sequence is located in the direction of the C-terminus and has a length of x amino acid residues, followed by the first cysteine Cys-1.2 of the second SS-bridge, followed by a flanking sequence $(X)_m$ of said Cys-1.2 which flanking sequence is located in the direction of the C-terminus and has a length of m amino acid residues, followed by n glycine residues $(G)_n$, followed by a flanking sequence of the third cysteine residue present in said primary sequence—which may either be the second cysteine of the first SS-bridge (Cys-2.1) or the second cysteine of the second SS-bridge (Cys-2.2)—which flanking sequence is located in the direction of the N-terminus and has a length of p amino acid residues, followed by said third cysteine residue, followed by a flanking sequence of the fourth cysteine residue present in said primary sequence which flanking sequence is located in the direction of the C-terminus and has a length of y amino acid residues, followed by the fourth cysteine residue present in said primary sequence, which may either be the second cysteine of the first SS-bridge (Cys-2.1) or the second cysteine of the second SS-bridge (Cys-2.2). The resulting peptide contains the formula

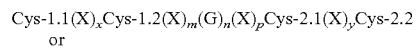

or

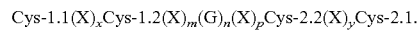

A plurality of different peptides is preferably synthesized wherein 0 is smaller than or equal to x, m, n, p and y and wherein x, m, n, p and y are smaller than or equal to 6. Additionally, x+m+n+p+y is preferably smaller than or equal to 21, so that the resulting peptides are smaller than or equal to 25 amino acid residues. Produced peptides are subsequently preferably screened for a desired immunogenic characteristic and/or binding property. This is preferably performed after coupling of said peptide to a scaffold comprising (at least) four binding sites or to two scaffolds, each comprising (at least) two binding sites. Most preferably, said peptide is coupled to a T4 scaffold or to two T2 scaffolds. If two scaffolds are used, each scaffold comprising (at least) two binding sites, the two cysteine residues of the first SS-bridge are preferably coupled to the same scaffold in order to form a loop. The two cysteine residues of the second SS-bridge are preferably coupled to another scaffold in order to form a loop. This is preferably performed as already explained hereinbefore. For instance, the two cysteine residues of the first SS-bridge are provided with a protecting group while the other two cysteine residues are kept unprotected. In that case, the unprotected cysteine are coupled to a scaffold in order to form a loop. Subsequently, the two cysteine residues of the first SS-bridge are deprotected and coupled to another scaffold.

It is also possible to provide the two cysteine residues of the first SS-bridge with a first kind of protecting group, such as for instance Trt, and to provide the other two cysteine residues with a second kind of protecting group, such as for instance Mmt. Both kind of protecting groups are removed using different reagentia. This way, it is possible to determine what cysteine residues are capable of binding to a scaffold.

In a further embodiment a peptide with the formula $C(X)_m(G)_n(X)_pC(X)_q(G)_r(X)_sC(X)_t(G)_u(X)_vC$ is produced. In this formula, C represents a group capable of reacting with a scaffold, preferably a cysteine residue, $(G)_n$, $(G)_r$ and $(G)_q$ represent a spacer and $(X)_m$, $(X)_p$, $(X)_q$, $(X)_s$, $(X)_t$ and $(X)_v$ each represent at least one flanking sequence. This peptide is provided with three spacers, allowing for flexible loops within said peptide. A peptide according to this formula is also particularly suitable for coupling to two scaffolds, wherein each scaffold comprises (at least) two binding sites.

In a preferred embodiment, a peptide according to this formula is synthesized using flanking sequences of a proteinaceous molecule of interest that comprises (at least) two SS-bridges, wherein the position of each cysteine of said SS-bridges within the primary sequence of said proteinaceous molecule is not exactly known and wherein in the primary sequence of said proteinaceous molecule two cysteine residues are located within 6 amino acid residues from each other. In this case, one does not know beforehand whether the first cysteine of a second SS-bridge is located N-terminally or C-terminally from the second cysteine of a first SS-bridge. It is therefore preferred to synthesize a plurality of molecules of the above mentioned formula, said plurality of peptides comprising different combinations of cysteines and flanking sequences, in order to screen for a peptide with a desired binding property and/or immunogenic property. A method according to the present invention preferably comprises selecting cysteine residues of SS-bridges, and flanking sequences thereof, because an SS-bridge between cysteines of a proteinaceous molecule often results in an internal loop. Such loop is regularly found to be involved in interaction between said proteinaceous molecule and another compound. Hence, flanking sequences of cysteine residues of SS-bridges have an increased chance of being involved with binding events and/or immunity as compared to other sequences within a proteinaceous molecule of interest.

In one preferred embodiment a plurality of peptides is produced comprising a first cysteine $(C_1)$ found in a primary sequence, a flanking sequence $(X)_m$ of said $C_1$ which flanking sequence is located in the direction of the C-terminus and has a length of m amino acid residues, followed by n glycine residues $(G)_n$ followed by a flanking sequence $(X)_p$ of a third cysteine $(C_3)$ found in a primary sequence, which flanking sequence is located in the direction of the N-terminus and has a length of p amino acid residues, followed by $C_3$, followed by a flanking sequence $(X)_q$ of $C_3$, which flanking sequence is located in the direction of the C-terminus and has a length of q amino acid residues, followed by r glycine residues $(G)_r$, followed by a flanking sequence of a second cysteine residue $(C_2)$ present in said primary sequence which flanking sequence is located in the direction of the N-terminus and has a length of s amino acid residues, followed by $C_2$—which may for instance be the second cysteine of the first SS-bridge or the first cysteine of the second SS-bridge—, followed by a flanking sequence of $C_2$ present in said primary sequence which flanking sequence is located in the direction of the C-terminus and has a length of t amino acid residues, followed by u glycine residues $(G)_u$, followed a flanking sequence of the fourth cysteine residue present in said primary sequence $(C_4)$ which flanking sequence is located in the direction of the N-terminus and has a length of v amino acid residues, followed by the fourth cysteine residue $(C_4)$. The resulting peptide is of the formula $$C_1(X)_m(G)_n(X)_pC_3(X)_q(G)_r(X)_sC_2(X)_t(G)_u(X)_vC_4$$

A plurality of different peptides is preferably synthesized wherein 0 is smaller than or equal to m, n, p, q, r, s, t, u and v and wherein m, n, p, q, r, s, t, u and v are smaller than or equal to 6. Additionally, m+n+p+q+r+s+t+u+v is preferably smaller than or equal to 21, so that the resulting peptides are smaller than or equal to 25 amino acid residues. Produced peptides are subsequently preferably screened for a desired immunogenic characteristic and/or binding property. This is preferably performed after coupling of said peptide to a scaffold comprising (at least) four binding sites or to two scaffolds, each comprising (at least) two binding sites. Most preferably, said peptide is coupled to a T4 scaffold or to two T2 scaffolds. If two scaffolds are used, each scaffold comprising (at least) two binding sites, $C_1$ and $C_3$ are preferably coupled to the same scaffold in order to form a loop. $C_2$ and $C_4$ are preferably coupled to another scaffold in order to form a loop. This is preferably performed as already explained hereinbefore. For instance, $C_1$ and $C_3$ are provided with a protecting group while the other two cysteine residues are kept unprotected. In that case, the unprotected $C_2$ and $C_4$ are coupled to a scaffold in order to form a loop. Subsequently, $C_1$ and $C_3$ are deprotected and coupled to another scaffold.

It is also possible to provide $C_1$ and $C_3$ with a first kind of protecting group, such as for instance Trt, and to provide $C_2$ and $C_4$ with a second kind of protecting group, such as for instance Mmt. Both kind of protecting groups are removed using different reagentia. This way, it is possible to determine which cysteine residues are capable of binding to a scaffold.

It is of course also possible to generate other combinations. The above mentioned embodiment is for instance modified such that the positions of $C_3$, $C_4$ and their flanking sequences within the peptide are exchanged, for instance resulting in a peptide with the formula $$C_1(X)_m(G)_n(X)_pC_4(X)_q(G)_r(X)_sC_2(X)_t(G)_u(X)_vC_3$$

A method according to the invention is in principle applicable to any proteinaceous molecule of which the primary sequence is known. In a preferred embodiment however a method according to the invention is provided wherein said proteinaceous molecule is selected from the group consisting of the cystine-knot family, transmembrane proteins, TNF-alpha, HGF-SF, FGF-beta, an interleukin, IL-5, a chemokine, a G-protein-coupled receptor, CCR4, CXCR5, IGF, LMF, endothelin-1, VIP, CGRP, PIF, EGF, TGF-alpha, the EGFR family, HER1, HER2/neu, HER3, HER4, p53, corticotrophin RF, ACTH, parathyroid hormone, CCK, substance P, NPY, GRP, neurotrophine, angiotensin-2, angiogenin, angiopoietin, neurotensine, SLCLC, SARS-derived protein, HIV-derived protein, papillomavirus-derived protein and FMDV. It has been found that a method of the invention is particularly suitable for generating immunogenic compounds and/or binding compounds that are at least partially derived from a member of said group.

If a method according to the invention involves selecting at least one amino acid residue from the primary sequence of a transmembrane protein, it is preferred to select at least one amino acid residue from an extracellular domain. However, according to the present invention optimal test results are obtained when a sequence of a transmembrane protein is taken into consideration that consists of an extracellular domain as well as three amino acid residues located N-terminally and three amino acid residues located C-terminally of such extracellular domain. Provided is therefore a method according to the invention wherein said at least one amino acid residue is selected from a sequence of at least one transmembrane protein, said sequence comprising an extracellular domain, three flanking amino acid residues located in the direction of the N-terminus of said at least one transmembrane protein, and three flanking amino acid residues located in the direction of the C-terminus of said at least one transmembrane protein.

In one particularly preferred embodiment a method of the invention is performed for producing a compound which is suitable for testing for the presence and/or identification of an immunogenic compound and/or binding compound that is at least partially derived from a member of the cystine-knot superfamily, preferably a member of the cystine-knot growth factor superfamily.

Growth factors represent a relatively large group of polypeptides which share the property of inducing cell multiplication both in vivo and in vitro. Although the level of sequence similarity between growth factors is not high, they can be classified into superfamilies based on their structural and functional similarities.

The crystal structures of four growth factors, nerve growth factor (NGF), transforming growth factor-beta (TGF-beta), platelet-derived growth factor (PDGF), and human chorionic gonadotropin (hCG) from four separate superfamilies revealed that these proteins are structurally related and share a common overall topology. These proteins show very little sequence homology, but they all have an unusual arrangement of six cysteines linked to form a "cystine-knot" conformation. The active forms of these proteins are dimers, either homo- or heterodimers. Because of their shape, there appears to be an intrinsic requirement for the cystine-knot growth factors to form dimers. This extra level of organization increases the variety of structures built around this simple structural motif.

In the crystal structures of transforming growth factor-beta 2 (TGF-beta2), platelet-derived growth factor (PDGF), nerve growth factor (NGF) and human chorionic gonadotropin (hCG), 6 conserved cysteine residues (CysI to CysVI in sequence order) form 3 disulphide bonds arranged in a knot-like topology. The two disulphide bonds between CysII and CysV ([CysII-V]) and between CysIII and CysVI ([CysIII-VI]) form a ring-like structure of 8 amino acids through which the remaining disulphide bond (between CysI and CysIV) penetrates (see FIG. 1A). The sulfur (S) atoms of the conserved cysteines I to VI that are involved in the disulphide bonds are typically referred to as S1 to S6. Cystine knot domains with more than 6 cysteine residues can be found. The "extra" cysteine residues are normally used to create further disulphide bonds within the cystine knot domain or interchain disulphide bonds, during dimerisation. However, based on homology and topology it is always possible to indicate which cysteines represent the six conserved residues CysI to CysVI (see further below).

A similar knotted arrangement of disulphide bonds has been noted in the structures of some enzyme inhibitors and neurotoxins that bind to voltage-gated $Ca^{2+}$ channels (McDonald et al. 1993, Cell 73 421-424). In those sequences, however, the cystine topology differs: Cys [III-VI] penetrates a macrocyclic ring formed by Cys [I-IV] and Cys [II-V]. Thus, cystine-knot proteins fall into 2 structural classes: growth factor type and inhibitor-like cystine knots.

The cystine-knot growth factor superfamily is divided into subfamilies, which include the glycoprotein hormones (e.g. follicle stimulating hormone (FSH)), the transforming growth factor beta (TGF-beta) proteins (e.g. bone morphogenetic protein 4), the platelet-derived growth factor-like (PDGF-like) proteins (e.g. platelet derived growth factor A), nerve growth factors (NGF) (e.g. brain-derived neurotrophic factor) (see also Table 12).

All growth factor cystine knots structures have a similar topology, with 2 distorted beta-hairpin (beta-1 and beta-3) loops "above" the knot and a single (beta-2) loop "below" the knot. The beta-1 loop is formed by the stretch of amino acids between CysI and CysII; the beta-2 loop is formed by the amino acids between CysIII and CysIV and the beta-3 loop is formed by the amino acids between CysIV and CysV (see FIG. 1A). The sizes of the hairpin loops (i.e. the number of amino acids between the indicated cysteines) can vary significantly between family members.

There are three different "fingerprints" for the Cys-knot protein family: (1) GFCYSKNOT, (2) GLYCOHORMONE, en (3) NGF. These fingerprints differ from each other primarily in (1) the number and (2) the nature of the amino acids around the Cys-knot. A fingerprint comprises characteristic features of a given protein (sub)family and can thus be used to determine whether a given protein belongs to a given protein (sub) family.

For example, "NGF" is a 4-element fingerprint that provides a signature for the nerve growth factors. The fingerprint was derived from an initial alignment of 5 sequences: the motifs were drawn from conserved regions in the C-terminal portion of the alignment, each including at least one of the 6 Cys-residues involved in disulphide bond formation. Motifs 2 and 3 span the regions encoded by PROSITE pattern NGF (PS00248; [GSR]-CysII-[KRL]-G-[LIV]-[DE]-x(3)-[YW]-x-S-x-Cys III) (SEQ ID NO:23). Amino acid between brackets indicate the possible amino acids at that position. For example, the residue N-terminal to CysII can be either Gly, Ser or Arg. An x indicates any amino acid. Two iterations using the OWL22.1 algorithm were required to reach convergence, at which point a true set comprising 28 sequences was identified. An update of STPR37_9f identified a true set of 33 sequences."

"GLYHORMONE" is a 4-element fingerprint that provides a signature for the glycoprotein hormones. The fingerprint was derived from an initial alignment of 8 sequences: the motifs were drawn from conserved regions spanning virtually the full alignment length, motifs 2 and 4 including regions encoded by PROSITE pattern GLY_HORMONE_ALPHA_1 (PS00779: CysII-x-G-C-CysIII-[FW]-S-[RQS]-A-[FY]-P-T-P) (SEQ ID NO:24), and GLY_HORMONE_ALPHA_2 (PS00780: N-H-T-x-CysV-x-CysVI-x-T-Cys-x(2)-H-K) (SEQ ID NO:25). Two iterations on OWL22.1 were required to reach convergence, at which point a true set comprising 23 sequences was identified. An update of STPR37_9f. identified a true set of 34 sequences."

"GFCYSKNOT" is "a 2-element fingerprint that provides a signature for the growth factor cystine knot family. The fingerprint was derived from an initial alignment of 25 sequences—motif 1 spans the CysII-x-G-x-CysIII (SEQ ID NO:26) consensus (cf. PROSITE patterns PDGF (PS00249: P-[PSR]-Cys-V-x(3)-R-CysII-[GSTA]-G-Cys-CysIII) (SEQ ID NO:27), TGF-BETA (PS00250: [LIVM]-x(2)-P-x(2)-[FY]-x(4)-CysII-x-G-x-CysIII) (SEQ ID NO:28), GLY_HORMONE_BETA_1 (PS00261: CysII-[STAGM]-G-[HFYL]-CysIII-x-[ST]) (SEQ ID NO:29) and NGF (PS00248; [GSR]-CysII-[KRL]-G-[LIV]-[DE]-x(3)-[YW]-x-S-x-CysIII) (SEQ ID NO:30), motif 2 spans the CysV-x-CysVI pattern. Four iterations on OWL26.0 were required to reach convergence, at which point a true set comprising 192 sequences was identified. Several false positives were also identified, most of which are highly biased (cysteine-rich)

sequences (e.g. metallothioneins and keratins). An update of STPR37_9f identified a true set of 198 sequences.

The present invention provides a method to design and produce mimics of each one of them, as well as of those family members to be discovered.

Mimicking binding sites of complex proteins, e.g. TNF-alpha, the CD (cluster of differentiation antigen)-family, cytokines, antibodies or cell surface receptors, by means of synthetic peptides is currently one of the most active areas in protein science and drug development. Many proteins exert their biological activity through interactions involving relatively small regions of their exposed surfaces. Molecules that mimic these surface epitopes are therefore of great interest, since they provide a means of mimicking the biological activity of the entire protein, for example the ability of a protein to recognize certain physiological molecules, such as proteins and DNA, in a relatively small synthetic molecule. Short linear peptides are not ideal for this purpose, because of their inherent flexibility and susceptibility to proteolytic degradation. Instead, it is preferred to constrain linear peptide chains by cyclization into a looped peptide compound with biologically relevant secondary structure(s).

The present invention provides a rationalized strategy for the design of a looped peptide structure which is suitable as a peptidomimetic of a cystine-knot growth factor family member. The term 'peptidomimetic' as used herein refers to a (synthetic) peptide compound which mimics the ability of a Cys-knot family member to recognize certain physiological molecules. The invention furthermore provides a method for producing compounds, at least partly derived from a proteinaceous molecule comprising at least one disulfide bond (for instance a member of the cystine-knot family), which compounds are suitable for testing for the presence and/or identification of an immunogenic compound and/or binding compound.

In one embodiment of the invention a proteinaceous molecule of interest comprises a disulfide bond between two cysteine residues, whereby said two cysteine residues are at least 3 and at most 21 amino acid residues located from each other in the primary sequence (meaning that the position of the first cysteine is x and the position of the second cysteine is x+n, wherein $3 =< n =< 21$). In this embodiment, at least one peptide of the following formula is preferably synthesized: $(X)_m C_x (X)_{n-1} C_{x+n} (X)_p$ wherein $C_x$ and $C_{x+n}$ represent the cysteine residues at position x and position x+n, respectively, $(X)_m$ represents a flanking sequence of $C_x$ that consists of m amino acid residues and that is located in the direction of the N-terminus, $(X)_p$ represents a flanking sequence of $C_{x+n}$ that consists of p amino acid residues and that is located in the direction of the C-terminus, and $(X)_{n-1}$ represents the n-1 amino acid residues that are located between said first and said second cysteine residues in the primary sequence of said proteinaceous molecule. In one embodiment, at least one of said amino acid residues that are located between said first and said second cysteine residues is modified, but this is not necessary.

As already explained before, $C_x$ and $C_{x+n}$ are preferably the only cysteine residues present in said peptide. Other cysteine residues in the primary sequence of said proteinaceous molecule which are part of $(X)_m$, $(X)_{n-1}$ and/or $(X)_p$ are preferably changed into another amino acid residue such as for instance alanine, or rendered inactive, for instance using protecting groups, in order to avoid interaction between such "additional" cysteine residues and $C_x$ and/or $C_{x+n}$. In a preferred embodiment a set of peptides of the formula $(X)_m C_x (X)_{n-1} C_{x+n} (X)_p$ is produced wherein the flanking sequences $(X)_m$ and $(X)_p$ are at least in part of different length. m and p preferably fulfil the formula $0 =< m$, $p =< 18$. Furthermore, m+n+p are preferably less than, or equal to, 23 in order to produce a peptide with a length of 25 amino acid residues or less. Said at least one peptide is subsequently coupled to a scaffold.

In a further embodiment of the invention a proteinaceous molecule of interest comprises a disulfide bond between two cysteine residues, whereby said two cysteine residues are more than 21 amino acid residues located from each other in the primary sequence (meaning that the position of the first cysteine is x and the position of the second cysteine is x+n, wherein n>21). In this embodiment, a part of the primary sequence of said proteinaceous molecule is preferably taken into consideration which starts at the amino acid residue at position x+[(n−20)/2] and which ends at the amino acid residue at position x+[(n+20)/2] within the primary sequence of said proteinaceous molecule. A method of the invention is thus preferably performed with said part, meaning that at least one amino acid residue of said part is selected, at least one flanking sequence thereof is selected, et cetera. One embodiment therefore provides a method according to the invention wherein at least one amino acid residues is selected from an SS-bridge sequence of said at least one proteinaceous molecule. Preferably, the two cysteines of said SS-bridge are located at position x and (x+n), wherein n>21, and said amino acid residue is preferably selected from a region of said SS-bridge sequence starting at amino acid position x+[(n−20)/2] and ending at amino acid position x+[(n+20)/2].

The following non-limiting example clarifies this embodiment. If two cysteine residues are located at position 1 and 31 of the primary sequence of a proteinaceous molecule, the following values are used: x=1, x+n=31, and n=30. Subsequently, a sequence between said two cysteine residues is considered, which starts at amino acid position 1+[(30−20)/2]=6 and which ends at amino acid position 1+[(30+20)/2]=26. Thus, the sequence between position 6 and 26 within the primary sequence of said proteinaceous molecule is taken into consideration. At least one amino acid residue from said sequence between position 6 and 26 is selected, at least one flanking sequence of said at least one selected amino acid residue is selected, et cetera. Again, preferably a plurality of peptides is generated, which peptides are preferably of different length and/or which peptides preferably comprise different flanking sequences.

If n is an odd number, the values [(n−20)/2] and [(n+20)/2] will not be integers. In that case the resulting value is round of. The first integer value is taken that is either smaller or larger than said value. For instance, if n=35, the value of [(n−20)/2] is 7.5. In that case, either the value 7 or 8 is chosen.

If a proteinaceous molecule of interest comprises more than one internal disulfide bond, wherein each disulfide bond is between two cysteine residues, a method of the invention is preferably provided wherein at least one cysteine residue is selected. The invention therefore provides a method according to the invention wherein at least one of said selected amino acid residues within the primary sequence of said at least one proteinaceous molecule is a cysteine residue. More preferably each selected amino acid residue is a cysteine residue of said proteinaceous molecule. As a consequence, in this more preferred embodiment, each selected flanking sequence is a flanking sequence of a cysteine residue. Peptides are produced comprising at least one flanking sequence of at least one cysteine residue. Preferably, different flanking sequences are combined in one peptide. In a further preferred embodiment, a plurality of peptides comprising flanking sequences of different length are produced. This embodiment is particularly useful for screening for a binding compound and/or immunogenic compound, since the flanking sequences of cysteine residues that are usually bound to each other via disulfide bonds are often involved with interaction events.

A member of the cystine-knot family comprises more than one disulfide bond. At least three disulfide bonds are present between three pairs of cysteine residues. Hence, a member of the cystine knot superfamily comprises at least six cysteine residues (CysI to CysVI in sequence order). If a member of the cystine knot family is considered as a proteinaceous molecule of interest, preferably at least two of said cysteine residues are selected in a method according to the invention. Most preferably, CysIV and CysV are selected, because these cysteine residues and the amino acid residues between them naturally form the beta-3 hairpin (B3) loop within a proteinaceous molecule. Peptides mimicking said loop are found to be particularly suitable as peptidomimetics of a member of the cystine-knot family.

Compounds that are designed and synthesized with a method according to the present invention are particularly suitable for screening for an immunogenic compound and/or binding compound of interest. In one embodiment a plurality of peptides according to the present invention is synthesized and incubated with a binding molecule of interest, such as for instance an antibody or a functional part, derivative and/or analogue thereof, and/or a T cell or a functional part, derivative and/or analogue thereof. Bound peptides are selected and/or identified. One embodiment therefore provides a method for screening for the presence and/or identity of an immunogenic compound and/or a binding compound of interest, the method comprising:

producing a plurality of compounds comprising different peptides with a method according to the invention; and testing whether at least one of said compounds is capable of specifically binding an antibody or a functional part, derivative or analogue thereof specific for said at least one proteinaceous molecule, or a T cell or a functional part, derivative or analogue thereof specific for said at least one proteinaceous molecule. Said plurality of compounds preferably comprises at least 10, more preferably at least 100, most preferably at least 1000 compounds in order to enhance the chance that a compound with a desired characteristic is present.

A functional part of an antibody or a T cell is defined as a part which has the same immunogenic properties in kind, not necessarily in amount. By immunogenic properties is meant the capability to specifically bind an antigen. A derivative of an antibody or a T cell is defined as an antibody or a T cell which has been altered such that the immunogenic properties of the resulting derivative are essentially the same in kind, not necessarily in amount. A derivative can be provided in many ways, for instance through conservative amino acid substitution.

A person skilled in the art is well able to generate analogous compounds of an antibody or a T cell. This is for instance done through screening of a peptide library. Such an analogue has essentially the same immunogenic properties of said antibody or T cell in kind, not necessarily in amount.

In one embodiment the immunogenic properties of a peptide of the invention are tested by providing a non-human animal with said compound and determining whether an immune response is elicited. Provided is therefore a method for screening for the presence and/or identity of an immunogenic compound, the method comprising:

producing a plurality of compounds comprising different peptides with a method according to the invention; and testing whether at least one of said compounds is capable of eliciting an immune response.

It is preferably tested whether a peptide of the invention is capable of eliciting an immune response against a proteinaceous molecule of interest. This is for instance performed by providing a non-human animal with a peptide of the invention, obtaining antibodies and/or T cells from said non-human animal, incubating said antibodies and/or T cells with (an epitope of) a proteinaceous molecule of interest and determining whether said antibodies and/or T cells comprise an antibody and/or T cell which is capable of specifically binding said (epitope of said) proteinaceous molecule of interest.

If a compound of the invention appears to be an immunogenic compound and/or a binding compound of interest, it is preferably selected. A method according to the invention, further comprising selecting a compound comprising an immunogenic site or a binding site of interest is therefore also herewith provided. Said selected compound is preferably identified.

In one embodiment a selected compound is directly used as an immunogenic compound and/or a binding compound. In an alternative embodiment, a selected compound is treated as a promising candidate compound. This means that further investigation is performed. In one embodiment said candidate compound is further tested after a first round of screening. For instance, if a promising candidate compound is selected during an in vitro screening method, it is for instance further tested in vivo in a non-human animal. In one embodiment said promising candidate compound is modified and tested again for the presence of at least one improved characteristic. This is for instance performed with replacement net mapping, wherein a plurality of peptides is synthesized. In each peptide at least one amino acid residue of the original promising peptide is replaced by another amino acid residue. The resulting peptides are tested again in order to determine whether at least one of the modified peptides comprises at least one improved characteristic.

In one embodiment a promising candidate peptide identified in a first screening is combined with another peptide sequence in order to search for compounds with an improved immunogenic property and/or binding property.

A method of the invention is suitable for the production and/or identification of a compound according to the present invention comprising an immunogenic property and/or binding property of interest. An isolated, synthetic or recombinant compound with a desired immunogenic property and/or binding property obtainable by a method according to the invention is therefore also herewith provided. Said compound preferably comprises a peptide according to the invention coupled to a scaffold. Said scaffold preferably comprises a (hetero) aromatic molecule, more preferably a halomethylarene bis (bromomethyl)benzene, a tris(bromomethyl)benzene or a tetra(bromomethyl)benzene. Most preferably said scaffold comprises at least one meta-dibromoxyleen (m-T2) scaffold, at least one 2,4,6-tris(bromomethyl)mesitylene (T3) scaffold, and/or at least one 1,2,4,5 tetrabromodurene (T4) scaffold.

Compounds according to the invention are suitable for a wide variety of applications. For instance, a compound according to the invention is used for a therapeutic application. A compound according to the invention is for instance suitable for use as an agonist or an antagonist for a receptor-ligand binding pair. In one embodiment a compound with a desired immunogenic property is synthesized and selected. The invention therefore provides an immunogenic compound obtainable by a method according to the invention. Said immunogenic compound for instance consists of an immunogenic peptide obtainable by a method of the invention. Preferably however an immunogenic compound according to the invention comprises an immunogenic peptide bound to a scaffold in order to improve stability and biologic activity of said immunogenic peptide. In one embodiment an immunogenic peptide according to the invention is bound to a (hetero) aromatic molecule, preferably a halomethylarene, via at least two SH-functionalities since such coupling reactions are easily and rapidly performed, even in aqueous solution, without the need of protecting amino acid residues of said immunogenic peptide (except for any additional cysteine residues). Moreover, the resulting immunogenic compound is stable and the peptide comprises a biologically significant structure. In a particularly preferred embodiment an immunogenic peptide according to the invention is coupled to a bis(bromomethyl)benzene, a tris(bromomethyl)benzene or a tetra(bromomethyl)benzene. Most preferably an immunogenic compound is provided comprising an immunogenic peptide coupled to at least one meta-1,3-bis(bromomethyl)benzene (m-T2), ortho-1,2-bis(bromomethyl)benzene (o-T2), para-1,4-bis(bromomethyl)benzene (p-T2), meta-1,3-bis(bromomethyl)pyridine (m-P2), 2,4,6-tris(bromomethyl)mesitylene (T3), meta-1,3-bis(bromomethyl)-5-azidobenzene (m-T3-N3) and/or 1,2,4,5 tetrabromodurene (T4) scaffold.

The invention furthermore provides an immunogenic composition comprising an immunogenic compound obtainable by a method according to the invention. In one embodiment said immunogenic compound is coupled to a suitable carrier, for instance a saline solution and/or a protein carrier such as keyhole limpet haemocyanin (KLH), serum albumin (e.g. BSA or RSA), ovalbumin, Diphteria Toxin (DT), virus-like particles, or any other suitable carrier well known in the art. However, the use of an immunogenic compound according to the present invention coupled to a scaffold often obviates the need to use a carrier. This provides the advantage that an immune response specifically directed against such additional carrier is avoided. One embodiment therefore provides an immunogenic composition comprising an immunogenic compound, which immunogenic compound comprises an immunogenic peptide bound to a scaffold, wherein said immunogenic composition is (essentially) devoid of an additional carrier. In one embodiment an immunogenic composition of the invention comprises a suitable adjuvant such as for instance Freund's Complete Adjuvant (FCA), Incomplete Freund Adjuvant (IFA), an oil in water or double oil in water emulsion or an Aluminum Salt Adjuvant, Montanide ISA, MF59, Aluminium Hydroxide, Titermax, RIBI, Saponins, and/or CoVaccine. An immunogenic composition according to the invention is preferably administered orally or by aerosol or it is preferably injected intramuscularly, subcutaneously or via high pressure needle-free transdermal injection. Dose ranges of (immunogenic) peptides and/or (immunogenic) compounds according to the invention to be used in a therapeutical and/or prophylactic application are designed on the basis of rising dose studies in the clinic in clinical trials for which rigorous protocol requirements exist and which do not need further explanation here. Typically, dosages of between 1 µg to 1 mg per kilogram of body weight are used.

A preferred embodiment provides an immunogenic composition according to the invention comprising at least two different immunogenic peptides according to the invention. Said at least two different immunogenic peptides are preferably capable of eliciting an immune response specifically directed against a proteinaceous molecule of interest. Most preferably said at least two different immunogenic peptides are capable of eliciting a protective immune response specifically directed against a proteinaceous molecule of interest in at least 50%, preferably at least 75%, more preferably at least 80%, most preferably at least 95% of the hosts. A protective immune response against a proteinaceous molecule is defined herein as an immune response that is capable of counteracting at least one property of said proteinaceous molecule.

In one embodiment each of said different peptides of the invention is capable of eliciting a protective immune response against said proteinaceous molecule in at least 50%, preferably at least 75%, more preferably at least 80%, most preferably at least 95% of the hosts. In one embodiment however each single peptide of the invention is by itself essentially not capable of inducing a protective immune response against a proteinaceous molecule of interest, whereas a combination of at least two peptides according to the invention is capable of eliciting a protective immune response against said proteinaceous molecule in at least 50%, preferably at least 75%, more preferably at least 80%, most preferably at least 95% of the hosts. In this case an immunogenic composition comprising at least two immunogenic peptides according to the invention is particularly preferred. In one embodiment an immunogenic composition according to the invention comprises at least three immunogenic peptides according to the invention.

An immunogenic composition of the invention comprising at least two immunogenic compounds according to the invention is particularly suitable for immunisation against a self-antigen. If an immune response against a self-antigen is desired, a self-antigen is preferably used that is modified enough in order to be capable of eliciting an immune response, but which at the same time sufficiently resembles the original self-antigen so that an induced immune response is capable of recognizing self-antigens, Immunisation with such modified self-antigens regularly does not result in an effective immune response in view of the resemblance of the modified self-antigens with unmodified self-antigens. A combination of at least two immunogenic peptides according to the invention however at least in part solves this problem because such combination is better capable of eliciting a protective immune response.

In one embodiment at least two different immunogenic peptides according to the invention are bound to the same scaffold. Immunogenicity is increased, for instance because peptides are fixed in another conformation, different three-dimensional orientations are obtained, and/or as a result of multivalence.

An immunogenic peptide and/or immunogenic compound obtainable by a method according to the present invention is for instance suitable for eliciting an immune response in a non-human animal. Subsequently, it is possible to isolate antibodies and/or T cells capable of specifically binding said immunogenic peptide and/or immunogenic compound. Alternatively, or additionally, an antibody or T cell or functional part, derivative and/or analogue thereof, capable of specifically binding an immunogenic peptide and/or immunogenic compound of the invention, is generated ex vivo, for instance by incubating naive T cells with an antigen presenting cell which has been pulsed with an immunogenic peptide according to the invention. One embodiment therefore provides a method according to the invention, further comprising selecting an immunogenic compound and/or a binding compound of interest, and producing an antibody or T cell or a functional part, derivative and/or analogue thereof capable of specifically binding said immunogenic compound. An isolated or synthetic antibody or T cell, or a functional part, derivative and/or analogue thereof, capable of specifically binding an immunogenic peptide and/or an immunogenic compound obtainable by a method according to the present invention is therefore also herewith provided.

The invention furthermore provides an array comprising a binding compound according to the invention. Such array is particularly suitable for screening a sample for the presence of specific molecules, such as a ligand or a receptor.

The invention furthermore provides an array comprising an immunogenic peptide and/or an immunogenic compound obtainable by a method according to the invention. Such array is particularly suitable for screening a sample for the presence of antibodies and/or T cells capable of specifically binding said immunogenic peptide and/or immunogenic compound according to the invention. For instance, a sample obtained from an individual is screened with an array according to the invention in order to determine whether said individual comprises antibodies and/or T cells capable of specifically binding a proteinaceous molecule of interest. If such antibodies and/or T cells appear to be present in said sample, it indicates that said individual is suffering from, or at risk of suffering from, a disorder involving the presence of said proteinaceous molecule of interest. Said (risk of) disorder is for instance caused by an infection with a pathogen, by the presence of malignant cells, by an autoimmune disease, et cetera.

A further embodiment provides an array comprising an antibody or T cell or functional part, derivative and/or analogue thereof according to the invention. Since such antibody, T cell, functional part, derivative and/or analogue of the invention is capable of specifically binding an immunogenic compound of the invention, said array is for instance suitable for determining the presence of said immunogenic compound in a sample. Furthermore, if said immunogenic compound is a peptidomimetic of an immunogenic proteinaceous molecule of interest, said antibody, T cell, functional part, derivative and/or analogue of the invention is also capable of specifically binding said proteinaceous molecule of interest. In that case said array is also suitable for determining the presence in a sample of said proteinaceous molecule of interest.

DETAILED DESCRIPTION

Investigation of various members of the cystine-knot growth factor family has revealed that peptides derived from the amino acid sequence of the beta-3 hairpin (B3) loop of a cystine-knot growth family member, which peptides have specific characteristics, are particularly suitable for use as a peptidomimetic. Provided is therefore a peptidomimetic of a member of the cystine-knot growth factor family, comprising a polypeptide derived from the amino acid sequence of the beta-3 hairpin (B3) loop of said cystine-knot growth factor family member, wherein two amino acid residues have been replaced by a first and a second cysteine residue that are covalently connected to each other via a scaffold, wherein a) said first scaffold-attached cysteine residue is located p residues C-terminal from the position that corresponds to amino acid CysIV in the wild-type B3-loop, indicated as position CysIV+p, wherein $5 \leq p \leq 12$; b) said second scaffold-attached cysteine residue is located q residues N-terminal from the position that corresponds to amino acid CysV in the wild-type B3-loop, indicated as position CysV−q, wherein $4 \leq q \leq 12$ and wherein (p−q) is −3, −2, −1, 0, 1, 2 or 3; and c) the length of said polypeptide is from amino acid at position CysIV+x to amino acid at position CysV+y, wherein $-5 \leq x \leq 1$ and $1 \leq y \leq 6$ under the provision that x+y=−1, 0, 1 or 2. It was found that looped peptide structures which meet these criteria are suitably used as mimics of Cys-knot family members, as evidenced among other by the ability to induce a specific antibody response in an animal.

Thus, to achieve a looped peptide structure which sufficiently resembles the native conformation of the B3-loop, there are a some general criteria which should be met with respect to the length of the polypeptide and the position of the cysteines residues within the polypeptide via which it is attached (cyclized) to the scaffold. The peptide length may also depend on the nature of the scaffold. These general criteria refer to the conserved residues CysIV and CysV which are positioned at the 'bottom' of the B3 loop in all members of the Cys-knot growth factor family members (see FIG. 1B). It should be noted that, in the native protein, the B3-loop is formed as a result of the complex knot-structure and not by a disulphide bond between CysIV and CysV. In a peptidomimetic of the invention, a scaffold molecule physically constrains a polypeptide to induce a secondary structure which mimics the B3-loop. The scaffold is attached to cysteines within the polypeptide rather than at the ends of the polypeptide and the peptidomimetic can schematically be regarded as A-shaped molecule (see FIG. 1C). A peptidomimetic of the invention is also referred to as a chemically linked peptide scaffold, abbreviated as CLIPS.

Identification of the B3-loop and of residues CysIV and CysV of a given Cys-knot protein family member can be done on the basis of sequence alignment of primary amino acid sequences. Table 13 shows such an alignment of various members of the Cys-knot growth factor family of different mammals. The B3 loop starts at the conserved residue CysIV and ends with the residue N-terminal to CysV, herein also referred to as residue CysV−1. Once the conserved CysIV and CysV residues have been identified, the suitable lengths of the polypeptide and the positions of the cysteines for attaching the polypeptide to the scaffold can be easily determined.

Tables 14A-E list the positions of the six conserved Cys residues (CysI to CysVI) for five different subfamilies of the Cys-knot growth factor family. For example, hCG-alpha contains ten cysteine residues (C-1 to C-10) at positions 7, 12, 28, 31, 32, 59, 60, 82, 84 and 87, respectively. Based on the sequence alignment, C-2 of hCG corresponds to CysI, C-3 to CysII, C-4 is an "extra" cysteine, C-5 corresponds to CysIII, etcetera. Thus, in case of hCG residue Cys60 corresponds to CysIV and residue Cys82 to CysV. As another example, in the GLHB subfamily member FSH-beta Cys51 corresponds to CysIV and Cys 82 to CysV. In a similar fashion, the CysIV and CysV residues can be readily identified for other Cys-knot family members.

The first and second criteria which have to be met define the positions at which the cysteines are to be introduced and via which the polypeptide is attached to the scaffold. The position of the first (i.e. N-terminal cysteine based on the sequence of the B3-loop) and second (i.e. C-terminal) cysteine are considered relevant for the ability of the scaffold to induce a secondary structure which optimally resembles the native protein. The first cysteine residue within said polypeptide is located C-terminal (or 'downstream') from the amino acid position that corresponds to amino acid CysIV in the B3-loop of wild-type protein. This position can be indicated as position CysIV+p. The distance to said position CysIV should not be less than 5 residues and not more than 12 residues. In other words, the position of the first scaffold-attached cysteine corresponds to position CysIV+p, wherein $5 \leq p \leq 12$. The second scaffold-attached cysteine residue is located N-terminal (or "upstream") from the amino acid position that corresponds to amino acid CysV in the B3-loop of wild-type protein. This position can be indicated as position CysV−q. The distance to said position CysV should not be less than 4 residues and not more than 12 residues. In other words, the position of the second scaffold-attached cysteine corresponds to position CysV−q, wherein $4 \leq q \leq 12$. Furthermore, to allow the binding of both cysteines to one scaffold without disturbing the formation of a hairpin, it is important that the cysteines are roughly positioned opposite of each other. For that reason it is required that (p-q) is −3, −2, −1, 0, 1, 2 or 3. For example, the positions of the cysteines via which a polypeptide is attached to a scaffold correspond to amino acid position CysIV+12 and CysV−10, or to CysIV+11 and CysV−10, CysIV+10 and CysV−8, CysIV+9 and CysV−8, CysIV+8 and CysV−6, CysIV+7 and CysV−5, CysIV+7 and CysV−6, CysIV+7 and CysV−4, CysIV+5 and CysV−4 or CysIV+6 and CysV−4. Preferred positions for the cysteines are CysIV+10 and CysV−8, CysIV+7 and CysV−6 or CysIV+8 and CysV−6. Most preferably, a peptidomimetic according to the invention is provided wherein the position of said first and second cysteine correspond to positions CysIV+10 and CysV−8.

Preferably, the first and second cysteine are introduced at the positions of those amino acids which, in the crystal structure, are within a distance of up to 6 Å of each other and whose side chains are oriented in the same direction. Said side chains are preferably not surface-exposed yet participate in the so-called hydrophobic core that keeps the B1- and B3-loops together.

The third criterium which should be met poses a restriction on the length of the peptide. According to this criterium, the length of the polypeptide is from amino acid at position CysIV+x to amino acid at position CysV+y, wherein −5≦x≦1; wherein 1≦y≦6 and under the provision that x+y=−1, 0, 1 or 2. In other words, the first residue of the polypeptide corresponds to residue CysIV+x and the last residue to CysV+y. The provision that x+y=−1, 0, 1 or 2 ensures that following attachment of the polypeptide to the scaffold the 'legs' of the A-shaped molecule (see FIG. 1C) are more or less of comparable length to ensure that the first and last residue of a polypeptide are 'neighbouring' residues in the hairpin structure. For example, the length of the peptide is from CysIV+1 to CysV+1, from CysIV−5 to CysV+6, from CysIV−3 to CysV+4, from CysIV−5 to CysV+4 or from CysIV−2 to CysV+4. Preferably, the length of the polypeptide is from CysIV+1 to CysV+1, from CysIV−2 to CysV+4 or from CysIV−5 to CysV+4. In case of FSHbeta, this means that the polypeptide for example corresponds to the stretch of from amino acid 52 (Cys51+1) to amino acid 83 (Cys82+1) or from amino acid 46 (Cys51−5) to amino acid 86 (Cys82+4).

The term 'derived from' is used to indicate that the polypeptide sequence does not have to be identical to the amino acid sequence found in the B3-loop of naturally occurring Cys-knot proteins. Rather, in most cases the polypeptide will, in addition to the two cysteine residues that have been introduced, differ in at least one amino acid from the sequence of the B3-loop in wild-type proteins of the Cys-knot family. As will be described below, it is preferred that any cysteine residue in the natural sequence other than the two cysteines at the two positions described above is changed into a residue that is not reactive with the scaffold in order to prevent attachment of the polypeptide to the scaffold via a residue other than said first and second cysteines.

Based on the above criteria the invention provides peptidomimetics of any known or yet to be identified member of the Cys-knot growth factor family, for example said member is a member of the glycoprotein hormone-beta (GLHB) family, the platelet-derived growth factor (PDGF) family, the transforming growth factor (TGF) family, the nerve growth factor (NGF) family or the glycoprotein hormone-alpha (GLHA) family.

As said, in a peptidomimetic provided herein a scaffold molecule physically constrains a polypeptide to induce a secondary structure which mimics the B3-loop. The Examples below demonstrate the relevance of the presence of a scaffold in a peptidomimetic as provided herein. When the first and second cysteine are connected via a suitable scaffold, the resulting peptide appears a very effective immunogen. In contrast, when the first and second cysteine within one peptide molecule react with each other to form a disulphide bridge, the resulting looped peptide structure can not be used to induce a specific immune response in a test animal. It is conceivable that the physical constraint provided by the scaffold is important for the formation of a hairpin structure that mimics the secondary structure of the B3-loop in naturally occurring Cys-knot family members.

Various types of scaffolds can be used in a looped peptide structure according to the invention. Suitable scaffolds are those capable of reacting with the first and second cysteine within the polypeptide to form a looped peptide structure. A particular interesting scaffold molecule is a (hetero)aromatic compound, in particular those with at least two benzylic halogen substituents, such as a halomethylarene. These compounds are highly reactive towards thiol groups and rapidly form a covalent bond with peptides comprising a cysteine residue. In one embodiment, a scaffold is a bis(halomethyl)benzene or a tetra(halomethyl)benzene or a derivative thereof. In a preferred embodiment, a scaffold is selected from the group consisting of ortho-, meta- and para-dihalomethylbenzene (also known as dihaloxylene) and 1,2,4,5 tetra halomethylbenzene (also known as 1,2,4,5-tetrahalodurene). More preferably, the scaffold is meta-dibromoxyleen (m-T2) or 1,2,4,5 tetrabromodurene (T4). It should be noted that the term "scaffold" as used herein refers to the unreacted molecule that can be used to prepare a peptidomimetic of the invention (e.g. meta-dibromobenzene) as well as to the scaffold moiety within the resulting peptidomimetic which has reacted with the cysteines and, in case of dibromobenzene, no longer contains the halogen atoms. Methods to construct a peptidomimetic with these scaffolds are discussed in WO2004077062.

Some combinations of scaffolds and peptides were observed that yielded very useful peptidomimetics. In one embodiment, a looped peptide structure comprises a polypeptide with a length from CysIV+1 to CysV+1 that is attached to a meta-dihaloxylene scaffold, preferably meta-dibromoxylene. A preferred peptide length for attachment to a tetrahalodurene scaffold, for example to 1,2,4,5 tetrabromodurene is from CysIV−2 to CysV+4.

Regarding the position of the cysteines through which a looped peptide structure is formed onto a scaffold, particularly useful positions were identified for different subfamilies of the Cys-knot superfamily of growth factors.

Preferred positions of the cysteines to obtain a mimic of a member of the GLBH, the PDGF or the TGF subfamily are CysIV+10 in combination with CysV−8. In case of FSH this corresponds to residues 61 and 74, in case of VEGF to residues 78 and 94 and in case of GDNF to residues 112 and 124. However, for GLBH family members, positions CysIV+12 and CysV−10, CysIV+8 and CysV−6 or CysIV+7 and CysV−5 also give good results. Likewise, positions CysIV+8 and CysV−6 or CysIV+12 and CysV−10 are suitably used for PDGF-family members and positions CysIV+10 and CysV−10 or CysIV+7 and CysV−4 for TGF family members.

One preferred embodiment provides a VEGF peptidomimetic according to the present invention, wherein the position of said first cysteine corresponds to amino acid position CysIV+8 and wherein the position of said second cysteine corresponds to position CysV−6 and wherein said polypeptide is derived from the B3-loop of a VEGF protein.

Preferred positions for the cysteines to obtain a mimic of a member that belongs to the NGF-family are CysIV+7 and CysV−6 (in case of NGF residues 87 and 102). Other useful combinations of cysteine positions for NGF family members include CysIV+5 and CysV−4, CysIV+9 and CysV−8, and CysIV+11 and CysV−10.

Preferred positions for the cysteines to obtain a mimic of a member that belongs to the GLHA-family are CysIV+8 and CysV−6 (in case of CG residues 68 and 76). Other useful combinations of cysteines positions for GLHA-family members include CysIV+6 and CysV−4.

In one embodiment, the invention provides a mimic of a member of the GLBH-, the PDGF- or the TGF-family wherein said mimic is a looped peptide structure consisting of a polypeptide attached via two cysteines to a scaffold, said polypeptide being derived from the amino acid sequence of the beta-3 hairpin loop of said member, wherein the length of said polypeptide is from amino acid position CysIV−5 to CysV+4 and wherein said polypeptide is attached via a first cysteine at position CysIV+10 and a second cysteine at position CysV−8 to a tetrahalomethyl benzene scaffold, preferably tetrabromodurene. In another embodiment, said polypeptide is attached via said cysteines to a bifunctionalized scaffold, for example a dibromobenzene, wherein the length of the peptide is somewhat shorter, for example from amino acid CysIV+1 to CysV+1.

In another embodiment, the invention provides a mimic of a member of the GLBH-, the PDGF- or the TGF-family wherein said mimic is a looped peptide structure consisting of a polypeptide attached via two cysteines to a scaffold, said polypeptide being derived from the amino acid sequence of the beta-3 hairpin loop of said member, wherein the length of said polypeptide is from amino acid position CysIV−5 to CysV+4 and wherein said polypeptide is attached via a first cysteine at position CysIV+10 and a second cysteine at position CysV−8 to a tetrahalomethyl benzene scaffold, preferably tetrabromodurene. In another embodiment, said polypeptide is attached via said cysteines to a bifunctionalized scaffold, for example a dibromobenzene, wherein the length of the peptide is somewhat shorter, for example from amino acid CysIV+1 to CysV+1.

In yet another embodiment, the invention provides a mimic of a member of the GLBH-, the PDGF- or the TGF-family wherein said mimic is a looped peptide structure consisting of a polypeptide attached via two cysteines to a scaffold, said polypeptide being derived from the amino acid sequence of the beta-3 hairpin loop of said member, wherein the length of said polypeptide is from amino acid position CysIV−5 to CysV+4 and wherein said polypeptide is attached via a first cysteine at position CysIV+10 and a second cysteine at position CysV−8 to a tetrahalomethyl benzene scaffold, preferably tetrabromodurene. In another embodiment, said polypeptide is attached via said cysteines to a bifunctionalized scaffold, for example a dibromobenzene, wherein the length of the peptide is somewhat shorter, for example from amino acid CysIV+1 to CysV+1.

In a further aspect, the invention provides a mimic of a member of the NGF-family wherein said mimic is a looped peptide structure consisting of a polypeptide attached via two cysteines to a scaffold, said polypeptide being derived from the amino acid sequence of the beta-3 hairpin loop of said member, wherein the length of said polypeptide is from amino acid position CysIV−5 to CysV+4 and wherein said polypeptide is attached via a first cysteine at position CysIV+10 and a second cysteine at position CysV−8 to a tetrahalomethyl benzene scaffold, preferably tetrabromodurene. In another embodiment, said polypeptide is attached via said cysteines to a bifunctionalized scaffold, for example a dibromobenzene, wherein the length of the peptide is somewhat shorter, for example from amino acid CysIV+1 to CysV+1.

In case the polypeptide length is such that it includes a CysIV and/or CysV residue this means that at least those cysteine(s) should not be present in the polypeptide to avoid a chemical reaction with the scaffold. They can for instance be changed into a residue that is unreactive with the scaffold, for example an alanine residue, to prevent attachment of the polypeptide to the scaffold via a cysteine other than the two cysteines described above. Likewise, any other cysteine residue in the natural sequence is to be changed into a non-cysteine residue. For instance, the invention provides in a particular aspect a peptidomimetic of FSH consisting of a polypeptide derived from the B3-loop of FSH having the sequence TFKELVYETCR VPGAAHHADSLCTYP-VATQAH (SEQ ID NO:31) attached to meta-dibromobenzene (see also Example 3). The polypeptide length corresponds to the stretch from CysIV+1 (Thr52) to CysV+1 (His52). The first C indicated in bold corresponds to position CysIV+10 (Val61 in FSH) and the second C to position CysV−8 (Tyr74 in FSH). Residue Cys66 in FSH is not present in the polypeptide to prevent unwanted interaction with the scaffold. In the polypeptide derived from FSH it is an alanine (the first of the three alanine residues). The same amino acid changes with respect to the sequence of naturally occurring FSH can be found in another FSH peptidomimetic of the invention consisting of the polypeptide KIQKTATFKELVY-ETCRVPGAAHHADSL CTYPVATQAHAGK (SEQ ID NO:32) (corresponding to CysIV−5 to CysV+4) attached to the scaffold 1,2,4,5 tetrabromodurene. However, in this case also Cys84 in FSH (corresponding to CysVI) was changed into an alanine such that the last 5 residues are AHAGK (SEQ ID NO:33) instead of CHCGK (SEQ ID NO:34) as found in FSH.

It is also possible to use a polypeptide comprising a protected amino acid to avoid unwanted reactivity of said amino acid. In one embodiment, a polypeptide comprises in addition to the two cysteines intended for attachment to the scaffold a cysteine residue (e.g. a residue corresponding to CysIV) that is protected with the removable protecting Cys(StBu) group. Following attachment to a scaffold to yield a peptidomimetic of the invention, the protecting group can easily be removed by reductive treatment, for example with 1,4-DDT or ethane dithiol.

In a further aspect, a peptidomimetic is prepared by attaching a polypeptide via two cysteines onto a scaffold wherein said polypeptide is derived from the B3-loop but wherein one or more amino acid residues are replaced by a bioisosteric unit. Bioisosteric replacement can be defined as the replacement of a functional group in a bioactive molecule by another functionality having similar size and physicochemical properties. Bioisosteric replacements are used in the pharma industry to optimize properties of drug candidates (activity, selectivity, transport), to remove unwanted side effects or to design molecules that are easier to synthesize. The bioisosteric replacement may be physicochemically or topologically based.

In still a further aspect, the invention provides a peptidomimetic for hCG consisting of the polypeptide VVANYRD-VRFESCRLPGAPRGVNPVCSYAVALSAQ AAL (SEQ ID NO:35) attached to 1,2,4,5 tetrabromodurene as scaffold to form a looped structure that resembles the B3 loop of hCG. Two cysteines (indicated in bold) were introduced into the sequence at positions 61 (CysIV+10) and 74 (CysV−8). Cysteines at positions 51 (CysIV), 66, 82 (CysV) and 84 (CysVI) in the wild-type protein (see Table 13) were altered into alanine residues. The length of the polypeptide corresponds to the stretch from CysIV−2 (Val49) to CysV+4 (Leu86) in hCG. Also provided is a peptidomimetic comprising a polypeptide with the sequence NYRDVRFESCRLP-GAPRGVNPVCSYAVALSAQ (SEQ ID NO:36) wherein the peptide is attached via the cysteines indicated in bold to the scaffold m-T2.

Also provided is an FSH peptidomimetic comprising a polypeptide with the sequence TFKCLVYETVRVPGAAH-HADSLYTYPVACQAH (SEQ ID NO:37) attached to scaffold m-T2, an FSH peptidomimetic comprising a polypeptide with the sequence TFKELVYETCRVPGDAHHAD-SLCTYPVATQAH (SEQ ID NO:38) attached to scaffold m-T2, an FSH peptidomimetic comprising a polypeptide with the sequence TFKELVYETCRVPGAAHHAD-SLCTYPVATQAH (SEQ ID NO:39) attached to scaffold T3, an FSH peptidomimetic comprising a polypeptide with the sequence TFKELVYETCRVPGDAHHADKLCTYP-VATQAH (SEQ ID NO:40) attached to scaffold m-T2, an FSH peptidomimetic comprising a polypeptide with the sequence TFKELVYETCRVPGDAHKADSLCTYP-VATQAH (SEQ ID NO:41) attached to scaffold m-T2, a VEGF peptidomimetic comprising a polypeptide with the sequence ESNCTMQIMRIKPHQGQHIGEMSCLQH (SEQ ID NO:42) attached to scaffold m-T2, a VEGF peptidomimetic comprising a polypeptide with the sequence EESNCT-MQIMRIKPHQGQHIGEMSCLQHN (SEQ ID NO:43) attached to scaffold m-T2 and a hCG peptidomimetic comprising a polypeptide with the sequence

```
NYRDVRFESCRLPGCPRGVNPVCSYAVALSAQ  (SEQ ID NO: 44)
                              S
                              S
NYRDVRFESCRLPGCPRGVNPVCSYAVALSAQ, (SEQ ID NO: 44)
``` attached to two scaffolds m-T2. As is shown in the examples, these peptidomimetic are particularly suitable for eliciting FSH, hCG and VEGF-specific antisera.

Furthermore, the invention relates to a method for the preparation of a peptidomimetic of the invention. Provided is a method for preparing a looped peptide compound according to the invention, comprising the steps of providing the modified polypeptide and scaffold and contacting said polypeptide and scaffold under conditions that allow for the covalent attachment of said polypeptide to said scaffold, preferably wherein said contacting is performed in solution, more preferably in an aqueous solution. Said modified polypeptide has a sequence derived from the B3-loop of the protein of interest, wherein the length of the polypeptide meets the criteria mentioned above and wherein the polypeptide contains a first and a second cysteine residue at the positions as described in detail above. The polypeptide can be a synthetic peptide. Synthesis can be performed using standard solid phase peptide synthesis or any other way of producing polypeptides. The scaffold preferably comprises two reactive groups capable of forming a covalent bond with said first and second cysteine of the polypeptide, thereby inducing the formation of a looped peptide structure. The coupling reaction is preferably performed using a polypeptide with unprotected amino acid side chains. Preferably, the coupling reaction is performed in solution, more preferably in an aqueous solution. Detailed information regarding the synthesis of a looped peptide structure using halogen-functionalised scaffolds can be found in international patent application WO2004077062.

In another embodiment, a vaccine composition comprising a peptidomimetic according the invention is provided. Animal tests revealed that a composition comprising a peptidomimetic that satisfies the criteria disclosed herein can induce the formation of a specific immune response. Example 3 shows that injection of the TFKELVYETCRVPGAAHHAD-SLCTYPVATQAH (SEQ ID NO:46) polypeptide derived from FSH (residues 52-83) cyclized onto a m-T2 scaffold in rats results in the production of antibodies that are reactive with native FSH. Good results were also obtained with the FSH-derived peptide KIQKTATFKELVYETCRVPGAAH HADSLCTYPVATQAHAGK (SEQ ID NO:32) (residues 49-86) cyclized with T4 scaffold. The relevance of the polypeptide length as disclosed herein is demonstrated by the large reduction in antibody induction when a peptide is used having a sequence from the first cysteine (position CysIV+ 10) to the second cysteine (position CysV−8). When attached to a scaffold, this peptide has a looped structure yet lacks the free ends representing the 'legs' of the characteristic A-shape peptidomimetic of the invention.

The importance of peptide cyclization onto a suitable scaffold is apparent from Example 3 and FIG. 2 which demonstrate that the FSH-derived peptide TFKELV YETCRVP-GAAHHADSLCTYPVATQAH (SEQ ID NO:46) cyclized onto scaffold m-T2 yields a very high antibody titre whereas the serum of rats receiving only linear peptide or peptide that had been cyclized through a disulfide bridge between the two cysteines did not show significant recognition of FSH. In addition, for this particular peptide the meta-T2 scaffold is preferred over ortho- or para-T2 scaffolds.

Example 6 describes the results of a vaccination experiment performed in rats using various peptide compositions as peptide-based vaccine. Six weeks following peptide administration, the serum of the rats was tested for the ability to recognize hCG. For comparison, two commercially available antibodies against hCG were included. Rats that had been injected with a peptidomimetic according to the invention showed a good hCG-specific antibody response whereas rats injected with the linear or SS-cyclized version of the same polypeptide did not show a significant response (FIG. 3).

The invention thus also provides for a vaccine comprising a looped peptide compound according to the invention. The immunogenic peptide compounds may be used alone to induce cellular immunity. They may also be used, e.g. in a vaccine composition, in conjunction with other molecules in order to induce antibody production or a humoral response. The peptidomimetic can be coupled to a carrier, for example a protein carrier such as keyhole limpet haemocyanin (KLH), serum albumin (e.g. BSA or RSA), Ovalbumin or other. Furthermore, an antibody specifically reactive with a looped peptide compound according to the invention is provided.

Also provided is the use of a vaccine comprising a Cys-knot peptidomimetic of the invention.

In one embodiment, a vaccine provided herein is used as birth control vaccine in mammals, preferably in humans. There are currently two major approaches to hormonal male contraception. One relies on testosterone (analogs) either alone or in combination with gonadotropin releasing hormone (GnRH) (analogs or immunizations), the other on immunizations against follicle-stimulating hormone (FSH). Theoretically, the latter method will suppress spermatogenesis whilst not interfering with libido. In a preferred embodiment, the invention provides an anti-FSH vaccine for use in male contraception. Preferably, said anti-FSH vaccine does not include anti-luteinizing hormone (LH) antibodies (LH being responsible for the induction of testosterone which is necessary to maintain libido).

In another embodiment, the invention provides the use of a looped peptide compound as a therapeutic peptide in anti-cancer treatment. For example, a vaccine is provided that can be used in active immunotherapy. For example, said vaccine comprises a looped peptide compound that mimics hCG. The hCG hormone is naturally produced during pregnancy and is believed to stimulate growth and shield the developing embryo from immune attack (i.e., rejection). hCG is a biochemical marker of malignancy associated with all the major types of cancer. The expression of hCG has been shown to correlate with tumor aggressiveness, i.e., the greater the hCG expression, the more aggressive the tumor. In both cases, hCG serves as a growth factor, encouraging rapid cell division. It promotes implantation and tissue invasion, it fosters angiogenesis, the formulation of blood vessels and it facilitates immunosuppression, allowing the foetus or tumor to avoid rejection. Therefore, an immune response directed against hCG stimulates an immune attack against the tumor and neutralizes the hormonal benefits provided by hCG. As a result, an anti-hCG vaccine can be effective in blocking fertility, and therefore can also be effective in treating cancer. Indeed, clinical studies using hCG vaccines in cancer indicate that an immune response to hCG plays a significant role in patient survival.

In a preferred embodiment, a vaccine is provided comprising a peptidomimetic of the invention that is capable of inducing a range of host immune responses (humoral, cellular) against pro-angiogenic factors in tumor-bearing organisms. Of particular interest is a peptidomimetic of the VEGF-A/VEGFR-2 system, due to the critical role of this system in tumor angiogenesis (the formation of new blood vessels to the tumor).

The invention is exemplified by the Examples below. The Examples do not limit the scope of the invention in any way.

Figure 1C:
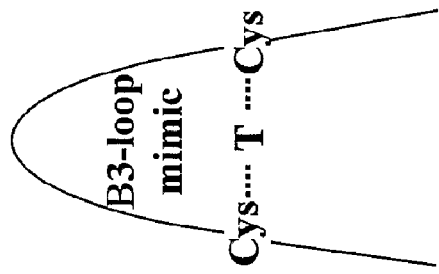
FIG. 1: Schematic representation of the B3-loop of Cys-knot growth factor family members and peptidomimetics thereof. Panel A shows the general loop-structure of the various members of the Cys-knot protein family. Panel B shows the B3-loop including residues CysIV and CysV. Panel C shows the structural design of a peptidomimetic of the invention wherein two cysteines are introduced in the polypeptide such that covalent attachment of the polypeptide via these cysteines to a scaffold (indicated as T) induces the peptide to adopt a conformation which resembles the secondary structure of the B3-loop in the native protein
Figure 1B:
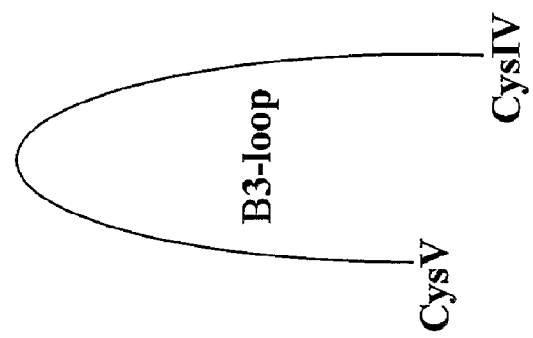
Figure 1A:
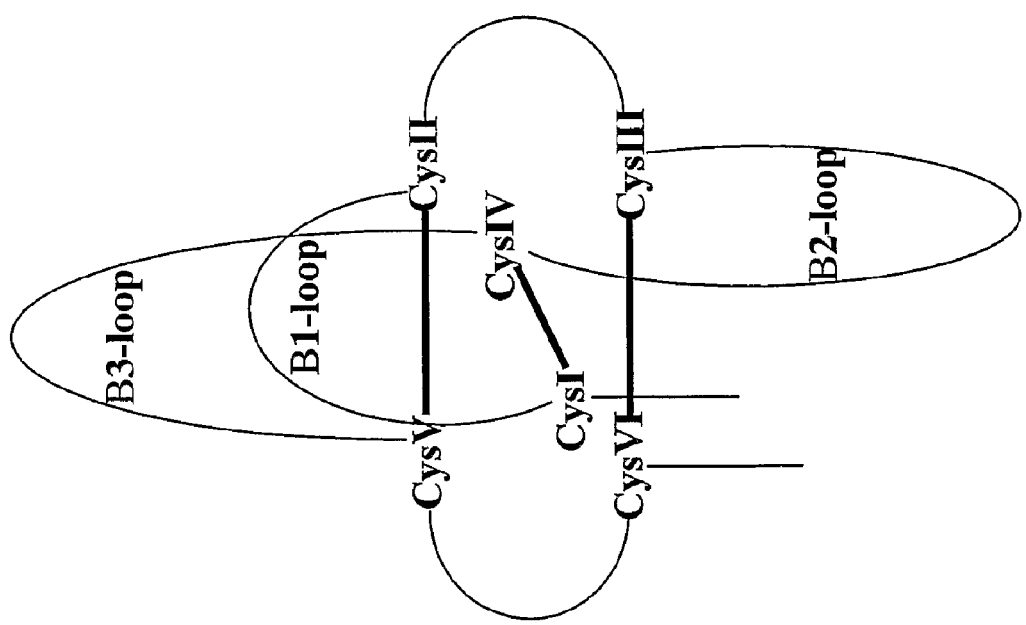

1,2,4,5-tetra(halomethyl)benzene and other regioisomers
1,2,4,5-tetra(halomethyl)pyridine (X═N) and other regioisomers
2,4,5,6-tetra(halomethyl)pyrimidine ($X_1$═$X_2$═N) and other regioisomers
2,3,4,5-tetra(halomethyl)pyrrole (X═NH), -furan (X═O), -thiophene (X═S) and other regioisomers
2,2',6,6'-tetra(halomethyl)biphenylene
2,2'',6,6''-tetra(halomethyl)terphenylene
2,3,5,6-tetra(halomethyl)naphthalene
2,3,7,8-tetra(halomethyl)anthracene
Bis(2,4-bis(halomethyl)phenyl)methane (X═$CH_2$)

Figure 7:
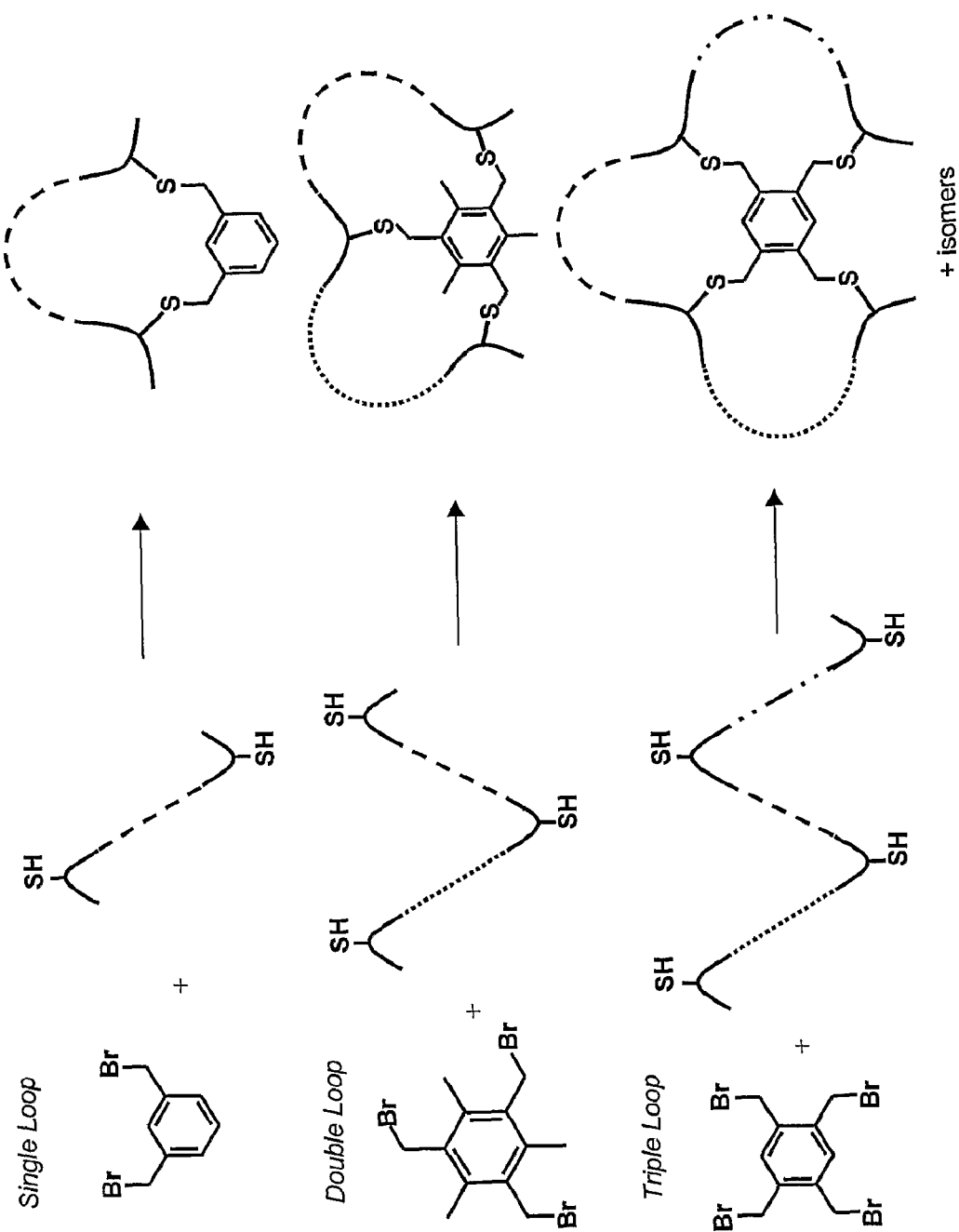

FIG. 7: Schematic representation of the one-step synthesis of single-, double-, and triple-loop peptide constructs.

Figure 8:
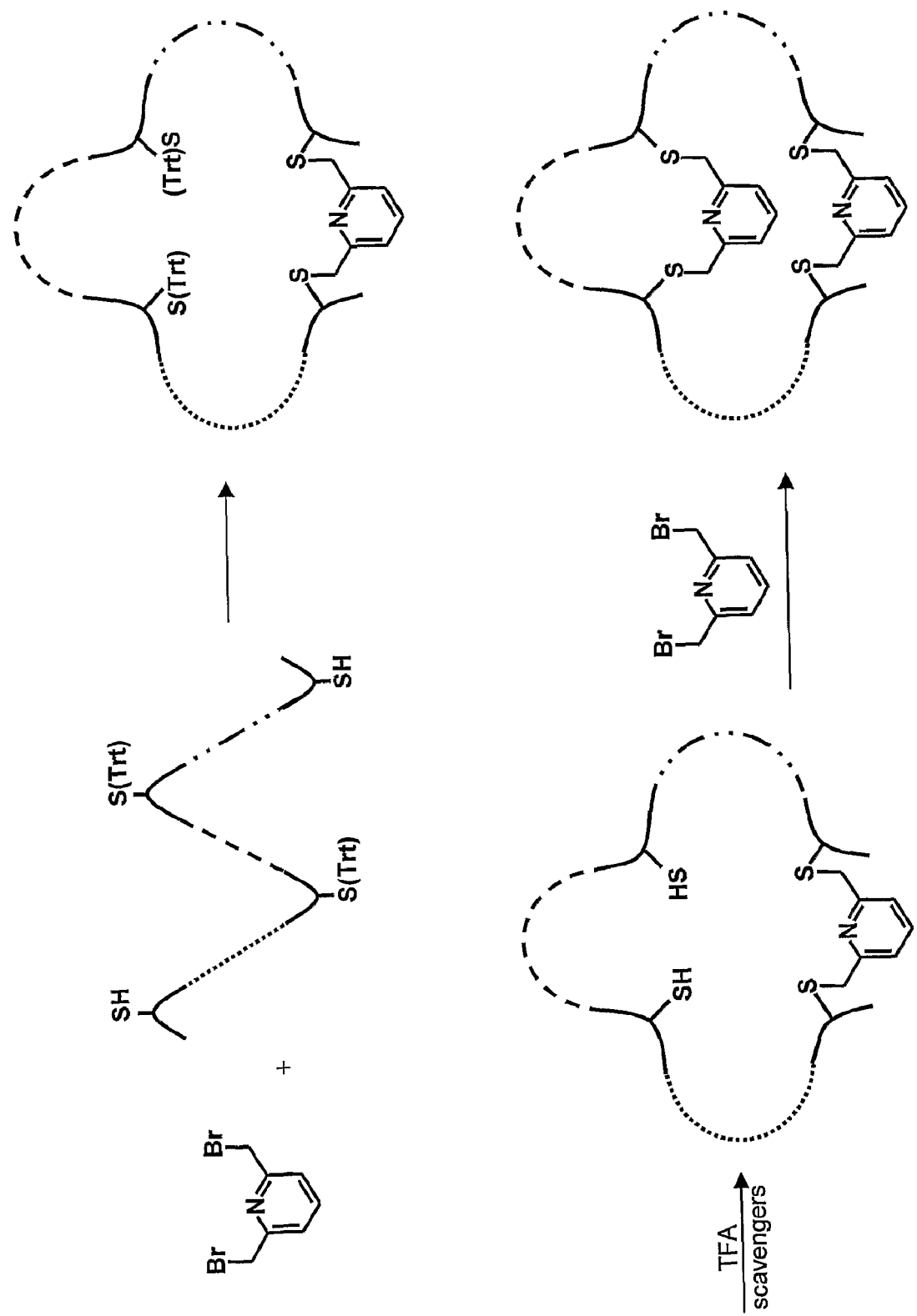

FIG. 8: Schematic representation of the stepwise synthesis of double-looped peptides via initial reaction of a partially Cys(Trt)-protected peptide with mP2, followed by removal of the remaining Trt-protecting groups and subsequent reaction with a second equivalent of mP2.

EXAMPLES

Example 1

Design and Preparation of Immunogenic Compounds Based on CCR5

Materials & Methods

Synthesis of Peptides on Microarrays and Reaction with m-P2 or T3-Scaffold

Grafting of the polypropylene support with polyacrylic acid was performed by irradiating the support in a 6% acrylic acid solution containing CUS04 using gamma radiation at a dose of 12 kGy. The grafted solid support containing carboxylic acid groups was subsequently reacted with t-butyloxycarbonyl-hexamethylenediamine (Boc-HMDA) using dicyclohexylcarbodiimide (DCC) with N-hydroxybenzotriazole (HOBt) and subsequent cleavage of the Boc-groups using trifluoroacetic acid (TFA). The peptides were synthesized using standard Fmoc-chemistry and, after acylation, deprotected by reaction with TFA (15 ml/g resin) containing 13.3% (w) phenol, 5% (v) thioanisole, 2.5% (v) 1,2-ethanedithiol, and 5% (v) milliQ-$H_2O$ for 2-4 hrs at RT. After washing 3× with $H_2O$, the peptide microarrays were treated with excess of a 1.0 mM solution of either mP2 or T3 in 20 mM amm. bicarbonate (pH 7.8)/acetonitril (1:1 v/v) for 30-60 min. at room temperature, followed by 3× washing with 50% ACN/$H_2O$. Then, the microarrays were washed with excess of millipore $H_2O$ and sonicated in disrupt-buffer (1% SDS/0.1% β-mercaptoethanol (BME) in phosphate buffered saline (PBS), pH 7.2) at 70° C. for 30 min. followed by sonication in millipore $H_2O$ for another 45 min.

Synthese Van Scaffolds:

The scaffolds are commercially available by Aldrich.

Screening of Micro-Arrays with Antibodies

Microarrays were pretreated with PBS for 30 min. followed by precoating with incubation buffer (PBS containing 5% ovalbumin, 5% horse serum and 1% Tween-80) for 1 hour. Then, the microarrays were incubated with mAb (typically 1/1000, diluted in incubation buffer) overnight at 4° C. After washing (3×10 min.) with PBS/Tween-80 (0.05%), the peptides were incubated with peroxidase labeled rabbit anti-mouse antibody for 1 hr at 25° C. (rampo, 1/1000; Dako, Glostrup, Denmark) and subsequently, after washing again (3×10 min.) with PBS/Tween-80 (0.05%), incubated with the peroxidase substrate 2,2'-azino-di-3-ethylbenzthiazoline sulfonate (ABTS; 50 mg in 100 ml 0.1M citric acid-sodium phosphate (McIlvaine) buffer (pH 4.0) containing 20 ul 30% $H_2O_2$). After 1 h the absorbance (at 405 nm) was measured using a CCD-camera (XC-77RR, Sony, Japan). Bound mAb was removed by sonication in disrupt-buffer as described above. The micro-arrays were re-used for screening approximately 10-15 times.

CCR5

CCR5 is a cytokine co-receptor that is used by HIV for cellular entry. Antibodies specifically directed against CCR5 would therefore be suitable for counteracting cellular entry by HIV. However, immunization with whole CCR5 is problematic since CCR5 is a transmembrane protein. In order to be capable of eliciting CCR5-specific antibodies, immunogenic compounds based on CCR5 are therefore desired.

In order to design suitable test compounds, 4 CCR5 sequences were taken into account: one N-terminus domain (Nt) and three extracellular loop domains extended with about 1-6 adjacent amino acid residues of the transmembrane domains (N-terminally as well as C-terminally). These extracellular loop domains are called e1, e2 and e3. The primary sequences of the considered domains are as follows (starting N-terminally):

```
Nt: MDYQVSSPIYDINYYTSEPCQKINVKQIA   (SEQ ID NO: 47)
e1: PFWAHYAAAQWDFGNTMCQLLTGL        (SEQ ID NO: 48)
e2: IFTRSQKEGLHYTCSSHFPYSQYQFWKNFQ (SEQ ID NO: 49)
e3: NTFQEFFGLNNCSSSNRLDQAM         (SEQ ID NO: 50)
```

The cysteine residues form native C-bridges in natural CCR5.

The extracellular domain at the N-terminal side of the Cys residue in e2 is called ECL2A whereas the extracellular domain at the C-terminal side of the Cys residue in e2 is called ECL2B. Likewise, the extracellular domain at the N-terminal side of the Cys residue in e3 is called ECL3A whereas the extracellular domain at the C-terminal side of the Cys residue in e3 is called ECL3B.

```
ECL2A: TRSQKEGLHYT       (SEQ ID NO: 51)
ECL2B: SSHFPYSQYQFWK     (SEQ ID NO: 52)
ECL3A: QEFFGLNN          (SEQ ID NO: 53)
ECL3B: SSSNRLDQ          (SEQ ID NO: 54)
```

Subsequently, various amino acid residues are selected within the primary sequence of Nt, e1, e2 and e3. Flanking sequences of these selected amino acids are selected and peptides are produced that comprise these flanking sequences. Cysteine residues are used as groups capable of reacting with a scaffold.

The following peptides were synthesized:

| | Peptides synthesized and screened | |
|---|---|---|
| 1 all 18 overlapping linear 21-mers covering | MDYQVSSPIYDINYYTSEPCQKINVKQIA | (SEQ ID NO: 55) |
| 2 all 9 overlapping linear 18-mers covering | MDYQVSSPIYDINYYTSEPCQKINVK | (SEQ ID NO: 56) |
| 3 all 8 overlapping linear 19-mers covering Nt | MDYQVSSPIYDINYYTSEPCQKINVK | (SEQ ID NO: 56) |
| 4 all 7 overlapping linear 20-mers covering Nt | MDYQVSSPIYDINYYTSEPCQKINVK | (SEQ ID NO: 56) |
| 5 all 6 overlapping linear 21-mers covering Nt | MDYQVSSPIYDINYYTSEPCQKINVK | (SEQ ID NO: 56) |
| 6 all 7 overlapping linear 18-mers covering e1 | PFWAHYAAAQWDFGNTMCQLLTGL | (SEQ ID NO: 57) |
| 7 all 6 overlapping linear 19-mers covering e1 | PFWAHYAAAQWDFGNTMCQLLTGL | (SEQ ID NO: 57) |
| 8 all 5 overlapping linear 20-mers covering e1 | PFWAHYAAAQWDFGNTMCQLLTGL | (SEQ ID NO: 57) |
| 9 all 4 overlapping linear 21-mers covering e1 | PFWAHYAAAQWDFGNTMCQLLTGL | (SEQ ID NO: 57) |
| 10 all 13 overlapping linear 18-mers covering e2 | IFTRSQKEGLHYTCSSHFPYSQYQFWKNFQ | (SEQ ID NO: 58) |
| 11 all 12 overlapping linear 19-mers covering e2 | IFTRSQKEGLHYTCSSHFPYSQYQFWKNFQ | (SEQ ID NO: 58) |
| 12 all 11 overlapping linear 20-mers covering e2 | IFTRSQKEGLHYTCSSHFPYSQYQFWKNFQ | (SEQ ID NO: 58) |
| 13 all 10 overlapping linear 21-mers covering e2 | IFTRSQKEGLHYTCSSHFPYSQYQFWKNFQ | (SEQ ID NO: 58) |
| 14 all 5 overlapping linear 18-mers covering e3 | NTFQEFFGLNNCSSSNRLDQAM | (SEQ ID NO: 59) |
| 15 all 4 overlapping linear 19-mers covering e3 | NTFQEFFGLNNCSSSNRLDQAM | (SEQ ID NO: 59) |
| 16 all 3 overlapping linear 20-mers covering e3 | NTFQEFFGLNNCSSSNRLDQAM | (SEQ ID NO: 59) |
| 17 all 2 overlapping linear 21-mers covering e3 | NTFQEFFGLNNCSSSNRLDQAM | (SEQ ID NO: 59) |
| 18 all 23 overlapping T2 looped 6-mers covering | MDYQVSSPIYDINYYTSEPCQKINVK | (SEQ ID NO: 60) |
| 19 all 22 overlapping T2 looped 7-mers covering | MDYQVSSPIYDINYYTSEPCQKINVK | (SEQ ID NO: 60) |
| 20 all 21 overlapping T2 looped 8-mers covering | MDYQVSSPIYDINYYTSEPCQKINVK | (SEQ ID NO: 60) |
| 21 all 20 overlapping T2 looped 9-mers covering | MDYQVSSPIYDINYYTSEPCQKINVK | (SEQ ID NO: 60) |
| 22 all 19 overlapping T2 looped 10-mers covering | MDYQVSSPIYDINYYTSEPCQKINVK | (SEQ ID NO: 60) |
| 23 all 18 overlapping T2 looped 11-mers covering | MDYQVSSPIYDINYYTSEPCQKINVK | (SEQ ID NO: 60) |
| 24 all 17 overlapping T2 looped 12-mers covering | MDYQVSSPIYDINYYTSEPCQKINVK | (SEQ ID NO: 60) |
| 25 all 16 overlapping T2 looped 13-mers covering | MDYQVSSPIYDINYYTSEPCQKINVK | (SEQ ID NO: 60) |

-continued

| | Peptides synthesized and screened | | |
|---|---|---|---|
| 26 all 15 overlapping T2 looped 14-mers covering | MDYQVSSPIYDINYTSEPCQKINVK | (SEQ ID NO: 60) |
| 27 all 14 overlapping T2 looped 15-mers covering | MDYQVSSPIYDINYTSEPCQKINVK | (SEQ ID NO: 60) |
| 28 all 13 overlapping T2 looped 16-mers covering | MDYQVSSPIYDINYTSEPCQKINVK | (SEQ ID NO: 60) |
| 29 all 12 overlapping T2 looped 17-mers covering | MDYQVSSPIYDINYTSEPCQKLNVK | (SEQ ID NO: 60) |
| 30 all 11 overlapping T2 looped 18-mets covering | MDYQVSSPIYDINYTSEPCQKINVK | (SEQ ID NO: 60) |
| 31 all 10 overlapping T2 looped 19-mers covering | MDYQVSSPIYDINYTSEPCQKINVK | (SEQ ID NO: 60) |
| 32 all 9 overlapping T2 looped 20-mers covering | MDYQVSSPIYDINYTSEPCQKINVK | (SEQ ID NO: 60) |
| 33 all 8 overlapping T2 looped 21-mers covering | MDYQVSSPIYDINYTSEPCQKINVK | (SEQ ID NO: 60) |
| 34 all 8 overlapping T2 looped 6-mers covering e1 | AAAQWDFGNTM | (SEQ ID NO: 61) |
| 35 all 7 overlapping T2 looped 7-mers covering e1 | AAAQWDFGNTM | (SEQ ID NO: 61) |
| 36 all 6 overlapping T2 looped 8-mers covering e1 | AAAQWDFGNTM | (SEQ ID NO: 61) |
| 37 all 5 overlapping T2 looped 9-mers covering e1 | AAAQWDFGNTM | (SEQ ID NO: 61) |
| 38 all 4 overlapping T2 looped 10-mers covering e1 | AAAQWDFGNTM | (SEQ ID NO: 61) |
| 39 all 3 overlapping T2 looped 11-mers covering e1 | AAAQWDFGNTM | (SEQ ID NO: 61) |
| 40 all 2 overlapping T2 looped 12-mers covering e1 | AAAQWDFGNTM | (SEQ ID NO: 61) |
| 41 all 1 overlapping T2 looped 13-mers covering e1 | AAAQWDFGNTM | (SEQ ID NO: 61) |
| 42 all 7 overlapping T2 looped 6-mers covering e2a | RSQKEGLHYT | (SEQ ID NO: 62) |
| 43 all 6 overlapping T2 looped 7-mers covering e2a | RSQKEGLHYT | (SEQ ID NO: 62) |
| 44 all 5 overlapping T2 looped 8-mers covering e2a | RSQKEGLHYT | (SEQ ID NO: 62) |
| 45 all 4 overlapping T2 looped 9-mers covering e2a | RSQKEGLHYT | (SEQ ID NO: 62) |
| 46 all 3 overlapping T2 looped 10-mers covering e2a | RSQKEGLHYT | (SEQ ID NO: 62) |
| 47 all 2 overlapping T2 looped 11-mers covering e2a | RSQKEGLHYT | (SEQ ID NO: 62) |
| 48 all 1 overlapping T2 looped 12-mers covering e2a | RSQKEGLHYT | (SEQ ID NO: 62) |
| 49 all 10 overlapping T2 looped 6-mers covering e2b | SSHPYSQYQFWK | (SEQ ID NO: 63) |
| 50 all 9 overlapping T2 looped 7-mers covering e2b | SSHPYSQYQFWK | (SEQ ID NO: 63) |

-continued

| Peptides synthesized and screened | | |
|---|---|---|
| 51 all 8 overlapping T2 looped 8-mers covering e2b | SSHFPYSQYQFWK | (SEQ ID NO: 63) |
| 52 all 7 overlapping T2 looped 9-mers covering e2b | SSHFPYSQYQFWK | (SEQ ID NO: 63) |
| 53 all 6 overlapping T2 looped 10-mers covering e2b | SSHEPYSQYQFWK | (SEQ ID NO: 63) |
| 54 all 5 overlapping T2 looped 11-mers covering e2b | SSHFPYSQYQFWK | (SEQ ID NO: 63) |
| 55 all 4 overlapping T2 looped 12-mers covering e2b | SSHFPYSQYQFWK | (SEQ ID NO: 63) |
| 56 all 3 overlapping T2 looped 13-mers covering e2b | SSHFPYSQYQFWK | (SEQ ID NO: 63) |
| 57 all 2 overlapping T2 looped 14-mers covering e2b | SSHFPYSQYQFWK | (SEQ ID NO: 63) |
| 58 all 1 overlapping T2 looped 15-mers covering e2b | SSHFPYSQYQFWK | (SEQ ID NO: 63) |
| 59 all 13 overlapping T2 looped 6-mers covering e3 | QEFFGLNNCSSSNRLD | (SEQ ID NO: 64) |
| 60 all 12 overlapping T2 looped 7-mers covering e3 | QEFFGLNNCSSSNRLD | (SEQ ID NO: 64) |
| 61 all 11 overlapping T2 looped 8-mers covering e3 | QEFFGLNNCSSSNRLD | (SEQ ID NO: 64) |
| 62 all 10 overlapping T2 looped 9-mers covering e3 | QEFFGLNNCSSSNRLD | (SEQ ID NO: 64) |
| 63 all 9 overlapping T2 looped 10-mers covering e3 | QEFFGLNNCSSSNRLD | (SEQ ID NO: 64) |
| 64 all 8 overlapping T2 looped 11-mers covering e3 | QEFFGLNNCSSSNRLD | (SEQ ID NO: 64) |
| 65 all 7 overlapping T2 looped 12-mers covering e3 | QEFFGLNNCSSSNRLD | (SEQ ID NO: 64) |
| 66 all 6 overlapping T2 looped 13-mers covering e3 | QEFFGLNNCSSSNRLD | (SEQ ID NO: 64) |
| 67 all 5 overlapping T2 looped 14-mers covering e3 | QEFFGLNNCSSSNRLD | (SEQ ID NO: 64) |
| 68 all 4 overlapping T2 looped 15-mers covering e3 | QEFFGLNNCSSSNRLD | (SEQ ID NO: 64) |
| 69 all 3 overlapping T2 looped 16-mers covering e3 | QEFFGLNNCSSSNRLD | (SEQ ID NO: 64) |
| 70 all 2 overlapping T2 looped 17-mers covering e3 | QEFFGLNNCSSSNRLD | (SEQ ID NO: 64) |
| 71 all 1 overlapping T2 looped 18-mers covering e3 | QEFFGLNNCSSSNRLD | (SEQ ID NO: 64) |
| 72 all 11 overlapping T2 looped 18-mers covering Nt | MDYQVSSPIYDINYYTSEPAQKINVK | (SEQ ID NO: 65) |
| 73 all 10 overlapping T2 looped 19-mers covering Nt | MDYQVSSPIYDINYYTSEPAQKINVK | (SEQ ID NO: 65) |
| 74 all 9 overlapping T2 looped 20-mers covering Nt | MDYQVSSPIYDINYYTSEPAQKINVK | (SEQ ID NO: 65) |
| 75 all 8 overlapping T2 looped 21-mers covering Nt | MDYQVSSPIYDINYYTSEPAQKINVK | (SEQ ID NO: 65) |

-continued

| | Peptides synthesized and screened | | |
|---|---|---|---|
| 76all 13 overlapping T2 looped 18-mers covering Nt + e3 | MDYQVSSPIYDINYTSEPA-G-SSSNRLD | (SEQ ID NO: 66) |
| 77all 12 overlapping T2 looped 19-mers covering Nt + e3 | MDYQVSSPIYDINYTSEPA-G-SSSNRLD | (SEQ ID NO: 66) |
| 78all 11 overlapping T2 looped 20-mers covering Nt + e3 | MDYQVSSPIYDINYTSEPA-G-SSSNRLD | (SEQ ID NO: 66) |
| 79all 10 overlapping T2 looped 21-mers covering Nt + e3 | MDYQVSSPIYDINYTSEPA-G-SSSNRLD | (SEQ ID NO: 66) |
| 80all 4 overlapping T2 looped 18-mers covering Nt + e1 | QKTNVK-GG-AAAQMDFGNTM | (SEQ ID NO: 67) |
| 81all 3 overlapping T2 looped 19-mers covering Nt + e1 | QKINVK-GG-AAAQMDFGNTM | (SEQ ID NO: 67) |
| 82all 2 overlapping T2 looped 20-mers covering Nt + e1 | QKINVK-GG-AAAQMDFGNTM | (SEQ ID NO: 67) |
| 83all 1 overlapping T2 looped 21-mers covering Nt + e1 | QKINVK-GG-AAAQMDFGNTM | (SEQ ID NO: 67) |
| 84all 2 overlapping T2 looped 18-mers covering Nt + ECL3A | QKINVK-GG-QEFFGLNNC | (SEQ ID NO: 68) |
| 85all 1 overlapping T2 looped 19-mers covering Nt + ECL3A | QKLNVK-GG-QEFFGLNNC | (SEQ ID NO: 68) |
| 86all 10 overlapping T2 looped 18-mers covering e1 + e2a | AAAQMDFGNTM-GGG-RSQKEGLHYTC | (SEQ ID NO: 69) |
| 87all 9 overlapping T2 looped 19-mers covering e1 + e2a | AAAQMDFGNTM-GGG-RSQKEGLHYTC | (SEQ ID NO: 69) |
| 88all 8 overlapping T2 looped 20-mers covering e1 + e2a | AAAQMDFGNTM-GGG-RSQKEGLHYTC | (SEQ ID NO: 69) |
| 89all 7 overlapping T2 looped 21-mers covering e1 + e2a | AAAQMDFGNTM-GGG-RSQKEGLHYTC | (SEQ ID NO: 69) |
| 90all 12 overlapping T2 looped 18-mers covering e1 + e2b | AAAQMDFGNTM-GGG-SSHPPYSQYQFWK | (SEQ ID NO: 70) |
| 91all 11 overlapping T2 looped 19-mers covering e1 + e2b | AAAQMDFGNTM-GGG-SSHPPYSQYQFWK | (SEQ ID NO: 70) |
| 92all 10 overlapping T2 looped 20-mers covering e1 + e2b | AAAQMDFGNTM-GGG-SSHPPYSQYQFWK | (SEQ ID NO: 70) |
| 93all 9 overlapping T2 looped 21-mers covering e1 + e2b | AAAQMDFGNTM-GGG-SSHPPYSQYQFWK | (SEQ ID NO: 70) |
| 94all 9 overlapping T2 looped 18-mers covering e1 + e3 | AAAQMDFGNTM-GGGG-QEFFGLNNC | (SEQ ID NO: 71) |
| 95all 8 overlapping T2 looped 19-mers covering e1 + e3 | AAAQMDFGNTM-GGGG-QEFFGLNNC | (SEQ ID NO: 71) |
| 96all 7 overlapping T2 looped 20-mers covering e1 + e3 | AAAQMDFGNTM-GGGG-QEFFGLNNC | (SEQ ID NO: 71) |
| 97all 6 overlapping T2 looped 21-mers covering e1 + e3 | AAAQMDFGNTM-GGGG-QEFFGLNNC | (SEQ ID NO: 71) |
| 98all 9 overlapping T2 looped 18-mers covering e2a + e2b | RSQKEGLHYT-A-SSHPPYSQYQFWK | (SEQ ID NO: 72) |
| 99all 8 overlapping T2 looped 19-mers covering e2a + e2b | RSQKEGLHYT-A-SSLIFPYSQYQFWK | (SEQ ID NO: 72) |
| 100all 7 overlapping T2 looped 20-mers covering e2a + e2b | RSQKEGLHYT-A-SSHPPYSQYQFWK | (SEQ ID NO: 72) |

-continued

| | Peptides synthesized and screened | | |
|---|---|---|---|
| 101a11 6 overlapping T2 looped 21-mers covering e2a + e2b | RSQKEGLHYT-A-SSHFPYSQYQFWK | (SEQ ID NO: 72) | |
| 102a11 14 overlapping T2 looped 18-mers covering e2b + e1 | CSSHFPYSQYQFWK-GGG-AAAQWDFGNTMC | (SEQ ID NO: 73) | |
| 103a11 13 overlapping T2 looped 19-mers covering e2b + e1 | CSSHFPYSQYQFWK-GGG-AAAQWDFGNTMC | (SEQ ID NO: 73) | |
| 104a11 12 overlapping T2 looped 20-mers covering e2b + e1 | CSSHFPYSQYQFWK-GGG-AAAQWDFGNTMC | (SEQ ID NO: 73) | |
| 105a11 11 overlapping T2 looped 21-mers covering e2b + e1 | CSSHFPYSQYQFWK-GGG-AAAQWDFGNTMC | (SEQ ID NO: 73) | |
| 106a11 17 overlappingT2 looped 18-mers covering e2b + e3 | CSSHFPYSQYQFWK-GG-QEFFGLNNASSSNRLD | (SEQ ID NO: 74) | |
| 107a11 16 overlapping T2 looped 19-mers covering e2b + e3 | CSSHFPYSQYQFWK-GG-QEFFGLNNASSSNRLD | (SEQ ID NO: 74) | |
| 108a11 15 overlapping T2 looped 20-mers covering e2b + e3 | CSSHFPYSQYQFWK-GG-QEFFGLNNASSSNRLD | (SEQ ID NO: 74) | |
| 109a11 14 overlapping T2 looped 21-mers covering e2b + e3 | CSSHFPYSQYQFWK-GG-QEFFGLNNASSSNRLD | (SEQ ID NO: 74) | |
| 110a11 15 overlapping T2 looped 18-mers covering e3 + e1 | QEFFGLNNASSSNRLD-GGG-AAAQWDFGNTM | (SEQ ID NO: 75) | |
| 111a11 14 overlapping T2 looped 19-mers covering e3 + e1 | QEFFGLNNASSSNRLD-GGG-AAAQWDFGNTM | (SEQ ID NO: 75) | |
| 112a11 13 overlapping T2 looped 20-mers covering e3 + e1 | QEFFGLNNASSSNRLD-GGG-AAAQWDFGNTM | (SEQ ID NO: 75) | |
| 113a11 12 overlapping T2 looped 21-mers covering e3 + e1 | QEFFGLNNASSSNRLD-GGG-AAAQWDFGNTM | (SEQ ID NO: 75) | |
| 114a11 9 overlapping T2 looped 21-mers covering Nt + e3b | MDYQVSSPIYDINYYTSEC-G-CSSSNRLD | (SEQ ID NO: 76) | |
| 115a11 36 overlapping T2 looped 21-mers covering Nt + e3b | DYQVSSPIYDINYYTSEPC-G-CSSSNRLDQAMQ | (SEQ ID NO: 77) | |
| 116T2 looped 19 to 21-mers covering Nt + e1 | QKINVK-GG-CAAAQWDFGNTM | (SEQ ID NO: 78) | |
| 117 P2P2 looped 18 to 21-mers covering e1 (SEQ ID NO:80) right C------1-G-1------C | AAAQWDFGNTM | (SEQ ID NO: 79)left and e2a | SQKEGLHYT |
| 118 P2P2 looped 21-mers covering e1 (SEQ ID NO:82) right C------1-G-1------C | AQWDFGN | (SEQ ID NO: 81)left and e2a | SSHFPYSQYQFWKN |
| 119 P2P2 looped 21-mers covering e1 (SEQ ID NO:84) right C------1-G-1------C | HYAAAQWDFGNTM | (SEQ ID NO: 83)left and e2a | SSHFPYSQYQFWKN |
| 120 P2P2 looped 21-mers covering Nt (SEQ ID NO:86) right C------1-G-1------C | SEPCQKLNVK | (SEQ ID NO: 85)left and e3 | QEFFGLNNCSSSN |

-continued

| | Peptides synthesized and screened | |
|---|---|---|
| 121 T3 looped 16 to 20-mers peptides covering e1 (SEQ ID NO:88) right | AAAQWDFGNTM | (SEQ ID NO: 87) left and e2a RSQKEGLHYT |
| 122 T3 looped 20-mers peptides covering e1 (SEQ ID NO:90) right | AQWDFGNTM | (SEQ ID NO: 89) left and e2b SSHFPYSQYQFWKNF |
| 123 T3 looped 20-mers peptides covering e2b (SEQ ID NO:87) right | SSHFPYSQYQFWKNF | (SEQ ID NO: 90) left and e1 AAAQWDFGNTM |
| 124 T3 looped 20-mers peptides covering e2b (SEQ ID NO:91) right | SSHFPYSQYQFWKNF | (SEQ ID NO: 90) left and e3 QEFFGLNNASSSNRLDQ |
| 125 T3 looped 20-mers peptides covering e1 (SEQ ID NO:91) right, GCG in middle | YAAAQWDFGNTM | (SEQ ID NO: 92) left and e3 QEFFGLNNASSSNRLDQ |
| 126 T3 looped 20-mers peptides covering e3 (SEQ ID NO:92) right, GCG in middle | QEFFGLNNASSSNRLDQ | (SEQ ID NO: 91) left and e1 YAAAQWDFGNTM |
| 127 T3 looped 21-mers peptides covering e2 | SLPGILFTRSQKEGLHYTCSSHFPYSQYQFWKNEQTL | (SEQ ID NO: 93) |
| 128 T3 looped 21-mers peptides covering Nt | DYQVSPIYDINYYTSEPCQKINVKQIAARLLPPLYS | (SEQ ID NO: 94) |

In the first series of peptides (first row of the above Table), the C-terminal amino acids K, I, N, V, K, Q, I, and A of the Nt sequence were selected. Subsequently, N-terminal flanking sequences with a length of 21 amino acid residues were selected. Hence, MDYQVSSPIYDINYYTSEPCQ (SEQ ID NO:95) was a flanking sequence of K, DYQVSSPIY-DINYYTSEPCQK (SEQ ID NO:96) was a flanking sequence of I, YQVSSPIYDINYYTSEPCQKI (SEQ ID NO:97) was a flanking sequence of N, et cetera.

Subsequently, peptides were produced containing one of these flanking sequences.

Likewise, in the second series of peptides (second row of the above Table), the C-terminal amino acids P, C, Q, K, I, N, V and K of the Nt sequence were selected. Subsequently, N-terminal flanking sequences with a length of 18 amino acid residues were selected. Hence, MDYQVSSPIYDINYYTSE (SEQ ID NO:98) was a flanking sequence of P, DYQVSSPIY-DINYYTSEP (SEQ ID NO:99) was a flanking sequence of C, YQVSSPIYDINYYTSEPC (SEQ ID NO:100) was a flanking sequence of Q, et cetera.

Subsequently, peptides were produced containing one of these flanking sequences.

The peptides of the first 17 series of peptides (rows 1-17 of the above mentioned Table) were not bound to a scaffold and appeared to be less suitable as compared to scaffold-bound peptides.

In the 18$^{th}$ series of peptides all amino acids, except for the first 6 N-terminal amino acids, were selected and N-terminal flanking sequences with a length of 6 amino acids were selected. Subsequently, peptides were produced containing one of these flanking sequences and two cysteine residues. The peptides were coupled to a P2 scaffold via their two cysteine residues. Of note, if a flanking sequence comprised a cysteine residue that was not intended for coupling, the cysteine was replaced by alanine. The peptides of series 19-75 were produced similarly.

In series 76-116 flanking sequences derived from two different domains of CCR5 were combined. For instance, in series 76-79, flanking sequences derived from Nt were combined with flanking sequences derived from e3. Likewise, in series 80-83, flanking sequences derived from Nt were combined with flanking sequences derived from e1, et cetera. The resulting peptides were coupled to P2 via two cysteine residues.

In series 117-120, two P2 scaffolds were used. Peptides were produced comprising two flanking sequences, wherein a flanking sequence derived from e1 was combined with a flanking sequence derived from E2A (rows 117-119 of the above Table) and a flanking sequence derived from Nt was combined with a flanking sequence derived from e3 (row 120 of the above Table). Cysteine residues were present at the start and the end of each flanking sequence (hence, there were four cysteines altogether). If a flanking sequence comprised a cysteine residue that was not intended for coupling, the cysteine was replaced by alanine. Subsequently, the peptides were couples to two P2 scaffolds, using the above mentioned four cysteine residues. (The cysteine residues are depicted in the above Table as C and 1) The two cysteines depicted as C were both coupled to one T2 scaffold and the two cysteine residues depicted as 1 were both coupled to another scaffold.

In series 121-128, a T3 scaffold was used. Peptides were produced comprising two flanking sequences derived from different CCR5 domains. Three cysteine residues were incorporated into the peptides in order to couple them to a T3 scaffold.

Screening Assay

The produced peptides were incubated with the commercially available anti-CCR5 antibody 2D7.

Results

Promising compounds that were capable of binding Ab 2D7 with a high affinity are depicted below.

| | | 2D7 (1 μg/ml) | 2D7 (10 μg/ml) | 2D7 (0.1 μg/ml) |
|---|---|---|---|---|
| 447 | CQKEGLHYTC (SEQ ID NO: 101) | 2706 | 2943 | 261 |
| 443 | CQKEGLHYC (SEQ ID NO: 102) | 2636 | 3090 | 148 |
| 449 | CSQKEGLHYTC (SEQ ID NO: 103) | 2606 | 2889 | 99 |
| 1160 | CWDFGNTMCQKEGLHYTC (SEQ ID NO: 104) | 2469 | 2765 | 315 |
| 450 | CRSQKEGLHYTC (SEQ ID NO: 105) | 2364 | 2852 | 107 |
| 702 | CNTMGGGRSQKEGLHYTC (SEQ ID NO: 106) | 1580 | 2787 | 68 |
| 1159 | CQWDFGNTCQKEGLHYTC (SEQ ID NO: 107) | 1153 | 2636 | 213 |
| 719 | CFGNTMGGGRSQKEGLHYTC (SEQ ID NO: 108) | 678 | 2819 | 113 |
| 1158 | CAQWDFGNCQKEGLHYTC (SEQ ID NO: 109) | 416 | 2377 | 132 |

All compounds of the above Table comprise peptides bound to P2 or T3. All compounds were capable of binding antibody 2D7.

Conclusion: With this example we show that a method according to the invention is suitable for identifying mimics of CCR5, capable of binding 2D7, whereas linear peptides were not capable of binding 2D7.

Such peptides are further used in immunization experiments in order to elicit CCR5-specific antibodies capable of neutralizing HIV infection.

Example 2

Design and Preparation of Immunogenic Compounds Based on Interleukin 5

In order to design suitable test compounds, five series of compounds were generated. The compounds were subsequently incubated with a commercially available antibody capable of specifically binding IL5 (Antibody 39D10):

Series 1

Overlapping 18-mer sequences of the entire IL5 sequence were generated. The peptides were not coupled to a scaffold. None of these peptides were capable of binding 39D10 with acceptable affinity.

Series 2

Overlapping 13-mer sequences of the entire IL5 sequence were generated. Peptides were produced containing one 13-mer sequence and a N-terminal and C-terminal cysteine residue. If a 13-mer comprised a cysteine residue that was not intended for coupling, the cysteine was replaced by alanine. Subsequently, the peptides were coupled to a P2 scaffold via their N-terminal and C-terminal cysteine residues. The resulting compounds were subsequently incubated with Ab 39D10. Some compounds were capable of binding, but no favourable compound was found.

In series 3-series 5, the following two interleukin 5 sequences were taken into account:

Part-1, KKKSGEERRRVNQFLDY (SEQ ID NO:110)

Part-2, LIANETLRIPVPVHKNH (SEQ ID NO:111)

Of note, the fourth amino acid residues of Part-1, serine, is a cysteine residue in natural human IL5. In order to avoid coupling of the scaffolds to this cysteine, the cysteine was replaced by serine.

Series 3

In this series, the first three amino acid sequences and the last three amino acid residues of Part-1 and Part-2 were selected. Subsequently, C-terminal and N-terminal flanking sequences with a length of between 14 and 16 amino acid residues were selected. Peptides were produced containing one flanking sequence and a N-terminal and C-terminal cysteine residue. Subsequently, the peptides were coupled to a P2 scaffold via their N-terminal and C-terminal cysteine residues. The resulting compounds were subsequently incubated with Ab 39D10. Some compounds comprising a flanking sequence of Part-1 were capable of binding Ab 39D10.

Series 4

In this series flanking sequences derived from Part-1 were combined with flanking sequences derived from Part-2. 21-mers were produced according to the following schematic sequences:

CXXXXXXXXCXXXXXXXXC

CXXXXXXXCXXXXXXXXXC

CXXXXXXCXXXXXXXXXXC

CXXXXXCXXXXXXXXXXXC

CXXXXCXXXXXXXXXXXXC

CXXXCXXXXXXXXXXXXXC

CXXXXXXXXXCXXXXXXXC

CXXXXXXXXXXCXXXXXXC

CXXXXXXXXXXXCXXXXXC

CXXXXXXXXXXXXCXXXXC

CXXXXXXXXXXXXXCXXXC wherein the first stretch of X residues represents a flanking sequence derived from Part-1 and the second stretch of X residues represents a flanking sequence derived from Part-2. Hence, the lengths of the flanking sequences differ but the overall length of the resulting peptide is the same (21 amino acid residues). The peptides were coupled to a T3 scaffold. The resulting compounds were subsequently incubated with Ab 39D10. Various compounds were found with high binding affinity for Ab 39D10. These compounds are outlined below in more detail.

Series 5

Also in this series flanking sequences derived from Part-1 were combined with flanking sequences derived from Part-2. In this series the resulting peptides (containing a flanking sequence derived from Part-1 and a flanking sequence derived from Part-2) were of different length. The peptides were coupled to T3 via three cysteine residues and subsequently incubated with Ab 39D10. The results are outlined below in more detail.

Results

The following four peptides, coupled to T3, appear to have a high affinity for Ab 39D10:

| | | | |
|---|---|---|---|
| 1. | Ac-CEERRRVCANETLRIPVPCGSC (SEQ ID NO: 112) | (T3) | 1:1500 |
| 2. | Ac-CSGEERRRVCANETLRIPCGSC (SEQ ID NO: 113) | (T3) | 1:1500 |
| 3. | Ac-CEERRRVNQCANETLRIPCGSC (SEQ ID NO: 114) | (T3) | 1:2000 |
| 4. | Ac-CGEERRRCIANETLRIPCGSC (SEQ ID NO: 115) | (T3) | 1:4000 |

All four peptides contain a partial sequence of Part-1 and a partial sequence of Part-2.

These four peptides were used in immunization experiments in order to test whether they are capable of eliciting antibodies against whole human IL5. The peptides, which are all derived from human IL5, appeared to be capable of eliciting antibodies that showed strong cross reaction with whole human IL5 with antibody titers of 1:1500, 1:2000 and 1:4000 (calculated according to OD values that were 50% of the ODmax values).

Conclusion

Peptides comprising combinations of flanking sequences derived from different regions appear to most closely resemble a native IL5 epitope. These peptides were found with a screening method according to the invention.

Example 3

Design and Preparation of Peptidomimetics of FSH and Use thereof as Peptide-Vaccine In this experiment, polypeptides corresponding to the B3-loop of FSH were designed, wherein two amino acid residues have been replaced by a first and a second cysteine residue in the polypeptide which cysteines are attached to each other via a scaffold, wherein:

said first scaffold-attached cysteine residue is introduced at position CysIV+p located p residues C-terminal from the position that corresponds to amino acid CysIV in the wild-type B3-loop, wherein $5 \leq p \leq 12$;

said second scaffold-attached cysteine residue is introduced at position CysV−q located q residues N-terminal from the position that corresponds to amino acid CysV in the wild-type B3-loop, wherein $4 \leq q \leq 12$ and wherein (p−q) is −3, −2, −1, 0, 1, 2 or 3; and the length of said polypeptide is from amino acid at position CysIV+x to amino acid at position CysV+y, wherein $-5 \leq x \leq 1$ and $1 \leq y \leq 6$ under the provision that x+y=−1, 0, 1 or 2.

Peptides were synthesized by solid-phase peptide synthesis using a 4-(2',4'-dimethoxyphenyl-Fmoc-aminomethyl)-phenoxy (RinkAmide) resin (BACHEM, Germany) on a Syro-synthesizer (MultiSynTech, Germany). All amino acids were purchased and used as N-alpha-(Fmoc) protected with side-chain functionalities protected as N-t-Boc (KW), O-t-Bu (DESTY), N-Trt (HNQ), S-Trt (C), or N-Pbf (R) groups. A coupling protocol using a 6.5-fold excess of HBTU/HOBt/amino acid/DIPEA (1:1:1:2) in NMP with a 30 min. activation time using double couplings was employed. Acetylated peptides were cleaved from the resin by reaction with TFA (15 mL/g resin) containing 13.3% (w) phenol, 5% (v) thio-anisole, 2.5% (v) 1,2-ethanediol, and 5% (v) milliQ-H$_2$O for 2-4-h at room temperature, and subsequently precipitated with diethyl ether (at least 3× the volume of TFA). Crude peptides were purified by reversed-phase high performance liquid chromatography (RPC), either on a "DeltaPack" (25 or 40×100 mm inner diameter, 15 micrometer particle size, 100 A pore size; Waters, USA) or on a "XTERRA" (50×4.6 mm inner diameter, 2.5 micrometer particle size Waters, USA) RP-18 preparative C$_{18}$ column with a linear AB-gradient of 1-2% B/min where solvent A was 0.05% TFA in water and solvent B was 0.05% ACN. The correct primary ion molecular weight of the peptides was confirmed by electron-spray ionization mass spectrometry on a Micromass ZQ (Micromass, The Netherlands) or a VG Quattro II (VG Organic, UK) mass spectrometer. The polypeptides were either cyclized onto a T2 (1 h reaction of peptide and 1.05 equivalent of T2 in 20% acetonitril (ACN)/80% ammonium bicarbonate (20 mM), pH 7.8 at room temperature), or T4 scaffold (1 h reaction of peptide and 0.5 equivalent of T4 in 60% ACN/40% ammonium bicarbonate (20 mM), pH 7.8 at room temperature) or directly cyclized via SS-oxidation of the cysteines. The scaffolds were obtained from Sigma-Aldrich. In addition, a linear version of the polypeptide lacking the cysteines was prepared (see Table 4). Subsequently, female Wistar rats were immunized on day 0 with 400 uL of a ~2.5 mg/mL of the peptide or peptide-T-construct in PBS/CFA 1:1 (v/v) (PBS=Phosphate-Buffered Saline, CFA=Complete Freund's Adjuvance), followed by a booster (same quantity and concentration) at 4 weeks. Subsequently, the anti-peptide titers were determined after 6 weeks to check for immune response and finally the rats were bleeded after 8 weeks and the antisera collected. Antisera were analyzed in an FSH-binding ELISA (Greiner, PS; GDA-coating with 1 μg/mL of FSH (Biotrend)) using 2,2'-azine-di(ethylbenzthiazoline sulfonate) (ABTS) in combination with a peroxidase-labeled Goat-anti-rat serum as second antibody. Antibodies pAb 5215 (Biogenesis) and mAb 6602 (Medix Biochemicals) were included in the analysis as positive controls.

TABLE 4A

| Sample no. | Polypeptide[a] | Scaffold[b] |
|---|---|---|
| 1 | *CRVPGDAHHADSLC# (SEQ ID NO: 116) | m-T2 |
| 2 | *CRVPGDAHHADSLC# (SEQ ID NO: 116) | T4 |
| 3 | *CVRVPGAAHHADSLYC# (SEQ ID NO: 117) | m-T2 |
| 4 | *CVRVPGAAHHADSLYC# (SEQ ID NO: 117) | T4 |

TABLE 4A-continued

| Sample no. | Polypeptide[a] | Scaffold[b] |
|---|---|---|
| 5 | *YETCRVPGDAHHADSLCTYP# (SEQ ID NO: 118) | m-T2 |
| 6 | *YETCRVPGDAHHADSLCTYP# (SEQ ID NO: 118) | T4 |
| 7 | *TFKELVYETCRVPGAAHHADSLCTYPVATQAH# (SEQ ID NO: 119) | m-T2 |
| 8 | *KIQKTATFKELVYETCRVPGAAHHADSLCTYPVATQAHAGK# (SEQ ID NO: 120) | T4 |
| 9 | *CYTRDLVYKDPARPKIQKTC# (SEQ ID NO: 121) | T4 |
| 10 | *KIQKTATFKELVYETCRVPGAAHHADSLCTYPVATQAHAGK# (SEQ ID NO: 120) | m-T2 |
| 11 | *TQAHCGKADSDSTDC# (SEQ ID NO: 122) | T4 |
| 12 | *TFKELVYETCRVPGAAHHADSLCTYPVATQAH# (SEQ ID NO: 119) | None; SS cyclized |
| 13 | *TFKELVYETCRVPGAAHHADSLCTYPVATQAH# (SEQ ID NO: 119) | T4 |
| 14 | *TFKELVYETVRVPGCAHHADSLYTYPVATQAH# (SEQ ID NO: 123) | None; linear |

[a]sequence of the polypeptide is given in one letter abbreviation. * denotes N-terminus and # denotes C-terminus.
[b]m-T2 refers to meta-bis(bromomethyl)benzene and T4 refers to 1,2,4,5 tetrabromodurene.

Figure 2:
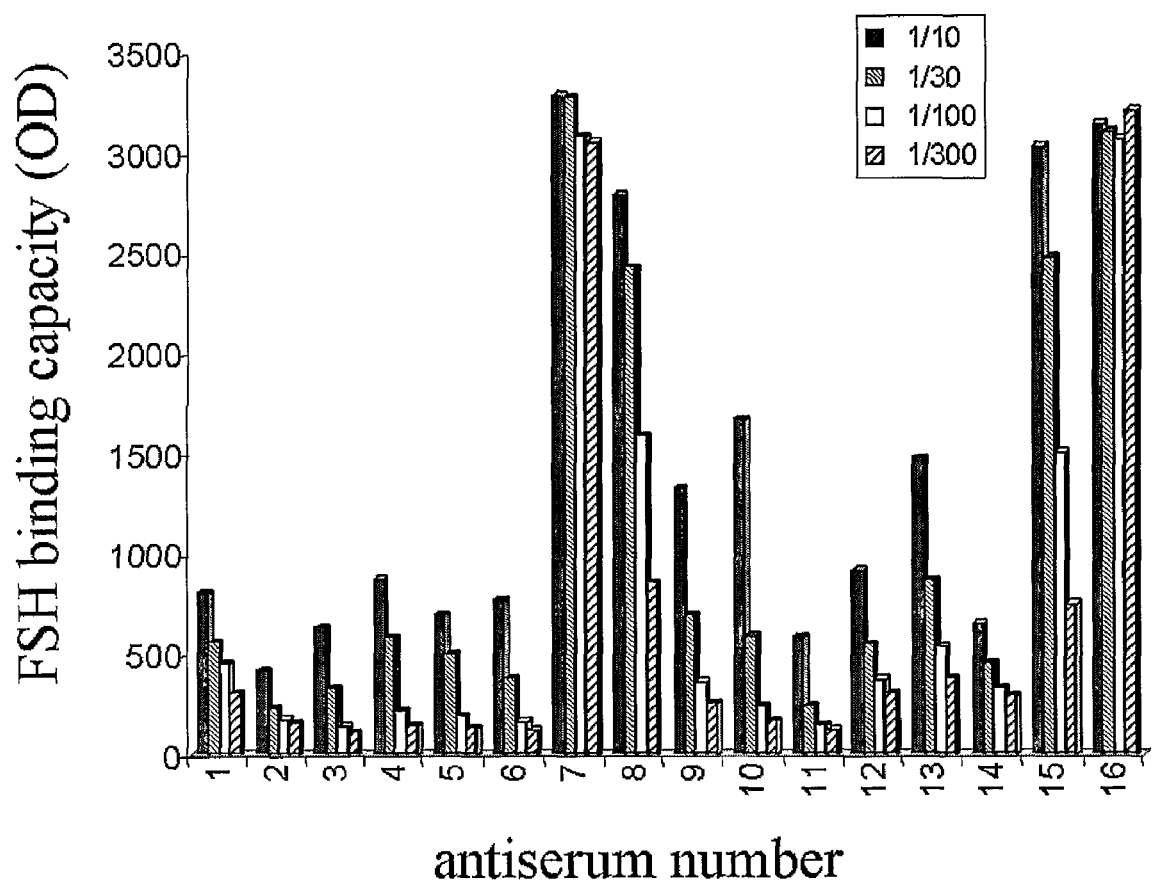
FIG. 2: Results of a vaccination experiment using peptidomimetics of FSH. Serum of rats immunized with the peptide compound indicated at the X-axis was analysed using ELISA to determine whether the peptide can induce an immune response against native FSH. Four serial dilutions of the serum were tested ($1/10$, $1/30$, $1/100$, and $1/300$). Polyclonal antibody 5215 (no. 15) and monoclonal antibody 6602 (no. 16) against FSH were used as positive control. Details are described in Example 3.

The results shown in FIG. 2 demonstrate the relevance of attaching a B3-derived polypeptide to a scaffold since neither the corresponding peptide cyclized via SS-oxidation nor the linear polypeptide are immunogenic by themselves.

Below, the same results are depicted with more detail in Tables 4B and 4C. Various values, such as the CLIPS positions p and q, are indicated.

TABLE 4B

Antibody responses from vaccination experiments with FSH-derived peptides of different length and surface region + corresponding neutralizing activities in FSH-stimulation assay.

| No. | Peptide Sequence + CLIPS | CLIPS-positions (p, q) | AA's in FSH (x, y) | Ab-titre (10 wks) 2 rats[b] | Neutr. FSH stimulat. assay[c] |
|---|---|---|---|---|---|
| 1 | *CRVPGDAHHADSLC# (SEQ ID NO: 116) + m-T2 | 10, 8 | 10, -8 | <(2x) | -(2x) |
| 2 | *CVRVPGAAHHADSLYC# (SEQ ID NO: 117) + m-T2 | 9, 7 | 9, -7 | <1 (2x) | -(2x) |
| 3 | *YETCRVPGDAHHADSLCTYP# (SEQ ID NO: 118) + m-T2 | 10, 8 | 7, -5 | <1 (2x) | -(2x) |
| 4 | *TFKELVYETCRVPGAAHHADSLCTYPVATQAH# (SEQ ID NO: 119) + m-T2 | 10, 8 | 1, 1 | <1; 4.0 | -; 1/64 |
| 5 | *KIQKTATFKELVYETCRVPGAAHHADSLCTYPVATQAHAGK# (SEQ ID NO: 120) + m-T2 | 10, 8 | -5, 4 | <1 (2x) | -(2x) |
| 6 | *CRVPGDAHHADSLC# (SEQ ID NO: 116) + T4 | 10, 8 | 10, -8 | <1 (2x) | -(2x) |
| 7 | *CVRVPGAAHHADSLYC# (SEQ ID NO: 117) + T4 | 9, 7 | 9, -7 | <1 (2x) | -(2x) |
| 8 | *YETCRVPGDAHHADSLCTYP# (SEQ ID NO: 118) + T4 | 10, 8 | 7, -5 | <1 (2x) | -(2x) |
| 9 | *KIQKTATFKELVYETCRVPGAAHHADSLCTYPVATQAHAGK# (SEQ ID NO: 120) T4 | 10, 8 | -5, 4 | 3.0; 2.5 | 1/16; - |
| 10 | *CYTRDLVYKDPARPKIQKTC# (SEQ ID NO: 121) + T4 | -19, 31 | -19, -31 | <1 (2x) | -(2x) |
| 11 | *TQAHCGKADSDSTDC# (SEQ ID NO: 122) + T4 | 33, -12 | 29, -12 | <1 (2x) | -(2x) |

[a] Amino acids printed in bold are substituents for native Cys-residues at these positions, amino acids printed underlined indicate the Cys-residues at which the CLIPS are attached.
[b] Antibody titres are given as $-^{10}$log values of the serum dilution at which the OD in the binding ELISA is still >3x the background-bD (1/10 dilution = 1, 1/100 = 2, 1/1000 = 3, 1/10 000 = 4, etc.).
[c] gives the highest dilution of purified serum (protG-column) at which full blocking of the the FSH-induced bioactivity is still observed (at 6 ng/mL FSH cell-stimulation).

TABLE 4C

Antibody responses from vaccination experiments with FSH-β3 loop derived peptides icw. different CLIPS (at position CysIV + p, CysV - q; length: CysIV + x, CysV + y) and corresponding neutralizing activities in Y1-cell bioassay.

| No. | Peptide Sequence + CLIPS | CLIPS-positions (p, q) | AA's in FSH (x, y) | Ab-titre (10 wks) 2 rats[b] | Neutr. FSH stimulat. assay[c] |
|---|---|---|---|---|---|
| 1 | *TFKELVYETCRVPGAAHHADSLCTYPVATQAH# (SEQ ID NO: 119) + m-T2 | 10, 8 | 10, -8 | 3.0; <1 | 1/16; - |
| 2 | *TFKELVYETCRVPGAAHHADSLCTYPVATQAH# (SEQ ID NO: 119) + SS | 10, 8 | 10, -8 | <1 (2x) | -(2x) |

TABLE 4C-continued

Antibody responses from vaccination experiments with FSH-β3 loop derived peptides icw. different CLIPS (at position CysIV + p, CysV − q; length: CysIV + x, CysV + y) and corresponding neutralizing activities in Y1-cell bioassay.

| No. | Peptide Sequence + CLIPS | CLIPS-positions (p, q) | AA's in FSH (x, y) | Ab-titre (10 wks) 2 rats[b] | Neutr. FSH stimulat. assay[c] |
|---|---|---|---|---|---|
| 3 | *TFKELVYET<u>C</u>RVPGAAHHADSL<u>C</u>TYPVATQ AH# (SEQ ID NO: 119) + T4 | 10, 8 | 10, −8 | <1 (2x) | − (2x) |
| 4 | *TFKELVYETRVPGCAHHADSLYTYPVATQ AH# (SEQ ID NO: 162) | n.a. | 10, −8 | <1 (2x) | − (2x) |

[a]Amino acids printed in bold are substituents for native Cys-residues at these positions, amino acids printed underlined indicate the Cys-residues at which the CLIPS are attached.
[b]Atitibody titres are given as $-^{10}$log values of the serum dilution at which the OD in the binding ELISA is still >3x the background-OD (1/10 dilution = 1, 1/100 = 2, 1/1000 = 3, 1/10 000 = 4, etc.).
[c]gives the highest dilution of purified serum (protG-column) at which full blocking of the the FSH-induced bioactivity is still observed (at 6 ng/mL FSH cell-stimulation).

The results clearly demonstrate that it is possible to generate immunogenic compounds derived from the beta3 loop of FSH (see compounds 4 and 9 in Table 4B and compound 1 in Table 4C). The immunogenic compounds give rise to the production of FSH-specific antibodies.

Example 4

Design and Preparation of Peptidomimetics of FSH and Use thereof as Peptide-Vaccine In this experiment, a set of polypeptides corresponding to the β3-loop of FSH, differing in length and chiral configuration of the cysteine residues for CLIPS-attachment, were designed and synthesized as described above. The polypeptides were cyclized onto an m-T2 (1 h reaction of peptide and 1.05 equivalent of m-T2 in 20% acetonitril/80% ammonium bicarbonate (20 mM), pH 7.8 at room temperature). Subsequently, female Wistar rats were immunized on day 0 with 400 uL of a ~2.5 mg/mL of the peptide or peptide-T-construct in PBS/CFA 1:1 (v/v) (PBS=Phosphate-Buffered Saline, CFA=Complete Freund's Adjuvance), followed by a booster (same quantity and concentration) at 4 weeks. Subsequently, the anti-peptide titers were determined after 6 weeks to check for immune response and finally the rats were bleeded after 10 weeks and the antisera collected. Antisera were analyzed in an FSH-binding ELISA (Greiner, PS; GDA-coating with 1 □g/mL of FSH (Biotrend)) using 2,2'-azine-di(ethylbenz-thiazoline sulfonate) (ABTS) in combination with a peroxidase-labeled Goat-anti-rat serum as second antibody. Antibodies pAb 5215 (Biogenesis) and mAb 6602 (Medix Biochemicals) were included in the analysis as positive controls.

TABLE 7

Antibody responses from vaccination experiments with various FSH-β3 loop m-T2 CLIPS-peptides (fixed CLIPS-position at CysIV + p, CysV − q) of variable length (CysIV + x, CysV + y) and corresponding neutralizing activities in Y1-cell bioassay.

| No. | Peptide Sequence + CLIPS | CLIPS-positions (p, q) | AA's in FSH (x, y) | Ab-titre (10 wks) 2 rats[b] | Neutr. FSH stimulat. assay[c] |
|---|---|---|---|---|---|
| 1 | *TFKELVYET<u>C</u>RVPGDAHHADSL<u>C</u>TYPVAT QAH# (SEQ ID NO: 124) + m-T2 | 10, 8 | 1, 1 | 3.0; 4.0 | 1/250; 1/500 |
| 6 | *TFKELVYET<u>C</u>RVPGAAHHADSL<u>C</u>TYPVAT QAH# (SEQ ID NO: 119) + T3/DTT | 10, 8 | 1, 1 | 3.5; <1 | 1/125; − |

[a]Amino acids printed in bold are substituents for native Cys-residues at these positions, amino acids printed underlined indicate the Cys-residues at which the CLIPS are attached.
[b]Antibody titres are given as $-^{10}$log values of the serum dilution at which the OD in the binding ELISA is still >3x the background-GD (1/10 dilution = 1, 1/100 = 2, 1/1000 = 3, 1/10 000 = 4, etc.).
[c]gives the highest dilution of purified serum (protG-column) at which full blocking of the the FSH-induced bioactivity is still observed (at 6 ng/mL FSH cell-stimulation).

From Table 7 it is concluded that a compound comprising peptide TFKELVYETCRVPGDAHHADSLCTYPVATQAH (SEQ ID NO:124) bound to scaffold T2 is preferred.

Moreover, a compound comprising peptide TFKELVYET-CRVPGAAHHADSLCTYPVATQAH (SEQ ID NO:119) bound to scaffold T3 is preferred.

Example 5

Design and Preparation of Structurally Optimized Peptidomimetics of FSH and Use thereof as Peptide-Vaccine In this experiment, a set of polypeptides corresponding to the B3-loop of FSH were structurally optimized using Ab-binding data from a replacement analysis study screened with the mAb's 5828 and 6602. The polypeptides were cyclized onto an m-T2 (1 h reaction of peptide and 1.05 equivalent of m-T2 in 20% acetonitril/80% ammonium bicarbonate (20 mM), pH 7.8 at room temperature). Subsequently, female Wistar rats were immunized on day 0 with 400 uL of a ~2.5 mg/mL of the CLIPS-peptide construct in PBS/CFA 1:1 (v/v) (PBS=Phosphate-Buffered Saline, CFA=Complete Freund's Adjuvance), followed by a booster (same quantity and concentration) at 4 weeks. Subsequently, the anti-peptide titers were determined after 6 weeks to check for immune response and finally the rats were bleeded after 10 weeks and the antisera collected. Antisera were analyzed in an FSH-binding ELISA (Greiner, PS; GDA-coating with 1 µg/mL of FSH (Biotrend)) using 2,2'-azine-di(ethylbenzthiazoline sulfonate) (ABTS) in combination with a peroxidase-labeled Goat-anti-rat serum as second antibody. Antibodies pAb 5215 (Biogenesis) and mAb 6602 (Medix Biochemicals) were included in the analysis as positive controls.

From Table 8 it is concluded that a compound comprising peptide TFKELVYETCRVPGDAHHADKLCTYP-VATQAH (SEQ ID NO:125) bound to scaffold T2 is preferred.

Moreover, a compound comprising peptide TFKELVYET-CRVPGDAHKADSLCTYPVATQAH (SEQ ID NO:41) bound to scaffold T2 is preferred.

Example 6

Design and Preparation of Peptidomimetics of h-CG and Use thereof as Peptide-Vaccine In this experiment, polypeptides corresponding to the B3-loop of hCG were designed and synthesized as described above. The polypeptides were either cyclized onto a T2 (1 h reaction of peptide and 1.05 equiv of T2 in 20% ACN/80% amm. bicarb (20 mM), pH 7.8 at room temperature), or T4 scaffold (1 h reaction of peptide and 0.5 equiv. of T4 in 60% ACN/40% amm. bicarb (20 mM), pH 7.8 at room temperature) or directly cyclized via SS-oxidation of the cysteines. In addition, a linear version of the polypeptide lacking cysteines was prepared (see Table 5). Rats were immunized with the various peptides or peptide-constructs as described for the FSH-peptide mimics in Example 1. Commercial antibody CG-B2 against hCG (obtained from Imgen) were included in the analysis as positive controls in order to validate the coating of hCG (obtained from Biotrend) on the ELISA-surface.

TABLE 9A

| Sample no. | Polypeptide[a] | Scaffold[b] |
|---|---|---|
| 1 | *NYRDVRFESCRLPGAPRGVNPVCSYAVALSAQ# (SEQ ID NO: 126) | m-T2 |
| 2 | *NYRDVRFESCRLPGAPRGVNPVCSYAVALSAQ# (SEQ ID NO: 126) | None; SS-cyclized |

TABLE 8

Antibody responses from vaccination experiments with FSH-β3 loop m-T2 CLIPS-peptides + corresponding neutralizing activities in Y1-cell bioassay.

| No. | Peptide Sequence + CLIPS | CLIPS- positions (p, q) | AA's in FSH (x, y) | Ab-titre (10 wks) 2 rats[b] | Neutr. FSH stimulat. assay[c] |
|---|---|---|---|---|---|
| 1 | *TFKELVYETCRVPGDAHHADSLCTYPVATQAH# (SEQ ID NO: 124) + m-T2 | 10, 8 | 1, 1 | 1.5; 3.0 | 1/2; 1/4 |
| 2 | *TFKELVYETCRVPGDAHHADKLCTYPVATQAH# (SEQ ID NO: 125) + m-T2 | 10, 8 | 1, 1 | 3.5; 2.0 | 1/64; 112 |
| 3 | *TFKELVYETCRVPGDAHKADSLCTYPVATQAH# (SEQ ID NO: 41) + m-T2 | 10, 8 | 1, 1 | >4.5; <1 | 1/1000; - |

[a]Amino acids printed in bold are substituents for native Cys-residues at these positions, amino acids printed underlined indicate the Cys-residues at which the CLIPS are attached.
[b]Antibody titres are given as $-^{10}$log values of the serum dilution at which the OD in the binding ELISA is still >3x the background-OD (1/10 dilution = 1, 1/100 = 2, 1/1000 = 3, 1/10 000 = 4, etc.).
[c]gives the highest dilution of purified serum (protG-column) at which full blocking of the the FSH-induced bioactivity is still observed (at 6 ng/mL FSH cell-stimulation).

TABLE 9A-continued

| Sample no. | Polypeptide[a] | Scaffold[b] |
|---|---|---|
| 3 | *NYRDVRFESCRLPGAPRGVNPVCSYAVALSAQ# (SEQ ID NO: 126) | T4 |
| 4 | *NYRDVRFESIRLPGAPRGVNPVVSYAVALSAQ# (SEQ ID NO: 127) | None; linear |
| 5 | *VVANTRDVRFESCRLPGAPRGVNPVCSYAVALSAQAAL# (SEQ ID NO: 128) | m-T2 |
| 6 | *VVANYRDVRFESCRLPGAPRGVNPVCSYAVALSAQAAL# (SEQ ID NO: 128) | T4 |

[a] sequence of the polypeptide is given in one letter abbreviation. * denotes N-terminus and # denotes C-terminus.
[b] m-T2 refers to meta-dibromobenzene; T4 refers to 1,2,4,5 tetrabromodurene.

Figure 3:
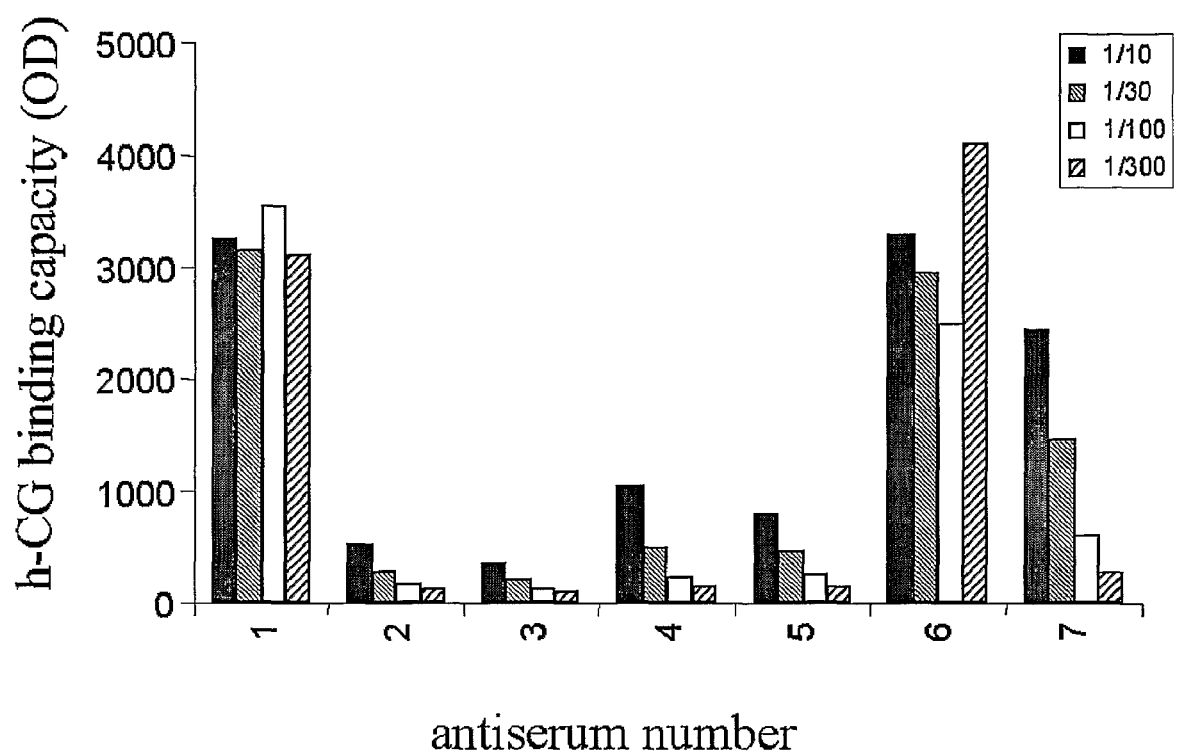
FIG. 3: Results of a vaccination experiment using peptidomimetics of hCG. Serum of rats immunized with the peptide compound indicated at the X-axis (see Table 5 for the different peptides and scaffolds used) was analysed using ELISA to determine whether the peptide can induce an immune response against native hCG. Various serial dilutions of the serum were tested. Antibody hCG-B2 (no. 7) was used as positive control. Details are described in Example 6.
Figure 4:
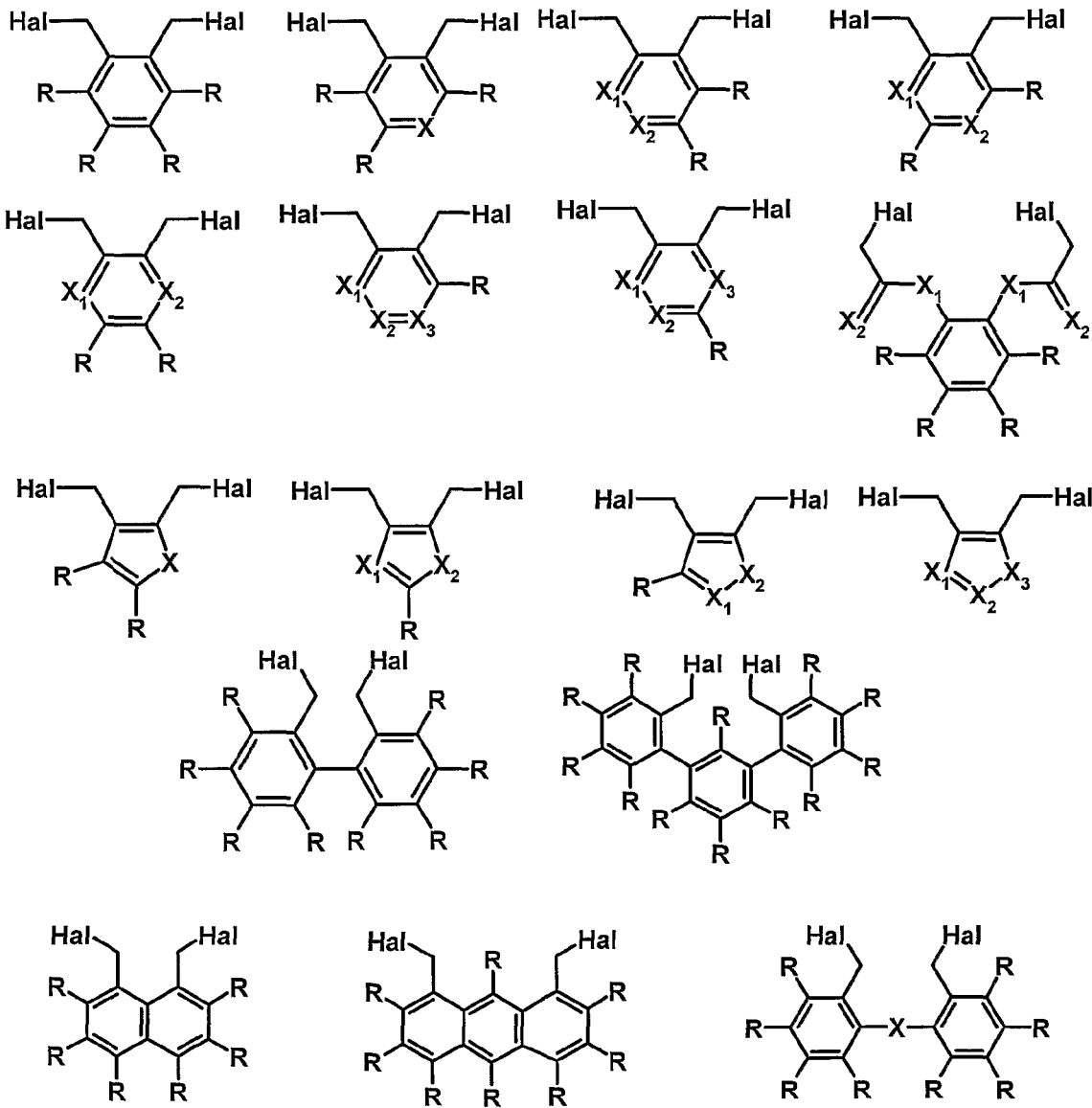
FIG. 4: Aromatic scaffolds with ortho-, meta-, or para-positioning of two halomethyl groups. Hal refers to chlorine, bromo, or iodine atoms.
1,2-bis(halomethyl)benzene and other regioisomers
3,4-bis(halomethyl)pyridine (X=N) and other regioisomers
3,4-bis(halomethyl)pyridazine (X=N) and other regioisomers
4,5-bis(halomethyl)pyrimidine (X=N) and other regioisomers
4,5-bis(halomethyl)pyrazine (X=N) and other regioisomers
4,5-bis(halomethyl)-1,2,3-triazine (X=N) and other regioisomers
5,6-bis(halomethyl)-1,2,4-triazine (X=N) and other regioisomers
3,4-bis(halomethyl)pyrrole (X=N), -furan (X=O), -thiophene (X=S) and other regioisomers
4,5-bis(halomethyl)imidazole (X=N,N), -oxazole (X=N,O), -thiazol (X=S) and other regioisomers
4,5-bis(halomethyl)-3H-pyrazole (X=N,N), -isooxazole (X=N,O), -isothiazol (X=S) and other regioisomers
1,2-bis(bromomethylcarbonylamino)benzene ($X_1$=NH, $X_2$=O)
2,2'-bis(halomethyl)biphenylene
2,2"-bis(halomethyl)terphenylene
1,8-bis(halomethyl)naphthalene
1,10-bis(halomethyl)anthracene
Bis(2-halomethylphenyl)methane
Figure 5:
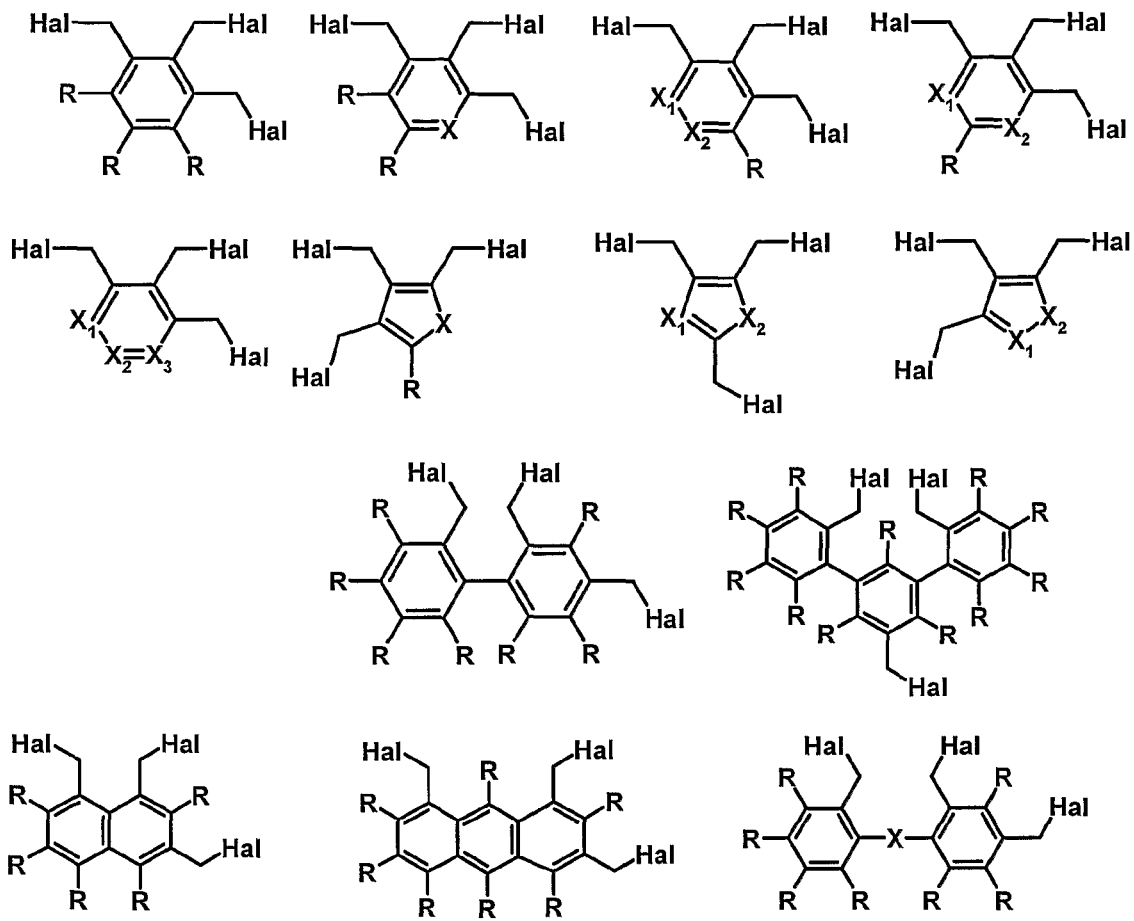
FIG. 5: Aromatic scaffolds with ortho-, meta-, or para-positioning of three halomethyl groups:
1,2,3-tris(halomethyl)benzene and other regioisomers
2,3,4-tris(halomethyl)pyridine (X=N) and other regioisomers
2,3,4-tris(halomethyl)pyridazine (X=N) and other regioisomers
3,4,5-tris(halomethyl)pyrimidine (X=N) and other regioisomers
4,5,6-tris(halomethyl)-1,2,3-triazine (X=N) and other regioisomers
2,3,4-tris(halomethyl)pyrrole (X=N), -furan (X=O), -thiophene (X=S) and other regioisomers
2,4,5-bis(halomethyl)imidazole (X=N,N), -oxazole (X=N,O), -thiazol (X=S) and other regioisomers
3,4,5-bis(halomethyl)-1H-pyrazole (X=N,N), -isooxazole (X=N,O), -isothiazol (X=S) and other regioisomers
2,4,2'-tris(halomethyl)biphenylene
2,3',2"-tris(halomethyl)terphenylene
1,3,8-tris(halomethyl)naphthalene
1,3,10-tris(halomethyl)anthracene
Bis(2-halomethylphenyl)methane
Figure 6:
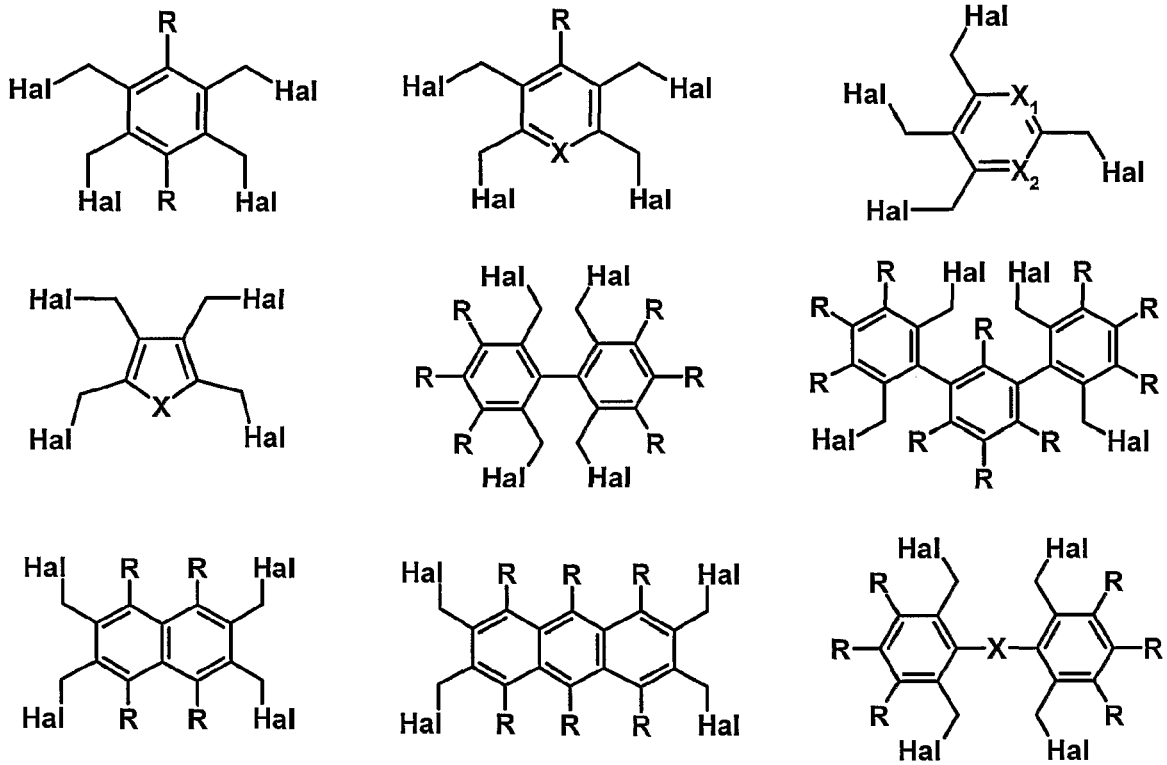
FIG. 6: Aromatic scaffolds with ortho-, meta-, or para-positioning of four bromomethyl groups.

The results shown in FIG. 3 demonstrate the relevance of attaching a B3-derived polypeptide to a scaffold since neither the corresponding peptide cyclized via SS-oxidation nor the linear polypeptide are immunogenic by themselves.

Below, the same results are depicted with more detail in Table 9B. Various values, such as the CLIPS positions p and q, are indicated.

Example 7

Design and Preparation of Peptidomimetics of hCG and Use thereof as Peptide-Vaccine In this experiment, a set of polypeptides corresponding to the β3-loop of hCG, differing in length and positions of the cysteine residues for CLIPS-attachment, were designed and synthesized as described above. The polypeptides were cyclized onto an m-T2 (1 h reaction of peptide and 1.05 equivalent of T2 in 20% acetonitril/80% ammonium bicarbonate (20 mM), pH 7.8 at room temperature). Subsequently, female Wistar rats were immunized on day 0 with 400 uL of a ~2.5 mg/mL of the peptide or peptide-T-construct in PBS/CFA 1:1 (v/v) (PBS=Phosphate-Buffered Saline, CFA=Complete Freund's Adjuvance), followed by a booster (same quantity and concentration) at 4 weeks. Subsequently, the anti-peptide titers were determined after 6 weeks to check for immune response and finally the rats were bleeded after 10 weeks and the antisera collected. Antisera were analyzed in an FSH-binding ELISA (Greiner, PS; GDA-coating with 1 □g/mL of hCG (Biotrend)) using 2,2'-azine-di(ethylbenzthiazoline sulfonate) (ABTS) in combination with a peroxidase-labeled Goat-anti-rat serum as second antibody. Antibody B2 was included in the analysis as positive control.

TABLE 9B

Antibody responses from vaccination experiments with hCG-β3 loop derived peptides icw. different CLIPS + corresponding neutralizing activities in hCG bioassay.

| No. | Peptide Sequence + CLIPS | CLIPS-positions (p, q) | AA's hCG (x, y) | Ab-titre (10 wks) 2 rats[b] | Neutr. hCG-stimulat. assay |
|---|---|---|---|---|---|
| 1 | *NYRDVRFES<u>C</u>RLPGAPRGVNPV<u>C</u>SYAVALSAQ# (SEQ ID NO: 36) + m-T2 | 10, 8 | 1, 1 | 4.0; <1 | -(2x) |
| 2 | *NYRDVRFES<u>C</u>RLPGAPRGVNPV<u>C</u>SYAVALSAQ# (SEQ ID NO: 126) + SS | 10, 8 | 1, 1 | <1; 1.0 | -(2x) |
| 3 | *NYRDVRFES<u>C</u>RLPGAPRGVNPV<u>C</u>SYAVALSAQ# (SEQ ID NO: 126) + T4 | 10, 8 | 1, 1 | <1 (2x) | -(2x) |
| 4 | *NYRDVRFESIRLPGAPRGVNPVVSYAVALSAQ# (SEQ ID NO: 127) | n.a. | 1, 1 | <1 (2x) | -(2x) |
| 5 | *VVANYRDVRFES<u>C</u>RLPGAPRGVNPV<u>C</u>SYAVALSAQAAL# (SEQ ID NO: 128) + m-T2 | 10, 8 | 1, 1 | <1 (2x) | -(2x) |
| 6 | *VVANYRDVRFES<u>C</u>RLPGAPRGVNPV<u>C</u>SYAVALSAQAAL# (SEQ ID NO: 128) + T4 | 10, 8 | 1, 1 | 3.0; <1 | -(2x) |

[a] Amino acids printed in bold are substituents for native Cys-residues at these positions, amino acids printed underlined indicate the Cys-residues at which the CLIPS are attached.
[b] Antibody titres are given as $-^{10}$log values of the serum dilution at which the OD in the binding ELISA is still >3x the background-OD (1/10 dilution = 1, 1/100 = 2, 1/1000 = 3, 1/10 000 = 4, etc.)..).
[c] means that 10-fold diluted serum is able to block hCG-induced cell-stimulation (1 and 5 ng/mL hCG);
"-" means that no hCG-blocking effect was observed.

TABLE 10

Antibody responses from vaccination experiments with hCG-β3
loop m-T2 CLIPS-peptides (CLIPS at CysIV + p, CysV − q)
of different peptide length (CysIV + x, CysV + y) and
corresponding neutralizing activities in hCG-bioassay.

| No. | Peptide Sequence + CLIPS | CLIPS-positions (p, q) | AA's hCG (x, y) | Ab-titre (9 wks) 2 rats[b] | Neutr. hCG-stimulat. assay |
|---|---|---|---|---|---|
| 5 | *NYRDVRFES<u>C</u>RLPGAPRGVNPV<u>C</u>SYAVALSAQ# (SEQ ID NO: 126) + m-T2 | 8, 6 | 1, 1 | 1.9 (2x) | − (2x) |
| 6 | *b NYRDVRFES<u>C</u>RLPGAPRGVNPV<u>C</u>SYAVALSAQA# (SEQ ID NO: 129) + m-T2 | 8, 6 | 0, 2 | <1 (2x) | − (2x) |
| 7 | *VANYRDVRFES<u>C</u>RLPGAPRGVNPV<u>C</u>SYAVALSAQAA# (SEQ ID NO: 130) + m-T2 | 8, 6 | −1, 3 | <1; 1.9 | − (2x) |
| 8 | *NYRDVRFES<u>C</u>RLPGDPRGVNPV<u>C</u>SYAVALSAQ# (SEQ ID NO: 131) + m-T2 | 8, 6 | 1, 1 | <1 (2x) | − (2x) |
| 8 | *NYRDVRFES<u>C</u>RLPGCPRGVNPV<u>C</u>SYAVALSAQ (SEQ ID NO: 132) # + m-T2<br>                   S<br>                   S<br>*NYRDVRFES<u>C</u>RLPGCPRGVNPV<u>C</u>SYAVALSAQ# (SEQ ID NO: 132) + m-T2 | 8, 6<br><br><br>8, 6 | 1, 1<br><br><br>1, 1 | 2.9; 1.8 | +, − |

[a]Amino acids printed in bold are substituents for native Cys-residues at these positions, amino acids printed underlined indicate the Cys-residues at which the CLIPS are attached.
[b]Antibody titres are given as −[10]log values of the serum dilution at which the OD in the binding ELISA is still >3x the background-OD (1/10 dilution = 1, 1/100 = 2, 1/1000 = 3, 1/10 000 = 4, etc.).
[c]"+" means that 10-fold diluted serum is able to block hCG-induced cell-stimulation (1 and 5 ng/mL hCG);
"−" means that no hCG-blocking effect was observed.

From Table 10 it is concluded that a compound comprising peptide

```
    *NYRDVRFESCRLPGCPRGVNPVCSYAVALSAQ#  (SEQ ID NO: 132)+ m·T2
                   S
                   S
    *NYRDVRFESCRLPGCPRGVNPVCSYAVALSAQ#  (SEQ ID NO: 132)+ m·T2
``` bound to scaffold T2 is preferred.

Example 8

Design and Preparation of Peptidomimetics of VEGF-A and Use thereof as Peptide-Vaccine In this experiment, a set of polypeptides corresponding to the β5-turn-B6 loop of VEGF-A (corresponding to β3-loop of FSH en hCG), differing in length and positions of the cysteine residues for CLIPS-attachment, were designed and synthesized as described above. The polypeptides were cyclized onto an m-T2 (1 h reaction of peptide and 1.05 equivalent of T2 in 20% acetonitril/80% ammonium bicarbonate (20 mM), pH 7.8 at room temperature). Subsequently, female Wistar rats were immunized on day 0 with 400 uL of a ~2.5 mg/mL of the peptide or CLIPS-peptide-construct in PBS/CFA 1:1 (v/v) (PBS=Phosphate-Buffered Saline, CFA=Complete Freund's Adjuvance), followed by a booster (same quantity and concentration) at 4 weeks. Subsequently, the anti-peptide titers were determined after 6 weeks to check for immune response and finally the rats were bleeded after 9 weeks and the antisera collected. Antisera were analyzed in an VEGF-binding ELISA (Greiner, PS; GDA-coating with 0.1 μg/mL of VEGF-A using 2,2'-azine-di(ethylbenzthiazoline sulfonate) (ABTS) in combination with a peroxidase-labeled Goat-anti-rat serum as second antibody. mAb 293 was included in the analysis as positive control.

TABLE 11

Antibody responses from vaccination experiments with VEGF-A
β5-turn-β6 loop m-T2 CLIPS-peptides with different CLIPS-
position (CysIV + p, CysV − q) and different peptide length
(CysIV + x, CysV + y, and corresponding neutralizing
activities in VEGF-proliferation assay.

| No. Peptide Sequence + CLIPS | CLIPS-positions (p, q) | AA's hCG (x, y) | Ab-titre (9 wks) 2 rats[b] | Neutr. VEGF-prolif. assay |
|---|---|---|---|---|
| 1 *ESNITMQIMRIKPHQGQHIGEMSFLQH# (SEQ ID NO: 133) + m-T2 | n.a. | 5, −3 | >1.8 (2x) | − (2x) |
| 2 *ESNCTMQIMRIKPHQGQHIGEMSCLQH# (SEQ ID NO: 134) + m-T2 | 8, 6 | 5, −3 | >2.8 (2x) | + (2x) |
| 3 *ESNITCQIMRIKPHQGQHIGECSFLQH# (SEQ ID NO: 135) + m-T2 | 10, 8 | 5, −3 | >2.8 (2x) | +, − |
| 4 *ESNITMQCMRIKPHQGQHICEMSFLQH# (SEQ ID NO: 136) + m-T2 | 12, 10 | 5, −3 | >2.8; <1.8 | +, − |
| 5 *ESNITMQICRIKPHQGQHCGEMSFLQH# (SEQ ID NO: 137) + m-T2 | 13, 11 | 5, −3 | >1.8; <1.8 | nd |
| 6 *EESNITMQIMRIKPHQGQHIGEMSFLQHN# (SEQ ID NO: 138) | n.a. | 4, −2 | >2.8; <1.8 | − (2x) |
| 7 *EESNCTMQIMRIKPHQGQHIGEMSCLQHN# (SEQ ID NO: 139) + m-T2 | 8, 6 | 4, −2 | >2.8 (2x) | +, − |
| 8 *EESNITCQIMRIKPHQGQHIGECSFLQHN# (SEQ ID NO: 140) + m-T2 | 10, 8 | 4, −2 | >2.8; <1.8 | +, − |
| 9 *EESNITMQCMRIKPHQGQHICEMSFLQHN# (SEQ ID NO: 141) + m-T2 | 12, 10 | 4, −2 | >1.8; <1.8 | nd |
| 10 *EESNITMQICRIKPHQGQHCGEMSFLQHN# (SEQ ID NO: 142) + m-T2 | 13, 11 | 4, −2 | <1.8 (2x) | nd |

[b]Antibody titres are given as number of 10-fold dilutions for which the OD (mAb-binding ELISA) > 3x times OD-background.
[c]"+" means that 10-fold diluted serum is able to block cell-proliferation induced by addition of 20 ng/mL VEGF;
"−" means that no cell-proliferation inhibition was observed at 20 ng/mL VEGF.

From Table 11 it is concluded that a compound comprising peptide ESNCTMQIMRIKPHQGQHIGEMSCLQH (SEQ ID NO:134) bound to scaffold T2 is preferred.

Moreover, a compound comprising peptide EESNCTMQIMRIKPHQGQHIGEMSCLQHN (SEQ ID NO:139) bound to scaffold T2 is preferred.

Conclusion: CLIPS positions 8, 6 (p=8 and q=6) en 10, 8 (p=10 and q=8) are preferred.

TABLE 12

Overview of Cys-knot Protein Sub-Families

Glycoprotein Hormone-α Family

Glycoprotein Hormone (or gonadotropin)-α 1,2(GLHA-1,2)
Glycoprotein Hormone-β Family Choriogonadotropin-β (β-CG)
Gonadotropin-β 1,2 (GTH-I,II)
Follicle Stimulating Hormone (or follotropin)-β (FSH-β)
Luteinizing Hormone-β (or lutropin)-β (β-LH)
Thyroid Stimulating Hormone (or thyrotropin)-β (TSH)
Contactin-Associated Protein-like 2 precursor (CTA-2)
Glycoprotein Hormone beta-5 precursor (GPB-5)

TABLE 12-continued

Overview of Cys-knot Protein Sub-Families

Nerve Growth Factor Family

Nerve Growth Factor (NGF)
Neurotrophin-3,4,5,7 (NT-3,4,5,7; HDNF)
Brain-derived Neurotropic Factor (BDNF)
PDGF-family Platelet-derived Growth FactorA,B-1,2 (PDGF-A,B-1,2)
PDGF-related transforming protein sis (TSIS,_SMSAV, P28SIS)Placenta Growth Factor (PLGF)
Vascular Endothelial Growth Factor A,B,C,D,H (VGEF-A,B,C,D,H)
Vascular Endothelial Growth Factor Toxin (TXVE, SVVEGF, ICPP)
Transforming Growth Factor Superfamily Transforming Growth Factor-beta 1-5 (TGFβ 1-5)
Activin-β (Inhibin-β)
ATP-dependent CLP-protease ATP-binding subunit CLPX (CLPX)
Bone Morphogenetic protein 2-8,10,15 (BMP 2-8,10,15)
60A Protein Precursor (Glass Bottom Boat Protein, 60A)
CET-1 *Caenorphabditis Elegans*
Decapentaplegic Protein Precursor (DECA)
DVR1-Protein Precursor (Vegital Hemisphere VG1 Protein)
Dorsalin-1 Precursor (DSL1)
XNR-1,2,4 (*Xenopus Laevis*)
ZNR-1 *Brachydanio Rerio* (Zebrafish)
VG1-*Gallus Gallus* (Chicken)

TABLE 12-continued

Overview of Cys-knot Protein Sub-Families

Placental Bone Morphogenetic proteinNodal precursor (NODA)
Norrie Disease Protein (NDP)
Prostate Differentation Factor (PDF)
(Embryonic) Growth Differentiation Factor 1-9 (GDF-1-9)
Glial Cell Line-derived Neurotrophic Factor Precursor (GDNF)
Left-right determining factor-b precursor (lefty-b protein, LFTB)
Megakaryocyte Stimulating Factor (MSF)
Mucin-2 precursor (Intestinal Mucin-2)
Muellerian Inhibiting Factor (MIS)
Neurturin Precursor (NRTN)
Persephin Precursor (PSPN)
Sclerostin (SOST)
Screw Protein Precursor (SCW)
Univin Precursor (UNIV)

TABLE 13

Alignment of various members of the cys-knot protein family

| | N-teminus | CysI (B1-loop) | CysII | CysIII (B2-loop) |
|---|---|---|---|---|
| hGLHA | PDVQDCPE | CTLQENPFFSQPGAPILQ | CMGC | CFSRAYPTPLRSKKTMLVQKNVTSESTC |
| hFSH-β | S | CELTNITIAIEKEECRFCISINTTW | CAGY | CYTRDLVYKDPARPKIQKT |
| hCG-β | SKEPLRPR | CRPINATLAVEKEGCPVCITVNTTI | CAGY | CPTMTRVLQGVLPALPQVV |
| hTSH-β | F | CIPTEYTMHIERRECAYCLTINTTI | CAGY | CMTRDINGKLFLPKYALSQDV |
| hLH-β | SREPLRPW | CHPINAILAVEKEGCPVCITVNTTI | CAGY | CPTMMRVLQAVLPPLPQVV |
| hNGF | SSSHPIFHRGEFSV | CDSVSVWVGDKTTATDIKGKEVMVLGEVNINNSVFKQYFFETK | CRDPNPVDSG | CRGIDSKHWNSY |
| hBDNF | HSDPARRGELSV | CDSISEWVTAADKKTAVDMSGGTVTVLEKVPVSKGQLKQYFYETK | CNPMGYTKEG | CRGIDKRHWNSQ |
| hVEGF-a | APMAEGGGQNHHEVVKFMDVYQRSY | CHPIETLVDIFQEYPDEIEYIFKPSCVPLMR | CGGC | CNDEGLE |
| hPLGF | SEVEVVPFQEVWGRSY | CRALERLVDVVSEYPSEVEHMFSPSCVSLLR | CTGC | CGDENLH |
| hPDGF-a | SIEEAVPAV | CKTRTVIYEIPRSQVDPTSANFLIWPPCVEVKR | CTGC | CNTSSVK |
| hPDGF-b | SLGSLTIAEPAMIAE | CKTRTEVFEISRRLIDRTNANFLVWPPCVEVQR | CSGC | CNNRNVQ |
| hTGFβ-1 | ALDTNYCFSSTEKN | CCVRQLYIDFRKDLGWKWIHEPKGYHANF | CLGP | CPYIWSLDTQYSKVLALYNQHNPGASAAPC |
| hBMP-2 | QAKHKQRKRLKSS | CKRHPLYVDFSDVGWNDWIVAPPGYHAFY | CHGE | CPFPLADHLNSTNHAIVQTLVNSVNSKIPKAC |
| hBMP-7 | STGSKQRSQNRSKTPKNQEALRMANVAENSSSDQRQA | CKKHELYVSFRDLGWQDWIIAPEGYAAYY | CEGE | CAFPLNSYMNATNHAIVQTLVHFINPETVPKPC |
| hBMP-10 | NAKGNY | CKRTPLYIDFKEIGWDSWIIAPPGYEAYE | CRGV | CNYPLAEHLTPTKHAIIOALVHLKNSQKASKAC |
| hGDNF | SPDKQMAVLPRRERNRQAAAANPENSRGKGRRGQRGKNRG | CVLTAIHLNVTDLGLGYETKEELIFRY | CSGS | CDAAETTYDKILKNLSRNRRLVSDKVGQAC |
| hGDF-5 | APLATRQGKRPSKNLKAR | CSRKALHVNFKDMGWDDWIIAPLEYEAFH | CEGL | CEFPLRSHLEPTNHAVIQTLMNSMDPESTPPTC |
| hGDF-15 | ARARNGDHCPLGPGR | CCRLHTVRASLEDLGWADWVLSPREVQVTM | CIGA | CPSQFPAANMHAQIKTSLHRLKPDTVPAPC |

TABLE 13-continued

Alignment of various members of the cys-knot protein family

|  | CysIV (B3-loop) | CysV | CysVI + C-terminus |
|---|---|---|---|
| hGLHA | CVAKSYNRVTVMGGFKVENHTA | CH | CSTCYYHKS |
| hFSH-β | CTFKELVYETVRVPGCAHHADSLYTYPVATQ | CH | CGKCDSDSTDCTVRGLGPSYCSFGEMKE |
| hCG-β | CNYRDVRFESIRLPGCPRGVNPVVSYAVALS | CQ | CALCRRSTTDCGGPKDHPLTCDDPRFQDSSSSKAPPPSLPSPSRLPGPSDTPILPQ |
| hTSH-β | CTYRDFIYRTVEIPGCPLHVHPYFSYPVALS | CK | CGKCNTDYSDCIHEAIKTNYCTKPQKSYLVGFSV |
| hLH-β | CTYRDVRFESIRLPGCPRGVDPVVSFPVALS | CR | CGPCRRSTSDCGGPKDHPLTCDHPQLSGLLFL |

|  | CysIV (B3-loop) | CysV | CysVI |
|---|---|---|---|
| hNGF | CTTTHTFVKALTMDGKQAAWRFIRIDTA | CV | CVLSRKAVRRA |
| hBDNF | CRTTQSYVRALTMDSKKRIGWRFIRIDTS | CV | CTLTIKRGR |
| hVEGF-a | CVPTEESNITMQIMRIKPHQGQHIGEMSFLQHNK | CE | CRPKKDR |
| hPLGF | CVPVETANVTMQLLKIRSGDRPSYVELTFSQHVR | CE | CRPLREK |
| hPDGF-a | CQPSRVHHRSVKVAKVEYVRKKPKLKEVQVRLEEHLE | CA | CATTSLN |
| hPDGF-b | CRPTQVQLRPVQVRKIEIVRKKPIFKKATVTLEDHLA | CK | CETVAAA |
| hTGFβ-1 | CVPQALEPLPIVYYYVGRKPKVEQLSNMIVRS | CK | CS |
| hBMP-2 | CVPTELSAISMLYLDENEKVVLKNYQDMVVEG | CG | CR |
| hBMP-7 | CAPTQLNAISVLYFDDSSNVILKKYRNMVVRA | CG | CH |
| hBMP-10 | CVPTKLEPISILYLDKGVVTYKFKYEGMAVSE | CG | CR |
| hGDNF | CRPIAFDDDLSFLDDNLVYHILRKHSAKR | CG | CI |
| hGDF-5 | CVPTRLSPISILFIDSANNVVYKQYEDMVVES | CG | CR |
| hGDF-15 | CVPASYNPMVLIQKTDTGVSLQTYDDLLAKD | CH | CI |

Table 14: Position of conserved cysteines in various members of the Cys-knot protein family. The numbers between brackets refer to the Pfam databases of multiple alignments of protein domains or conserved protein regions. The first column lists all cysteines residues found within the protein. The second column gives the designation of the six conserved cysteines residues (CysI to CysVI). The other columns indicates the corresponding amino acid position (starting from the N-terminus) for individual subfamily members.

TABLE 14A

Glycoprotein Hormone-Alpha Subfamily (PF00236)

|  |  | hCG-a |
|---|---|---|
| C-1 |  | 7 |
| C-2 | CysI | 10 |

TABLE 14A-continued

Glycoprotein Hormone-Alpha Subfamily (PF00236)

|  |  | hCG-a |
|---|---|---|
| C-3 | CysII | 28 |
| C-4 |  | 31 |
| C-5 | CysIII | 32 |
| C-6 |  | 59 |
| C-7 | CysIV | 60 |
| C-8 | CysV | 82 |
| C-9 | CysVI | 84 |
| C-10 |  | 87 |

TABLE 14B

Glycoprotein Hormone-Beta Subfamily (PS00689/PS00261)

|  |  | hCG-beta | FSH-beta |
|---|---|---|---|
| C-1 | CysI | 9 | 3 |
| C-2 |  | 23 | 17 |
| C-3 |  | 26 | 20 |
| C-4 | CysII | 34 | 28 |
| C-5 | CysIII | 38 | 32 |
| C-6 | CysIV | 57 | 51 |
| C-7 |  | 72 | 66 |
| C-8 | CysV | 88 | 82 |
| C-9 | CysVI | 90 | 84 |
| C-10 |  | 93 | 87 |
| C-11 |  | 100 | 94 |
| C-12 |  | 110 | 104 |

TABLE 14C

NGF-subfamily (PF00243)

|  |  | NGF | BDNF |
|---|---|---|---|
| C-1 | CysI | 15 | 13 |
| C-2 | CysII | 58 | 58 |
| C-3 | CysIII | 68 | 68 |
| C-4 | CysIV | 80 | 80 |
| C-5 | CysV | 108 | 109 |
| C-6 | CysVI | 110 | 111 |

TABLE 14D

PDGF-subfamily (PF00341)

|  |  | PDGF | PLGF | VEGF-A |
|---|---|---|---|---|
| C-1 | CysI | 16 | 35 | 26 |
| C-2 |  | 43 | 60 | 51 |
| C-3 | CysII | 49 | 66 | 57 |
| C-4 |  | 52 | 69 | 60 |
| C-5 | CysIII | 53 | 70 | 61 |
| C-6 | CysIV | 60 | 77 | 68 |
| C-7 | CysV | 97 | 111 | 102 |
| C-8 | CysVI | 99 | 113 | 104 |

TABLE 14E

TGF-subfamily

|  |  | TGF-B2 | BMP2 | BMP7 | GDNF | GDF-15 |
|---|---|---|---|---|---|---|
| C-1 |  | 7 | — | — | — | 9 |
| C-2 | CysI | 15 | 14 | 38 | 42 | 16 |
| C-3 |  | 16 | — | — | — | 17 |
| C-4 | CysII | 44 | 43 | 67 | 69 | 46 |
| C-5 | CysIII | 48 | 47 | 71 | 73 | 50 |
| C-6 |  | 77 | 78 | 103 | 102 | 79 |
| C-7 | CysIV | 78 | 79 | 104 | 103 | 80 |
| C-8 | CysV | 109 | 111 | 136 | 132 | 111 |
| C-9 | CysVI | 111 | 113 | 138 | 134 | 113 |

---

The invention claimed is:

1. A peptidomimetic consisting of a polypeptide attached to a scaffold wherein:
   i) the polypeptide is the amino acid sequence of a cysteine-knot growth factor family member from position CysIV+x to position CysV+y, wherein $-5 \leq x \leq 1$ and $1 \leq y \leq 6$, with the proviso that x+y=−1, 0, 1 or 2,
   wherein two amino acid residues in said amino acid sequence have been replaced by a cysteine residue,
   wherein the first cysteine residue is introduced at position CysIV+p, which is located p residues C-terminal from CysIV, wherein $5 \leq p \leq 12$,
   wherein the second cysteine residue is introduced at position CysV−q, which is located q residues N-terminal from CysV, wherein $4 \leq q \leq 12$,
   wherein (p−q) is −3, −2, −1, 0, 1, 2 or 3, and
   wherein the first and second introduced cysteine residues are attached to each other via the scaffold,
   wherein cysteine residues in the amino acid sequence other than said first and second introduced cysteine residues are optionally replaced by an amino acid residue that is not reactive with the scaffold; and
   ii) wherein the scaffold is an aromatic molecule with at least two halomethyl substituents.

2. The peptidomimetic of claim 1, wherein the amino acid sequence is from CysIV+1 to CysV+1, from CysIV−5 to CysV+6, from CysIV−3 to CysV+4, from CysIV−5 to CysV+4 or from CysIV−2 to CysV+4.

3. The peptidomimetic of claim 1, wherein the position of the first and second introduced cysteines correspond to positions CysIV+12 and CysV−10, or to CysIV+11 and CysV−10, CysIV+10 and CysV−8, CysIV+9 and CysV−8, CysIV+8 and CysV−6, CysIV+7 and CysV−5, CysIV+7 and CysV−6, CysIV+7 and CysV−4, CysIV+5 and CysV−4 or CysIV+6 and CysV−4, respectively.

4. The peptidomimetic of claim 3, wherein the position of the first and second introduced cysteines correspond to positions CysIV+10 and CysV−8, respectively.

5. The peptidomimetic of claim 1, wherein the scaffold is selected from the group consisting of ortho-, meta- and para-dihalomethylbenzene, and 1,2,4,5 tetra halomethylbenzene.

6. The peptidomimetic of claim 1, wherein the amino acid sequence is from CysIV+1 to CysV+1 and wherein the scaffold is meta-1,3-bis(bromomethyl)benzene (m-T2).

7. The peptidomimetic of claim 1, wherein the amino acid sequence is from CysIV−2 to CysV+4 and wherein the scaffold is 1,2,4,5-tetra(bromomethyl)benzene (T4).

8. The peptidomimetic of claim 1, wherein the member of the cysteine-knot protein family is a member of the glycoprotein hormone-beta (GLHB) subfamily, the platelet-derived growth factor (PDGF) subfamily, the transforming growth factor (TGF) subfamily, the nerve growth factor (NGF) subfamily or the glycoprotein hormone-alpha (GLHA) subfamily.

9. The peptidomimetic of claim 1, wherein the position of said first introduced cysteine corresponds to amino acid position CysIV+10 and the position of the second introduced cysteine corresponds to position CysV−8, and wherein said member of the cystine-knot protein family is a member of the GLHB subfamily, the PDGF subfamily or the TGF subfamily.

10. The peptidomimetic of claim 3, wherein the position of the first introduced cysteine corresponds to amino acid position CysIV+8 and wherein the position of the second introduced cysteine corresponds to position CysV−6.

11. The peptidomimetic of claim 3, wherein the position of the first introduced cysteine corresponds to amino acid position CysIV+7 and wherein the position of the second introduced cysteine corresponds to position CysV−6.

12. The peptidomimetic of claim 1, wherein the position of the first introduced cysteine corresponds to amino acid position CysIV+8 and the position of the second introduced cysteine corresponds to position CysV−6, wherein the member of the cystine-knot growth factor protein family is a VEGF protein.

13. A peptidomimetic selected from the group consisting of the polypeptide TFKELVYETCRVPGAAHHAD-SLCTYPVATQAH (SEQ ID NO:31) attached to the scaffold m-T2, the polypeptide KIQKTATFKELVYET-CRVPGAAHHADSLCTYPVATQAHAGK (SEQ ID NO:32) attached to the scaffold T4, the polypeptide TFKCLVYETVRVPGAAHHADSLYTYPVACQAH (SEQ ID NO:37) attached to the scaffold m-T2, the polypeptide TFKELVYETCRVPGDAHHAD-SLCTYPVATQAH (SEQ ID NO:38) attached to the scaffold m-T2, the polypeptide TFKELVYETCRVP-GAAHHADSLCTYPVATQAH (SEQ ID NO:31) attached to the scaffold T3, the polypeptide TFKELVY-ETCRVPGDAHHADKLCTYPVATQAH (SEQ ID NO:40) attached to the scaffold m-T2, the polypeptide TFKELVYETCRVPGDAHKAIDSLCTYPVATQAH (SEQ ID NO:41) attached to the scaffold m-T2, the polypeptide ESNCTMQIMRIKPHQGQHIGEM-SCLQH (SEQ ID NO: 42) attached to the scaffold m-T2, the polypeptide EESNCTMQIMRIKPHQGQHIGEM-SCLQHN (SEQ ID NO:43) attached to the scaffold m-T2, the polypeptide NYRDVRFESCRLP-GAPRGVNPVCSYAVALSAQ (SEQ ID NO: 126) attached to the scaffold m-T2, the polypeptide VVANYRDVRFESCRLPGAPRGVNPVC-SYAVALSAQAAL (SEQ ID NO:35) attached to the scaffold m-T2, and a dimer of the polypeptide NYRDVRFESCRLPGCPRGVNPVCSYAVALSAQ (SEQ ID NO:44) wherein the monomers are joined by a disulfide bond between the cysteine at position 15 in each monomer and wherein each monomer is individually attached to the scaffold m-T2;

wherein the scaffold m-T2 is meta-1,3-bis(bromomethyl) benzene, the scaffold T3 is 2,4,6-tris(bromomethyl) mesitylene and the scaffold T4 is 1,2,4,5-tetra(bromomethyl)benzene; and wherein in each peptidomimetic the two cysteines of the polypeptide are attached via the scaffold.

14. A method for preparing a peptidomimetic of claim 1, comprising:

providing said polypeptide and scaffold, and contacting said polypeptide and scaffold under conditions that allow for the covalent attachment of said polypeptide to said scaffold.

15. A composition comprising the peptidomimetic of claim 1.

16. The composition of claim 15, wherein the peptidomimetic is coupled to a carrier.

17. The peptidomimetic of claim 5, wherein said scaffold is selected from the group consisting of meta-1,3-bis(bromomethyl)benzene (m-T2) and 1,2,4,5-tetra(bromomethyl)benzene (T4).

* * * * *

UNITED STATES PATENT AND TRADEMARK OFFICE
CERTIFICATE OF CORRECTION

| | | |
|---|---|---|
| PATENT NO. | : 7,863,239 B2 | Page 1 of 1 |
| APPLICATION NO. | : 11/795922 | |
| DATED | : January 4, 2011 | |
| INVENTOR(S) | : Peter Timmerman et al. | |

It is certified that error appears in the above-identified patent and that said Letters Patent is hereby corrected as shown below:

In the specification:

COLUMNS 77, 78, replace TABLE 13 which now includes SEQ ID NOs:
and corrects the sequence for SEQ ID NO:154 as follows:
CVPQALEPLPIVYY[[Y]]VGRKPKVEQLSNMIVRS TABLE 13 - continued Alignment of various members of the cys-knot protein family

| | CysIV (B3-loop) | | CysV CysVI + C-terminus |
|---|---|---|---|
| hGLHA | CVAKSYNRVTVMGGFKVENHTA | CH | CSTCYYHKS (SEQ ID NO 143) |
| hFSH-β | CTFKELVYETVRVPGCAHHADSLYTYPVATQ | CH | CGKCDSDSTDCTVRGLGPSYCSFGEMKE (SEQ ID NO:144) |
| hCG-β | CNYRDVRFESIRLPGCPRGVNPVVSYAVALS | CQ | CALCRRSTTDCGGPKDHPLTCDDPRFQDSSS SKAPPPSLPSPSRLPGPSDTPILPQ (SEQ ID NO:145) |
| hTSH-β | CTYRDFIYRTVEIPGCPLHVHPYFSYPVALS | CK | CGKCNTDYSDCIHEAIKTNYCTKPQKSYLVGFSV (SEQ ID NO:146) |
| hLH-β | CTYRDVRFESIRLPGCPRGVDPVVSFPVALS | CR | CGPCRRSTSDCGGPKDHPLTCDIIPQLSGLLFL (SEQ ID NO:147) |

| | CysIV (B3-loop) | | CysV CysVI |
|---|---|---|---|
| hNGF | CTTTHTFVKALTMDGKQAAWRFIRIDTA | CV | CVLSRKAVRRA (SEQ ID NO:148) |
| hBDNF | CRTTQSYVRALTMDSKKRIGWRFIRIDTS | CV | CTLTIKRGR (SEQ ID NO:149) |
| hVEGF-a | CVPTEESNITMQIMRIKPHQGQHIGEMSFLQHNK | CE | CRPKKDR (SEQ ID NO:150) |
| hPLGF | CVPVETANVTMQLLKIRSGDRPSYVELTFSQHVR | CE | CRPLREK (SEQ ID NO:151) |
| hPDGF-a | CQPSRVHHRSVKVAKVEYVRKKPKLKEVQVRLEEHLE | CA | CATTSLN (SEQ ID NO:152) |
| hPDGF-b | CRPTQVQLRPVQVRKIEIVRKKPIFKKATVTLEDHLA | CK | CETVAAA (SEQ ID NO:153) |
| hTGFβ-1 | CVPQALEPLPIVYYVGRKPKVEQLSNMIVRS | CK | CS (SEQ ID NO:154) |
| hBMP-2 | CVPTELSAISMLYLDENEKVVLKNYQDMVVEG | CG | CR (SEQ ID NO:155) |
| hBMP-7 | CAPTQLNAISVLYFDDSSNVILKKYRNMVVRA | CG | CH (SEQ ID NO:156) |
| hBMP-10 | CVPTKLEPISILYLDKGVVTYKFKYEGMAVSE | CG | CR (SEQ ID NO:157) |
| hGDNF | CRPIAFDDDLSFLDDNLVYHILRKHSAKR | CG | CI (SEQ ID NO:158) |
| hGDF-5 | CVPTRLSPISILFIDSANNVVYKQYEDMVVES | CG | CR (SEQ ID NO:159) |
| hGDF-15 | CVPASYNPMVLIQKTDTGVSLQTYDDLLAKD | CH | CI (SEQ ID NO:160) |

In the claims:

CLAIM 13, COLUMN 156, LINE 43,    change "consisting of" to --consisting of:--

Signed and Sealed this
Third Day of June, 2014

Michelle K. Lee
*Deputy Director of the United States Patent and Trademark Office*